(12) United States Patent
Coradetti et al.

(10) Patent No.: US 11,560,576 B1
(45) Date of Patent: Jan. 24, 2023

(54) METHODS OF PRODUCING LIPID-DERIVED COMPOUNDS AND HOST CELLS THEREOF

(71) Applicant: National Technology & Engineering Solutions of Sandia, LLC, Albuquerque, NM (US)

(72) Inventors: Samuel Coradetti, Berkeley, CA (US); John Michael Gladden, Alameda, CA (US); Di Liu, Emeryville, CA (US); Gina Marie Geiselman, Alameda, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 17/323,195

(22) Filed: May 18, 2021

(51) Int. Cl.
| | |
|---|---|
| *C12P 7/6409* | (2022.01) |
| *C12P 7/6436* | (2022.01) |
| *C12N 9/04* | (2006.01) |
| *C12N 9/02* | (2006.01) |
| *C12N 9/10* | (2006.01) |
| *C12N 9/88* | (2006.01) |
| *C07K 14/39* | (2006.01) |
| *C12N 9/00* | (2006.01) |
| *C12N 1/15* | (2006.01) |

(52) U.S. Cl.
CPC ............ *C12P 7/6409* (2013.01); *C07K 14/39* (2013.01); *C12N 9/0006* (2013.01); *C12N 9/0008* (2013.01); *C12N 9/1029* (2013.01); *C12N 9/88* (2013.01); *C12N 9/93* (2013.01); *C12P 7/6436* (2013.01); *C12Y 101/01041* (2013.01); *C12Y 101/0302* (2013.01); *C12Y 102/01003* (2013.01); *C12Y 203/01023* (2013.01); *C12Y 401/01001* (2013.01); *C12Y 604/01002* (2013.01)

(58) Field of Classification Search
None
See application file for complete search history.

(56) References Cited

U.S. PATENT DOCUMENTS

| | | |
|---|---|---|
| 9,441,255 B2 | 9/2016 | Tian et al. |
| 9,803,182 B2 | 10/2017 | Gladden et al. |
| 10,378,000 B2 | 8/2019 | Gladden et al. |
| 10,400,254 B1 | 9/2019 | Wu et al. |
| 10,934,551 B2 | 3/2021 | Baker et al. |
| 10,934,568 B2 | 3/2021 | Gladden et al. |
| 10,941,388 B2 | 3/2021 | Singer et al. |
| 10,947,563 B2 | 3/2021 | Wu et al. |

FOREIGN PATENT DOCUMENTS

| | | |
|---|---|---|
| WO | 2017087982 A2 | 5/2017 |
| WO | 2018119152 A1 | 6/2018 |
| WO | 2020172438 A1 | 8/2020 |

OTHER PUBLICATIONS

Fillet et al., Fatty alcohols produced by oleaginous yeast, J. Ind. Microbiol. Biotechnol. 42, 2015, 1463-72. (Year: 2015).*
Schaffrath et al., Wobble uridine modifications—a reason to live, a reason to die, RNA Biol. 14, 2017, 1209-22. (Year: 2017).*
Chen, X. et al., "DMR (deacetylation and mechanical refining) processing of corn stover achieves high monomeric sugar concentrations (230 g/L) during enzymatic hydrolysis and high ethanol concentration (>10% v/v) during fermentation without hydrolyzate purification or concentration," Energy & Environmental Science, 2016, vol. 9, pp. 1237-1245.
Coradetti, S. T. et al., "Functional genomics of lipid metabolism in the oleaginous yeast *Rhodosporidium toruloides*," eLIFE, 2018, vol. 7, Article No. e32110 (55 pages).
Gupta, R. et al., "A tRNA modification balances carbon and nitrogen metabolism by regulating phosphate homeostasis," eLIFE, 2019, vol. 8, Article No. e44795 (33 pages).
Kim, J. et al., "Multi-omics driven metabolic network reconstruction and analysis of lignocellulosic carbon utilization in Rhodosporidium toruloides," Frontiers in Bioengineering and Biotechnology, 2021, vol. 8, Article No. 612832 (16 pages).
Liu, D. et al., "Exploiting nonionic surfactants to enhance fatty alcohol production in Rhodosporidium toruloides," Biotechnology and Bioengineering, 2020, vol. 117, 1418-1425.
Wang, Y. et al., "Systems analysis of phosphate-limitation-induced lipid accumulation by the oleaginous yeast *Rhodosporidium toruloides*," Biotechnology for Biofuels, 2018, vol. 11, Article No. 148 (15 pages).
Wu, S. et al., "Microbial lipid production by Rhodosporidium toruloides under sulfate-limited conditions," Bioresource Technology, 2011, vol. 102, 1803-1807.

\* cited by examiner

*Primary Examiner* — Robert B Mondesi
*Assistant Examiner* — Todd M Epstein
(74) *Attorney, Agent, or Firm* — Weaver Austin Villeneuve & Sampson LLP; Madelynne J. Farber; Samantha Updegraff

(57) ABSTRACT

The present disclosure relates to genetically engineered host cells and methods of producing a lipid-derived compound by employing such host cells. In particular embodiments, the host cell includes a first mutant gene encoding a cytoplasmic tRNA thiolation protein. Optionally, the host cell can include other mutant genes for decreasing fatty alcohol catabolism, decreasing re-importation of secreted fatty alcohol, or displaying other useful characteristics, as described herein.

15 Claims, 31 Drawing Sheets
Specification includes a Sequence Listing.

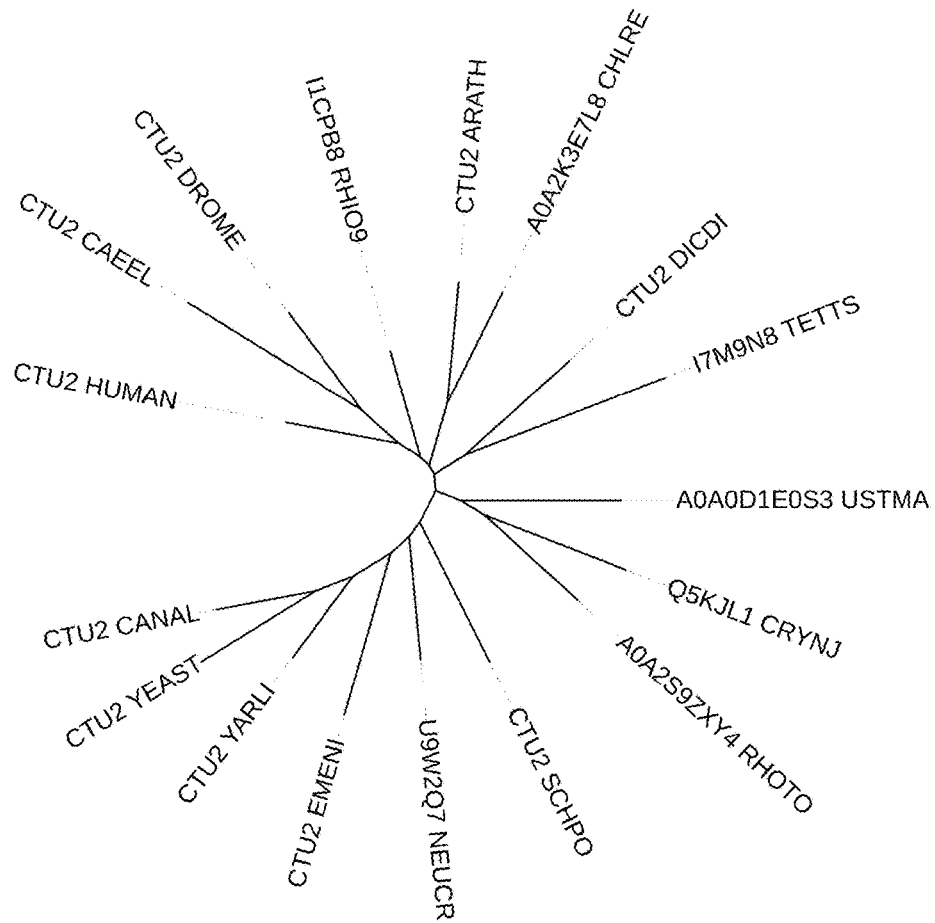

FIG. 1A

Cytoplasmic tRNA 2-thiolation protein 2 (NCS2) for *Rhodosporidium toruloides* (SEQ ID NO:1)

```
  1  MSCSQPQDDG  AAAPEQPVHA  PQHCARCALP  PTVVARGTAY  CDDHFTQSLA  SRFRRGTDGA
 61  RLYAEKGRET  YEGFAGTSDG  AARRDARRSE  ANGSERTTRL  VVAFSGGCSS  RTLLDLVKTT
121  YFSHLLPSSA  SSELTSATNG  KGKGKKHGLP  RRPVFAELEV  VFVDESSVPG  EVDATADFRR
181  IVQGATPFAR  FTALRLEDVF  ASAYSSALPL  SVSTVAPSLP  VIPPSASASA  SSTDNSDSRR
241  THLVSLLSYP  SLSPTSLASL  RTALRSSLIL  SHVRHSSSST  AVLLLGDSGT  RSAITTLSGM
301  SLGRGFSIGE  ESGAEYLAVS  RDEAVTADGQ  KSSAGEVLVV  RPLVHATLGE  VEHYCNLMGL
361  ETLWAQKRSA  AEESAKKKTI  QGLVEDFILS  LESTFPSTVS  TVTRTSHKLG  LRSSHASFLA
421  SQARSRPTAP  LETASLCPVC  GLPAPERGQA  ESWRETIAIS  NLQAVLRAEG  AGADATLRTT
481  GEEGIEARRK  PYEPSKAHLL  DPAGVAGEAV  ANGDAPTSSA  PPTTDDAGPL  LAPYLCYGCL
541  IALSSSSSAA  AKKPSSTSST  LVLPPYVQGA  LRSRVERDQG  IVGKKELRSE  EDLRREVEEF
601  LLDDEGDRAE  AV*
```

FIG. 1B

| A0A2S9ZXY4 (RHOTO) | MS------------CSQPQDD-------------------GAAAPEQPVH-----------------APQHCARCALPPTV-VARGTA------ | 39 |
| Q2VPK5.1 (HUMAN) | M-----------CQVGED------------YGEPAPEPPPAPRP-----------------SREQKCVKCK-EAQPVVIRAG------ | 43 |
| Q5KJL1 (CRYNJ) | MA----------FVTK-------------------------------------------RTCFEAAV-FSR------ | 17 |
| A0A0D1EOS3 (USTMA) | MP----------CPQPDDP------------PPSDAVTAHGTH---------------PSTTCVRCKTNPAITILRDSI------ | 42 |
| Q9UUC7.1 (SCHPO) | -------------------------------------MQNTALDNSADSKCSKCDNKA----TVLTKS------ | 27 |
| I1CPB8 (RHIO9) | ------------------------------------------------------------------------------------ | 0 |
| Q59ZY9.2 (CANAL) | --------------------------------MPEAIVYLTETEI------------------CQKCKTEN---AVVHARV- | 28 |
| Q55EX7.1 (DICDI) | MSSEELPSCGINDNDINNTIPINTRKVQIIPNGNTQCVKCLYNVA--NNVKDKKLSKKEKKEQKLKEEENNNNNEEPITQ | 79 |
| Q9VIV3.1 (DROME) | M-------CSIGEDDFGDEGAAHAMVVESLPLGIV------------------LSPGNCSKCDVNSGELYKLNFR----- | 50 |
| Q5BHB8.2 (EMENI) | ------------------------------------------------------------------------------------ | 0 |
| A0A2K3E7L8 (CHLRE) | ------------------------------------------------------------------------------------ | 0 |
| Q6CF50.1 (YARLI) | ------------------------MSAE-----------ST-----------------CRRCD----GPTAIKTRQ------ | 20 |
| O65628.3 (ARATH) | MACNS-SGCESGCYD-REKDNGSKIVDDAVSGGGNH------------------ESVCVKCKCNAPMTFGDGGFDDGR----- | 58 |
| U9W2Q7 (NEUCR) | ----------------MASTSPPSTSSPAAMSSTTTATTATAKPCIKCRS--NPGTLDSRG------ | 44 |
| Q75BK0.1 (ASHGO) | ------------MK--------------------------------------CKRCTTSE--GCLVSRN------ | 17 |
| A6ZRW4.1 (YEAST Y) | ------------ME--------------------------------------CQRCSASARNPATVESRK------ | 20 |
| Q19906.2 (CAEEL) | -------------------MELGNFV--TDLNGKKCVKCDKDAKFTGVDPKK------ | 31 |
| B5VQS7.1 (YEAST A) | ------------ME--------------------------------------CQRCPASARNPATVESRK------ | 20 |
| P53923.1 (YEAST S) | ------------ME--------------------------------------CQRCPASARNPATVESRK------ | 20 |
| B3LNX6.1 (YEAST R) | ------------ME--------------------------------------CQRCPASARNPATVESRK------ | 20 |

| A0A2S9ZXY4 (RHOTO) | ---YCDDHFTQSLASRFRGTDGARLYAEKGRETYEGFAGTSDGAARRDAR-------RSEA | 91 |
| Q2VPK5.1 (HUMAN) | ---DAFCRDCFKAFYVHKFRAMLGKNRLI-----------------FP--GE----- | 73 |
| Q5KJL1 (CRYNJ) | ---FTKSLHPPLKSPI-----------------SSRSAASSGYR-------PFAQ | 45 |
| A0A0D1EOS3 (USTMA) | ---YCQACALAVFYQKAKAGLEYAR----GAGLSKYVAAAKAASSAAGSPAESRQTFSSSTSTFPPAA | 103 |
| Q9UUC7.1 (SCHPO) | ---DAVCDSCFVRRIENKIRRQFELVRPN--------------------LQGR----- | 57 |
| I1CPB8 (RHIO9) | ------------------------------------------------------------------------------------ | 0 |
| Q59ZY9.2 (CANAL) | ---EKLCSNCYIRFIRGKLRKQ---MHDER-----------YKVKFGRAV---EQYGT----Q----- | 67 |
| Q55EX7.1 (DICDI) | QQKPIGKPIINFRSEQLCWECYRELILKKFKLNIVKVRES------------K---RDAE------ | 124 |
| Q9VIV3.1 (DROME) | ---TAECRECFLAYARHKFRAALGAAKIL-----------------PR---NA------ | 80 |
| Q5BHB8.2 (EMENI) | ---MCHACLELSVRGKVR--ALKTHKLL-----------------MEKYRLRRD-----L---PR | 12 |
| A0A2K3E7L8 (CHLRE) | ---ANFCQPCFITFIQQKORKA---M--------------------LP----GD----- | 27 |
| Q6CF50.1 (YARLI) | ---FCADCFRNNVFGKFKFRLAVTSHAMI--------------------EGCKVL--FARPGC----- | 58 |
| O65628.3 (ARATH) | --------------------------------TP---SD---------VLPPAI | 86 |
| U9W2Q7 (NEUCR) | ---QLVCHICFQKFISQKCIKQIGLLNKD-------VRSSSSQSLSAYHLSQK---NSGPPQ | 93 |
| Q75BK0.1 (ASHGO) | ---ETFCGECFSRFVLLKFRKQ--MMDE-----------YCQQVFKVLYADKHRTA---VEADEQ | 64 |
| A6ZRW4.1 (YEAST Y) | ---EKFCDECFIKFVSTKQRKQ--MMKDE-----------YFRNLFKVIYPFEKEGS-------V----- | 62 |
| Q19906.2 (CAEEL) | ---AWYCQECFVQMVRNKFRSSLSKKKIY-----------------KD-ADAR | 63 |
| B5VQS7.1 (YEAST A) | ---EKFCDECFIKFVSTKQRKQ--MMKDE-----------YFRNLFKVIYPFEKEGS-------V----- | 62 |
| P53923.1 (YEAST S) | ---EKFCDECFIKFVSTKQRKQ--MMKDE-----------YFRNLFKVIYPFEKEGS-------V----- | 62 |
| B3LNX6.1 (YEAST R) | ---EKFCDECFIKFVSTKQRKQ--MMKDE-----------YFRNLFKVIYPFEKEGS-------V----- | 62 |

```
A0A2S9ZXY4 (RHOTO)   ----------------------------------------------------------------           604
Q2VPK5.1  (HUMAN)    ------------------------------AKKPSSTSSTL-------VLPPYVQGALRSRVERDQGIVGKKELRSEEDLRREVEEFLLDD  604
Q5KJL1    (CRYNJ)    --------------------------------------------------LPPYILAEAQLRT---------QRAWGLQEI------RDCLIED  507
A0A0D1E0S3 (USTMA)   ------------------------------KAKAKAQTAGLTVNGDE-PVLLPVWNEGVKRRQ---------MGRREMKDE------IKEFLIEE  510
Q9UUC7.1  (SCHPO)    LPSTVLHHIHRSTHHAGAQHPHHIASRPLADDHE-----LPPEHKTNQAACATHNMPNPIPQPLKPSQ-IKAHISEFLIE-  687
I1CPB8    (RHIO9)    IEKEGI---------------------------------------------------------------------------  366
Q59ZY9.2  (CANAL)    ---------------------------------------------------------------------------------  267
Q55EX7.1  (DICDI)    PLQGSSELKYEYRNDNQEKQKVLDEFVLTDDEGDIEV--------IAPYIKENSKQLL---------TTSQLKNEI------KDFLLNS  452
Q9VIV3.1  (DROME)    -----------------------------------------------L---------------------------------  405
Q5BHB8.2  (EMENI)    ----------------------------------------ERSRPGLS--------------------------------  325
A0A2K3E7L8 (CHLRE)   -----------------------FRPGHHEARGREEAGGSGNVDGPSLVQGLL--------PEALAA-  518
Q6CF50.1  (YARLI)    PK-----------RASKQDILDEFTL-------------------------------------------------------  424
O65628.3  (ARATH)    SS---------------------------------------FLPDHMISQVKHQ------KVDSQAYLREKI-------KDCLLLD  453
U9W2Q7    (NEUCR)    ------------------------ERSIRG-----------------------------------------------  497
Q75BK0.1  (ASHGO)    P---------SREHDVSQVLAEFTLTD--EE---------------------------------  461
A6ZRW4.1  (YEAST Y)  PKVDTMDITANATNKNKELSQILDQFEINSDGEE-------------------------------  493
Q19906.2  (CAEEL)    ---------------------------------------------------------------------------  349
B5VQS7.1  (YEAST A)  PKVDTMDITANATNNNKELSQILDQFEINSDGEE-------------------------------  493
P53923.1  (YEAST S)  PKVDTMDITANATNKNKELSQILDQFEINSDGEE-------------------------------  493
B3LNX6.1  (YEAST R)  PKVDTMDITANATNNNKELSQILDQFEINSDGEE-------------------------------  493

A0A2S9ZXY4 (RHOTO)   EGDRAEAV-  612  (SEQ ID NO:1)
Q2VPK5.1  (HUMAN)    SDDEAGQS-  515  (SEQ ID NO:2)
Q5KJL1    (CRYNJ)    ---------  510  (SEQ ID NO:3)
A0A0D1E0S3 (USTMA)   ---------  687  (SEQ ID NO:4)
Q9UUC7.1  (SCHPO)    ---------  366  (SEQ ID NO:5)
I1CPB8    (RHIO9)    ---------  267  (SEQ ID NO:6)
Q59ZY9.2  (CANAL)    ---------  452  (SEQ ID NO:7)
Q55EX7.1  (DICDI)    DDDDDDEDN  523  (SEQ ID NO:8)
Q9VIV3.1  (DROME)    ---------  405  (SEQ ID NO:9)
Q5BHB8.2  (EMENI)    ---------  325  (SEQ ID NO:10)
A0A2K3E7L8 (CHLRE)   ---------  518  (SEQ ID NO:11)
Q6CF50.1  (YARLI)    ---------  424  (SEQ ID NO:12)
O65628.3  (ARATH)    DEEVV----  458  (SEQ ID NO:13)
U9W2Q7    (NEUCR)    ---------  497  (SEQ ID NO:14)
Q75BK0.1  (ASHGO)    ---------  461  (SEQ ID NO:15)
A6ZRW4.1  (YEAST Y)  ---------  493  (SEQ ID NO:16)
Q19906.2  (CAEEL)    ---------  349  (SEQ ID NO:17)
B5VQS7.1  (YEAST A)  ---------  493  (SEQ ID NO:18)
P53923.1  (YEAST S)  ---------  493  (SEQ ID NO:19)
B3LNX6.1  (YEAST R)  ---------  493  (SEQ ID NO:20)
```

```
Q5KJL1 (CRYNJ)     MKSRTALTFLST------------------KTEPTAISKQQQPQH-------------GETEA-------LA 442
Q9UUC7.1 (SCHPO)   WLQKTTVEHPDSVE--------------------GIKNQ-------------------------N-------- 340
Q59ZY9.2 (CANAL)   WLKRITVTDPAAIT----------------TDEEKEYYEMFRAS---------L----SPDNEDK-NNS----DSPID--- 395
Q5BHB8.2 (EMENI)   -------GRQTMD-----------------------LEE-----------------------RPTNH------------- 312
Q6CF50.1 (YARLI)   WLTNITVNEPAAPE----------------TEEEEELSKKAHMEK--------------SQEK-TGDADRHLPVPN----- 392
O65628.3 (ARATH)   ------------------------------SELDTFEEGQESDVLYAAC------------------------------ 400
Q75BK0.1 (ASHGO)   WLKSITVNNCHPPA----------------SDEDMSMLQMWESSSKGKETL----------ARNQA-RSNIWSTAAEAP-- 422
A6ZRW4.1 (YEAST Y) WLNRITVTSPYPVE----------------TTEEKYLFKQWQDSKLGQSHTHYVELL----NEIKQGA-SNSLDVEDSDVK- 439
B5VQS7.1 (YEAST A) WLNRITVTSPYPVE----------------TTEEKYLFKQWQDSKLGQSHTHYVELL----NEIKQGA-SNSLDVEDGDVK- 439
P53923.1 (YEAST S) WLNRITVTSPYPVE----------------TTEEKYLFKQWQDSKLGQSHTHYVELL----NEIKQGA-SNSLDVEDGDVK- 439
B3LNX6.1 (YEAST R) WLNRITVTSPYPVE----------------TTEEKYLFKQWQDSKLGQSHTHYVELL----NEIKQGA-SNSLDVEDGDVK- 439
A0A2S9ZXY4 (RHOTO) WRETIAISNLQAVLRAEGAGADATLRTTGEEGIEARRKPYEPSKAHLLDPAGVAGEAVANGDAPTSSAPPTTDDAGPLLA 532
A0A0D1E0S3 (USTMA) WKRDITISSLAETA----------------PRSRQTVETQATCQSSEQADWLE----------------------LC 591
U9W2Q7 (NEUCR)     WKGELGEDSYRDAL--------------------------------V------------------VDKGA------KR-MK 484

Q5KJL1 (CRYNJ)     PLCYSCLTTTP-PTVVS----------KAKAKAQTAGLTVNGDEPVLLPVWNEGVKRRQ---------- 493
Q9UUC7.1 (SCHPO)   -CVCSVS-----KSL--KGTLHI----PDIEKEGI---------------- 366
Q59ZY9.2 (CANAL)   -CCTVT-----GGVKGDTGFIW----PLQGSSELKYEYRN------------ 429
Q5BHB8.2 (EMENI)   FCYCERSR---PGLS--------------- 325
Q6CF50.1 (YARLI)   CYCIIT---RDT--DSFTF-----PK------------------ 411
O65628.3 (ARATH)   CSSCRFQLPQDGSSLEQFSSFL------PDHMISQVKHQKVD----- 437
Q75BK0.1 (ASHGO)   CYCVVT-----NET-KDRELNW-----P--------S-------- 443
A6ZRW4.1 (YEAST Y) CYCLIL-----NTSIKDKNLVW----PKVDTMDITANATN----- 473
B5VQS7.1 (YEAST A) CYCLIL-----NTSIKDKNLVW----PKVDTMDITANATN----- 473
P53923.1 (YEAST S) CYCLIL-----NTSIKDKNLVW----PKVDTMDITANATN----- 473
B3LNX6.1 (YEAST R) CYCLIL-----NTSIKDKNLVW----PKVDTMDITANATN----- 473
A0A2S9ZXY4 (RHOTO) PYCYCLIASS--SSSAA------AKKPSSTSSTL----VLPPYVQGALRSRVERDQGI 581
A0A0D1E0S3 (USTMA) NHCYCLLVSP--AISSAHPAMLPSTVLHHIHRSTHHAGAQHPHHIASRPLADDHE----LPPEHKTNQAACATHNMPN 666
U9W2Q7 (NEUCR)     QRCYCERSRG---------------------- 497

CONS8              XCXXCXXXX (SEQ ID NO:28)
```

FIG. 3E

| | | | |
|---|---|---|---|
| Q5KJL1 (CRYNJ) | MGRRREMKDE-------IKEFLIEE------------ | 510 | (SEQ ID NO:3) |
| Q9UUC7.1 (SCHPO) | ---------------------------- | 366 | (SEQ ID NO:5) |
| Q59ZY9.2 (CANAL) | -------DNQEKQKVLDEFVLTDDEGDIEV- | 452 | (SEQ ID NO:7) |
| Q5BHB8.2 (EMENI) | ---------------------------- | 325 | (SEQ ID NO:10) |
| Q6CF50.1 (YARLI) | -------RASKQDILDEFTL--------- | 424 | (SEQ ID NO:12) |
| O65628.3 (ARATH) | -------SQAYLREKIKDCLLLDDEEVV- | 458 | (SEQ ID NO:13) |
| Q75BK0.1 (ASHGO) | -------REHDVSQVLAEFTLTD--EE-- | 461 | (SEQ ID NO:15) |
| A6ZRW4.1 (YEAST Y) | -------KNKELSQILDQFEINSDGEE-- | 493 | (SEQ ID NO:16) |
| B5VQS7.1 (YEAST A) | -------NNKELSQILDQFEINSDGEE-- | 493 | (SEQ ID NO:18) |
| P53923.1 (YEAST S) | -------KNKELSQILDQFEINSDGEE-- | 493 | (SEQ ID NO:19) |
| B3LNX6.1 (YEAST R) | -------NNKELSQILDQFEINSDGEE-- | 493 | (SEQ ID NO:20) |
| A0A2S9ZXY4 (RHOTO) | VGKKELRSEEDLRREVEEFLLDDEGDRAEAV | 612 | (SEQ ID NO:1) |
| A0A0D1E0S3 (USTMA) | PIPQPLKPSQ-IKAHISEFLIE------- | 687 | (SEQ ID NO:4) |
| U9W2Q7 (NEUCR) | ---------------------------- | 497 | (SEQ ID NO:14) |

FIG. 3F

Acetyl-CoA carboxylase 1 (ACC1) for *Rhodosporidium toruloides* (SEQ ID NO:30)

```
   1  MPFSGEAKAV  NGSHSVDEAP  KNPKYDHGRV  VKYLGGNSLE  SAPPSKVADW  VRERGGHTVI
  61  TKILIANNGI  AAVKEIRSVR  KWAYETFGSE  RAIEFTVMAT  PEDLKVNADY  IRMADQYVEV
 121  PGGTNNNNYA  NVDVIVDVAE  RAGVHAVWAG  WGHASENPRL  PESLAASKHK  IVFIGPPGSA
 181  MRSLGDKISS  TIVAQHAQVP  CMDWSGQGVD  QVTQSPEGYV  TVADDVYQQA  CVHDADEGLA
 241  RASRIGYPVM  IKASEGGGGK  GIRKVEKEQD  FKQAFQAVLT  EVPGSPVFIM  KLAGAARHLE
 301  VQVLADQYGN  AISLFGRDCS  VQRRHQKIIE  EAPVTIAKPD  TFEQMEKSAV  RLAKLVGYVS
 361  AGTVEFLYSA  ADDKFAFLEL  NPRLQVEHPT  TEMVSGVNLP  AAQLQVAMGV  PLHRIRDIRT
 421  LYGKAPNGSS  EIDFDFENPE  SAKTQRKPSP  KGHVVAVRIT  AENPDAGFKP  SMGTLQELNF
 481  RSSTNVWGYF  SVGSAGGLHE  FADSQFGHIF  AYGSDRSESR  KNMVVALKEL  SIRGDFRTTV
 541  EYLIKLLETD  AFEQNTITTA  WLDSLISARL  TAERPDTTLA  IICGAVTKAH  LASEANIAEY
 601  KRILEKGQSP  AKELLATVVP  LEFVLEDVKY  RATASRSSPS  SWSIYVNGSN  VSVGIRPLAD
 661  GGLLILLDGR  SYTCYAKEEV  GALRLSIDSR  TVLIAQENDP  TQLRSPSPGK  LVRYFIESGE
 721  HISKGEAYAE  IEVMKMIMPL  IAAEDGIAQF  IKQPGATLEA  GDILGILSLD  DPSRVHHAKP
 781  FDGQLPALGL  PSIIGNKPHQ  RFAYLKDVLS  NILMGYDNQA  VMQSSIKELI  SVLRNPELPY
 841  GEANAVLSTL  SGRIPAKLEQ  TLRQYIDQAH  ESGAEFPSAK  CRKAIDTTLE  QLRPAEAQTV
 901  RNFLVAFDDI  VYRYRSGLKH  HEWSTLAGIF  AAYAETEKPF  SGKDGDVVLE  LRDAHRDSLD
 961  SVVKIVLSHY  KAASKNSLVL  ALLDIVKDSD  SVPLIEQVVS  PALKDLADLD  SKATTKVALK
1021  AREVLIHIQL  PSLDERLGQL  EQILKASVTP  TVYGEPGHDR  TPRGEVLKDV  IDSRFTVFDV
1081  LPSFFQHQDH  WVSLAALDTY  VRRAYRSYNL  LNIEHIEADA  AEDEPATVAW  SFRMRKAASE
1141  SEPPTPTTGL  TSQRTASYSD  LTFLLNNAQS  EPIRYGAMFS  VRSLDRFRQE  LGTVLRHFPD
1201  SNKGKLQQQP  AASSSQEQWN  VINVALTVPA  SAQVDEALR  ADFAAHVNAM  SAEIDARGMR
1261  RLTLLICREG  QYPSYYTVRK  QDGTWKELET  IRDIEPALAF  QLELGRLSNF  HLEPCPVENR
1321  QVHVYYATAK  GNSSDCRFFV  RALVRPGRLR  GNMKTADYLV  SEADRLVTDV  LDSLEVASSQ
1381  RRAADGNHIS  LNFLYSLRLD  FDEVQAALAG  FIDRHGKRFW  RLRVTGAEIR  IVLEDAQGNI
1441  QPIRAIIENV  SGFVVKYEAY  REVTTDKGQV  ILKSIGPQGA  LHLQPVNFPY  PTKEWLQPKR
1501  YKAHVVGTTY  VYDFPDLFRQ  AIRKQWKAAG  KTAPAELLVA  KELVLDEFGK  PQEVARPPGT
1561  NNIGMVGWIY  TIFTPEYPTG  RRVVVIANDI  TFKIGSFGPE  EDRYFFAVTQ  LARQLGLPRV
1621  YLSANSGARL  GIAEELVDLF  SVAWVDSSRP  EKGFKYLYLT  AEKLGELKNK  GEKSVITKRI
1681  EDEGETRYQI  TDIIGLQEGL  GVESLKGSGL  IAGETSRAYD  DIFTITLVTA  RSVGIGAYLV
1741  RLGQRAVQVE  GQPIILTGAG  ALNKVLGREV  YSSNLQLGGT  QIMYKNGVSH  LTAANDLEGV
1801  LSIVQWLAFV  PEHRGAPLPI  MPSPVDPWDR  SIDYTPIKGA  YDPRWFLAGK  TDEADGRWLS
1861  GFFDKGSFQE  TLSGWAQTVV  VGRARLGGIP  MGAIAVETRT  IERIVPADPA  NPLSNEQKIM
1921  EAGQVWYPNS  SFKTGQAIFD  FNREGLPLII  FANWRGFSGG  QQDMFDEVLK  RGSLIVDGLS
1981  AYKQPVFVYI  VPNGELRGGA  WVVLDPSINA  EGMMEMYVDE  TARAGVLEPE  GIVEIKLRKD
2041  KLLALMDRLD  PTYHALRVKS  TDVSLSPADA  AQAKTELAAR  EKQLMPIYQQ  VALQFADSHD
2101  KAGRILSKGC  AREALEWSNA  RRYFYARLRR  RVAEEAAVKR  LGDADPTLSR  DERLAIVHDA
2161  VGQGVDLNND  LAAAAFEQG  AAAITERVKL  ARATTVASTL  AQLAQDDKEA  FAASLQQVLG
2221  DKLTAADLAR  ILA*
```

FIG. 4A

Lysophospholipid acyltransferase (ALE1) for *Rhodosporidium toruloides* (SEQ ID NO:31)

```
  1 MLLDGTAGYL AEQLGAEPSQ IKVILLLVAS VPLSLAYPWF PSTTRSQLAH LYSLVPSIIF
 61 LCFVLDLGLG FVQLLASSLA TWSIVRIGSR NNWGALMPWT VFAIVMGHLA VNHIERSLNN
121 VPVTTIEITG SQMVLVMKLI SFAWSVYDGQ RPLEELDATQ KASRIEEVPG LLPFLGYAFF
181 FPSILAGPSF TYRSFDSFTT HRLFAKEHPA DGSKPVDPTV IPPGRRRKAA KRFATGIIYL
241 AIFSTYGWKY GMNRLIDRKA VAGLTFVQKF TLMNVAGFIA RTKYYAVWCI AESAFIISGL
301 GYNPQTKHYD ASRNVRIRSI ELAPNFKVLL DSWNMNTNVW LRECIYKRVA KKGRKPGFKS
361 TQITFITSAL WHGTNPCYLM TFVLGGFCQA VNRSLRAGLR PFFLPPGALN VPNPAANEVK
421 VGDKAISLPS TPRVKLQPPP QTPLKTLYDV LGTICTIVVL NFAVVPFLLL DVQSSLQAWA
481 EVKFYALWMV FVPFFVLNVC GGTAYLKRLQ RARDKKAEGK RRSKEEQELE RKRVEWEKAE
541 EDKRRRRGEG LPSFGLDVEG MVEEEEREEM RGESVEGRKE L*
```

FIG. 4B

Fatty alcohol oxidase (FAO1) for *Rhodosporidium toruloides* (SEQ ID NO:32)

```
  1 MVNLDMTPGQ RAVLTAVADA AFQAHGPETV SEIRSLLPPG APQYQLENLE KFVRSKFSDL
 61 PGSVDALAQQ FCTSLSKENV DKIALTLSLL STRPGTLLLA GHATPFPDLT VQQRELVLQK
121 WRVSSLPLLR QAFRGLVSLA LFVAYNLYDE VLFAIGYPAS GDEKRFADPE RLRKHFPYTF
181 EKIEVSYQVF DTDMLVVGSG AGGGVVASEL SKKGWNVFVV EKGQYVKPED MAGTQRDGFK
241 RLYESEGLMA TEDGSMNVLA GSTFGGGTVV NWSASLRPQH FLREQWAKEH SLPYFLSTEY
301 AKSIEYVCDR MGVSDEHLEH NRANQLLVEG SKKLGYPISK IPQNTGGHAH ACGYCGFGCT
361 YSEKQSGTVT WLRDAAEHGA KFMTETSVER LLFAASPSSP LPTPETLDKY TPSSSRRHCI
421 GALVKDKNGN LAVIRAKQST IVSAGTIHSP AVLMRSGLKN PRIGRNLRLH PVVFTTGLYD
481 EHIRPWEGAI MTAVTGVQEN WDGSHHGVKI EVIQSFPGGQ AAGFIGWTSS KEHKKTMAQY
541 GNLLTLISIA RDRGSGRVFL DSEGKPRMDY TVNSYDGNSL VRGTIAAAEI HLVNGAKRIT
601 TAQVDVEDYI PAPGHQYLAD PKWKEWVAKI EKAGVYPGRC AIGSAHQMGS CQMGAKPSTS
661 VVDPRGRVWG TDGLYVADAS VFPTASGVNP MITNMSLSHS IARFIDEDAR ETISQPVQAQ
721 L*
```

FIG. 4C

Aldehyde dehydrogenase (HFD1) for *Rhodosporidium toruloides* (SEQ ID NO:33)

```
  1 MAAMQDTPID SIPQAYDTVT KAFLSGKTRP IAWRKAQIKK LGFLVQDNED AFVRALEQDF
 61 GRPAFETITA EINPVKAEIN EVYDHLEKWA KPRRVKTSAT WYATKPTVYS EPKGVTLVIG
121 TWNYPITLLL VPLLGAISAG CTALVKPAEQ APHVAALVAD LLPKYLDPTA FICINGAIPQ
181 ATALLKLKFD HIFYTGSGTV GKIVARAAAE HLCPVTLELG GKSPAVVLDD ADIEVVARRI
241 VWAKFTNAGQ ICISTDYVLT TPQTEPKLLE ALKRALAAFS ANPAASSSSE KSSTSLVHNP
301 NYSRIINQNH YNRVSKLLDA TKGEVVVGGG RDEKERKIEV TIVRGVKPDD SLMSEEIFGP
361 VLPIMTLPTL DDMVKFIQSR DTPLALYVFT QSKKNRDFIF ERTRSGGFVQ NDVLVQFMIP
421 GLPFGGTGAA GYGNYHGRRT FDTFSHERAS ANVPTWMDMI MASRYPPYTQ KKLKMLLFAT
481 KAVIKKPSKF GSISRLLKKL TGQA*
```

FIG. 4D

Isocitrate dehydrogenase (IDH) for *Rhodosporidium toruloides* (SEQ ID NO: 34)

```
  1  MAISPEQRIK  VQNPIVEMDG  DEMTRIIWHK  IKKDLILPFL  DVDIKYYDLG  LEYRDQTDDQ
 61  VTVDAAEAIL  KYGVGVKCAT  ITPDEARVEE  FKLKKMWKSP  NGTIRNILGG  TVFREPIIVQ
121  KVPKAVPGWT  KPIIVGRHAF  GDQYRSTDIV  VPEAGKLELV  YTPDDKSKQP  TNLEVFHFKG
181  PGVGLAMYNT  KQSITDFAQS  SFKLAIEKKL  PLYMSTKNTI  LKGYDGQWKD  IFQEIYDTQY
241  KAKFEELGIW  YEHRLIDDMV  AQMIKSSGGY  IMALKNYDGD  VQSDVVAQGF  GSLGLMSSEL
301  VTPDGKIIES  EAAHGTVTRH  YREHQKGNET  STNSIASIYA  WTRGLKFAGK  RDGNERLVQF
361  ANDMEQACVD  AVDIDGVMTK  DLALSIHGKN  MKREHYVLTL  EYLDHIAAKV  TEKFLANAPK
421  L*
```

FIG. 4E

Pyruvate decarboxylase (PDC) for *Rhodosporidium toruloides* (SEQ ID NO: 35)

```
  1  MPVSVTVGLR  CDDAAELASS  TRSHTLIPAS  PSLLPLSGSA  KHPLEHTHPT  SELAQPLNRT
 61  MSSPGQLADD  QVYLGTYLLD  RLAQLDVKCL  FGVPGDFNLT  FLDLVEEHPE  VQWIGNCNEL
121  NAAYAADGYA  RVKQAQINSI  REGEQAESKP  GQATTHGGKD  KTQGGVRGLG  ALLTTFGVGE
181  LSAVNGIAGA  YSERVPILHI  VGVPSTKLQK  SKALLHHTLG  NGEFTVFEQA  SAGITCARAF
241  LQRAEEAAEE  IDRVLLAALT  TARPAYVTLP  TDLVFVPVPK  KRLEDPIIPM  RVGFEDKNVL
301  PTGKKVEEEE  KNRLQFVVGE  IERLWNEAKE  PIILIDACAI  RYGVGHLVRD  LVHATGVKFY
361  TTPMGRTAID  EDPSNGFGGV  YVGEVTDPKV  KEVVEKTDLA  VMVGSLKSDF  NTGEFSYSFP
421  TEQTVELHSD  HTLVQYAHYP  SVSFHQLLPA  LTKVLKHKPN  VTHPPSDRGL  QTQIPDGDAD
481  KVVTQAAFWP  MMGKFFEEGD  IVVAETGTSS  FGMISTPLPK  GSTFVSQVLW  GSIGWTGGAT
541  LGALLAAKEA  PKPRRVILFI  GDGSLQLTVQ  EVATMVRLDL  KPILVVLNND  GYTIEKKIHG
601  ETAGYNDISS  WKWQSMLDFF  NAYDQPKPTR  SWLAPTRADL  ERILADDEFR  KADRIQVLEV
661  KMDKLDAPVA  LEKQGKLSAE  LNAA*
```

FIG. 4F

Aldehyde dehydrogenase (ALD) for *Rhodosporidium toruloides* (SEQ ID NO: 36)

```
  1  MSNNLTASLT  FPEGHSLKSL  DFPVGLFINN  EYSPASGGET  IEVRAPAFDK  VIAHVPRGTA
 61  EDVDRAVEAA  QKAYDTVWGE  RCPGHKRGKL  LMQLADLFEQ  HVEQLASIEA  LDNGKAYNIA
121  KAFDVSEAAA  CLRYYGGWAD  KEHGKVIEVD  NSKMAITKHE  PIGVIGQIIP  WNFPLLMFAW
181  KLGPALACGN  CIVIKVAETT  PLSAFYATQL  IAKVFPPGVV  NVVTGYGNEV  GAAISGHMKI
241  LKVAFTGSTL  VGRTIMQAAA  KSNLKPVTLE  LGGKSPNIIF  DDADMEQAVS  WSAFGLFFNA
301  GQCCCAGSRI  FVQESIYDEF  LEKLTAKVKS  MKVGQPFAAD  SFVGPATSKL  QFDRITAHIQ
361  SGKDEGAKVH  VGGNRHGDEG  YFIEPTIFTD  VTPNMRIAQE  EIFGPVLVVQ  KFKDESDVVA
421  KANDTMYGLA  AAIFSRDISR  AMRIANSVHA  GTVWLNCYNQ  LNSQVPFGGF  KQSGIGRELG
481  SYALHNYTAV  KAIHINLSQP  NPL*
```

FIG. 4G

METHODS OF PRODUCING LIPID-DERIVED COMPOUNDS AND HOST CELLS THEREOF

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SANDP013_ST25.txt," created on May 3, 2021 (size of 131 kilobytes), which is hereby incorporated by reference in its entirety.

FIELD

The present disclosure relates to genetically engineered host cells and methods of producing a lipid-derived compound by employing such host cells. In particular embodiments, the host cell includes a first mutant gene encoding a cytoplasmic tRNA thiolation protein. Optionally, the host cell can include other mutant genes for decreasing fatty alcohol catabolism, decreasing re-importation of secreted fatty alcohol, or displaying other useful characteristics, as described herein.

BACKGROUND

Fatty alcohols are a versatile class of chemicals with many consumer and industrial applications. Yet production of such compounds still rely on unsustainable and non-renewable sources, such as petroleum or harvesting from threatened animal or plant species.

The background description provided herein is for the purposes of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

The present disclosure relates to genetically engineered host cells that can produce lipid-derived compounds, such as fatty alcohols. In some embodiments, the host cell includes a first mutant gene, which encodes a cytoplasmic tRNA thiolation protein (e.g., the ncs2 gene, as described herein). In particular embodiments, the host cell is a *Rhodosporidium* cell. Non-limiting lipid-derived compounds include fatty-acyl-CoA derived chemicals, and the first mutant gene enhances the production of such chemicals.

Methods employing such host cells are also described herein. In particular embodiments, the host cell is incubated in a culture, in which the culture can include any useful medium. Non-limiting medium includes a lignocellulosic biomass, including hydrolysates thereof.

Described herein are metabolomic, proteomic and lipidomic analysis of a non-limiting host cell (e.g., including a ncs2 deletion mutant), which revealed a broad proteomic effect of the mutation and resulted in synergistic reduction of fatty-acyl-CoA incorporation into diacylglycerides. Without wishing to be limited by mechanism, we understand that this analysis shows promoting of fatty-acyl-CoA production by boosting expression of the NADPH generating malic enzyme and by reducing fatty-acyl-CoA degradation through beta oxidation.

Accordingly, in a first aspect, the present disclosure encompasses a method of producing a fatty alcohol, the method including: incubating an isolated, genetically engineered host cell in a culture; and isolating one or more fatty alcohols from the culture.

In particular embodiments, the isolated, genetically engineered host cell includes a first mutant gene encoding a cytoplasmic tRNA thiolation protein (e.g., a cytoplasmic tRNA 2-thiolation protein 2). In some embodiments, the first mutant gene includes deletion of the nucleic acid encoding the cytoplasmic tRNA thiolation protein. In other embodiments, the cytoplasmic tRNA thiolation protein includes a polypeptide sequence having at least 90% sequence identity to any one of the following SEQ ID NOs: 1-20. In yet other embodiments, the cytoplasmic tRNA thiolation protein includes a polypeptide sequence having at least 90% sequence identity to one or more of the following SEQ ID NOs: 21-28.

In some embodiments, said incubating includes a minimal concentration of a metal in the culture and/or a controlled nitrogen content.

In some embodiments, the host cell provides an increased amount of the one or more fatty alcohols, as compared to a control cell lacking the first mutant gene. In particular embodiments herein, the fatty alcohol includes a structure of R'OH, in which R' is an optionally substituted $C_{4-32}$ aliphatic. Other non-limiting fatty alcohols are described herein.

In a second aspect, the present disclosure encompasses an isolated, genetically engineered host cell including: a first mutant gene encoding a cytoplasmic tRNA thiolation protein; and a second mutant gene (e.g., any described herein).

In any embodiment herein, the host cell further includes a second mutant gene encoding a protein selected from the group consisting of an acetyl-CoA carboxylase, a lysophospholipid acyltransferase, a fatty-acyl-CoA oxidase, a fatty acid synthase, a fatty-acyl-CoA reductase, an aldehyde reductase, a fatty-acyl-CoA synthetase, a thioesterase, a carboxylic acid reductase, a fatty alcohol oxidase, a fatty alcohol reductase, an aldehyde dehydrogenase, an isocitrate dehydrogenase, or a pyruvate decarboxylase.

In any embodiment herein, the second mutant gene includes insertion of the nucleic acid encoding the acetyl-CoA carboxylase or the fatty alcohol reductase, thereby providing expression or overexpression of the acetyl-CoA carboxylase. In some embodiments, the acetyl-CoA carboxylase includes a polypeptide sequence having at least 90% sequence identity to SEQ ID NO: 30.

In any embodiment herein, the second mutant gene includes deletion of the nucleic acid encoding the lysophospholipid acyltransferase, the fatty alcohol oxidase, the aldehyde dehydrogenase, the isocitrate dehydrogenase, or the pyruvate decarboxylase. In some embodiments, the lysophospholipid acyltransferase includes a polypeptide sequence having at least 90% sequence identity to SEQ ID NO: 31; the fatty alcohol oxidase includes a polypeptide sequence having at least 90% sequence identity to SEQ ID NO: 32; the aldehyde dehydrogenase includes a polypeptide sequence having at least 90% sequence identity to SEQ ID NO: 33 or SEQ ID NO: 36; the isocitrate dehydrogenase includes a polypeptide sequence having at least 90% sequence identity to SEQ ID NO: 34; or the pyruvate decarboxylase includes a polypeptide sequence having at least 90% sequence identity to SEQ ID NO: 35.

In any embodiment herein, the first mutant gene includes deletion of the nucleic acid encoding the cytoplasmic tRNA thiolation protein. In particular embodiments, the cytoplasmic tRNA thiolation protein is cytoplasmic tRNA 2-thiolation protein 2. In other embodiments, the cytoplasmic tRNA thiolation protein includes a polypeptide sequence having at least 90% sequence identity to any one of the following SEQ ID NOs: 1-20. In yet other embodiments, the cytoplasmic tRNA thiolation protein includes a polypeptide sequence having at least 90% sequence identity to one or more of the following SEQ ID NOs: 21-28. Additional details are described herein.

Definitions

As used herein, the term "about" means+/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., J. Mol. Biol. 1990; 215:403-10; Zhang J et al., Genome Res. 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., Adv. Appl. Math. 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones. Non-limiting amino acids include glycine (Gly, G), alanine (Ala, A), valine (Val, V), isoleucine (Ile, I), leucine (Leu, L), cysteine (Cys, C), methionine (Met, M), aspartic acid (Asp, D), glutamic acid (Glu, E), arginine (Arg, R), histidine (His, H), lysine (Lys, K), asparagine (Asn, N), glutamine (Gln, Q), serine (Ser, S), threonine (Thr, T), proline (Pro, P), phenylalanine (Phe, F), tyrosine (Tyr, Y), tryptophan (Trp, W), selenocysteine (Sec, U), and pyrrolysine (Pyl, O).

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); a group of polar amino acids consists of D, E, N, and Q; and a group of amino acids having sulfur containing side chains consists of cysteine (Cys, C) and methionine (Met, M). Exemplary conservative amino acid substitution groups are valine-leucine-isoleucine, phenylalanine-tyrosine, lysine-arginine, alanine-valine, glycine-serine, glutamate-aspartate, and asparagine-glutamine. The present disclosure encompasses any sequence having a conservative amino acid sequence of any polypeptide sequence described herein.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., J. Mol. Biol. 1981; 147:195-7) and BLAST (Basic Local Alignment Search Tool; Altschul S F et al., J. Mol. Biol. 1990; 215:403-10). These and other alignment algorithms are accessible using publicly available computer software such as "Best Fit" (Smith T F et al., Adv. Appl. Math. 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

The term "host cell" refers to a living biological cell that can be transformed via insertion of an expression vector. Thus, a host cell as described herein may be a prokaryotic organism (e.g., an organism of the kingdom Eubacteria) or a eukaryotic cell.

The term "mutant" refers to a modified gene having one or more mutations or alternations in the nucleotide sequence encoding the target gene. Such mutations can include deletion of the gene or a portion thereof, deletion of one or more nucleotide sequences (or nucleotide base pairs), insertion of one or more nucleotide sequences (or nucleotide base pairs), substitution of one or more nucleotide sequences (or nucleotide base pairs), point mutations, inversions, frameshift mutations, and the like.

The term "isolated" refers to material that is substantially or essentially free of components that normally accompany it in its native state.

A "vector" or "expression vector" refers to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art. A vector can be a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

By "aliphatic" is meant a hydrocarbon group having at least one carbon atom to 50 carbon atoms ($C_{1-50}$), such as one to 32 carbon atoms ($C_{1-32}$), or one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well. Such an aliphatic can be unsubstituted or substituted with one or more groups, such as groups described herein for an alkyl group. In some embodiments, the unsubstituted aliphatic group is a $C_{1-3}$, $C_{1-6}$, $C_{1-10}$, $C_{1-12}$, $C_{1-16}$, $C_{1-18}$, $C_{1-20}$, $C_{1-24}$, $C_{1-28}$, $C_{1-32}$, $C_{1-36}$, $C_{4-10}$, $C_{4-12}$, $C_{4-16}$, $C_{4-18}$, $C_{4-20}$, $C_{4-24}$, $C_{4-28}$, $C_{4-32}$, $C_{4-36}$, $C_{8-12}$, $C_{8-16}$, $C_{8-18}$, $C_{8-20}$, $C_{8-24}$, $C_{8-28}$, $C_{8-32}$, $C_{8-36}$, $C_{12-16}$, $C_{12-18}$, $C_{12-20}$, $C_{12-24}$, $C_{12-28}$, $C_{12-32}$, $C_{12-36}$, $C_{14-16}$, $C_{14-18}$, $C_{14-20}$, $C_{14-24}$, $C_{14-28}$, $C_{14-32}$, $C_{14-36}$, $C_{16-18}$, $C_{16-20}$, $C_{16-24}$, $C_{16-28}$, $C_{16-32}$, $C_{16-36}$, $C_{18-20}$, $C_{18-24}$, $C_{18-28}$, $C_{18-32}$, $C_{18-36}$, $C_{22-24}$, $C_{22-28}$, $C_{22-32}$, or $C_{22-36}$ aliphatic group.

By "alkyl" and the prefix "alk" is meant a branched or unbranched saturated hydrocarbon group of 1 to 50 carbon atoms, such as methyl ($C_1$), ethyl ($C_2$), n-propyl ($C_3$), isopropyl ($C_3$), n-butyl ($C_4$), isobutyl ($C_4$), s-butyl ($C_4$), t-butyl ($C_4$), n-pentyl ($C_4$ or amyl), isopentyl ($C_5$), s-pentyl ($C_5$), neopentyl ($C_5$), hexyl ($C_6$ or caproyl), heptyl ($C_7$ or enantyl), octyl ($C_8$ or caprylic), nonyl ($C_9$ or pelorgonyl), decyl ($C_{10}$ or capryl), undecyl ($C_{11}$), dodecyl ($C_{12}$ or lauryl), tridecyl ($C_{13}$), tetradecyl ($C_{14}$ or myristyl), pentadecyl ($C_{18}$), hexadecyl ($C_{16}$ or cetyl or palmityl), heptadecyl ($C_{17}$ or margaryl), octadecyl ($C_{18}$ or stearyl), nonadecyl ($C_{19}$), eicosyl ($C_{20}$ or arachidyl), henicosyl ($C_{21}$), docosyl ($C_{22}$ or behenyl), tricosyl ($C_{23}$), tetracosyl ($C_{24}$ or lignoceryl), pentacosyl ($C_{25}$), hexacosyl ($C_{26}$ or cerotyl), heptacosyl ($C_{27}$ or carboceryl), octacosyl ($C_{28}$ or cluytyl or montanyl), nonacosyl ($C_{29}$), tricontyl ($C_{30}$ or myricyl or melissyl), hentriaconyl ($C_{31}$), dotriaconyl ($C_{32}$ or lacceryl), tritriacontyl ($C_{33}$), tetratriacontyl ($C_{34}$ or geddyl), tetracontyl ($C_{40}$), pentacontyl ($C_{50}$), and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —O-Ak, wherein Ak is optionally substituted $C_{1-6}$ alkyl); (2) $C_{1-6}$ alkylsulfinyl (e.g., —S(O)-Ak, wherein Ak is optionally substituted $C_{1-6}$ alkyl); (3) $C_{1-6}$ alkylsulfonyl (e.g., —SO$_2$-Ak, wherein Ak is optionally substituted $C_{1-6}$ alkyl); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —O-L-Ar, wherein L is a bivalent form of optionally substituted alkyl and Ar is optionally substituted aryl); (7) aryloyl (e.g., —C(O)—Ar, wherein Ar is optionally substituted aryl); (8) azido (e.g., —N$_3$); (9) cyano (e.g., —CN); (10) carboxyaldehyde (e.g., —C(O)H); (11) $C_{3-8}$ cycloalkyl (e.g., a monovalent saturated or unsaturated non-aromatic cyclic $C_{3-8}$ hydrocarbon group); (12) halo (e.g., F, $C_1$, Br, or I); (13) heterocyclyl (e.g., a 5-, 6- or 7-membered ring, unless otherwise specified, containing one, two, three, or four non-carbon heteroatoms, such as nitrogen, oxygen, phosphorous, sulfur, or halo); (14) heterocyclyloxy (e.g., —O-Het, wherein Het is heterocyclyl, as described herein); (15) heterocyclyloyl (e.g., —C(O)—Het, wherein Het is heterocyclyl, as described herein); (16) hydroxyl (e.g., —OH); (17) N-protected amino; (18) nitro (e.g., —NO$_2$); (19) oxo (e.g., =O); (20) $C_{3-8}$ spirocyclyl (e.g., an alkylene or heteroalkylene diradical, both ends of which are bonded to the same carbon atom of the parent group); (21) $C_{1-6}$ thioalkoxy (e.g., —S-Ak, wherein Ak is optionally substituted $C_{1-6}$ alkyl); (22) thiol (e.g., —SH); (23) —CO$_2$R$^A$, where R$^A$ is selected from the group consisting of (a) hydrogen, (b) $C_{1-6}$ alkyl, (c) $C_{4-18}$ aryl, and (d) ($C_{4-18}$ aryl) $C_{1-6}$ alkyl (e.g., -L-Ar, wherein L is a bivalent form of optionally substituted alkyl group and Ar is optionally substituted aryl); (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) ($C_{4-18}$ aryl) $C_{1-6}$ alkyl (e.g., -L-Ar, wherein L is a bivalent form of optionally substituted alkyl group and Ar is optionally substituted aryl); (25) —SO$_2$R$^D$, where R$^D$ is selected from the group consisting of (a) $C_{1-6}$ alkyl, (b) $C_{4-18}$ aryl, and (c) ($C_{4-18}$ aryl) $C_{1-6}$ alkyl (e.g., -L-Ar, wherein L is a bivalent form of optionally substituted alkyl group and Ar is optionally substituted aryl); (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) ($C_{4-18}$ aryl) $C_{1-6}$ alkyl (e.g., -L-Ar, wherein L is a bivalent form of optionally substituted alkyl group and Ar is optionally substituted aryl); and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl (e.g., optionally substituted alkyl having one or more double bonds), (e) $C_{2-6}$ alkynyl (e.g., optionally substituted alkyl having one or more triple bonds), (f) $C_{4-18}$ aryl, (g) ($C_{4-18}$ aryl) $C_{1-6}$ alkyl (e.g., L-Ar, wherein L is a bivalent form of optionally substituted alkyl group and Ar is optionally substituted aryl), (h) $C_{3-8}$ cycloalkyl, and (i) ($C_{3-8}$ cycloalkyl) $C_{1-6}$ alkyl (e.g., -L-Cy, wherein L is a bivalent form of optionally substituted alkyl group and Cy is optionally substituted cycloalkyl, as described herein), wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkenyl" is meant an optionally substituted $C_{2-50}$ alkyl group having one or more double bonds. The alkenyl group can be cyclic (e.g., $C_{3-24}$ cycloalkenyl) or acyclic. Non-limiting alkenyl groups includes palmitoleyl ($C_{16:1}$ or 16:1 $\Delta^9$), hexadecatetraenoic ($C_{16:4}$), oleoyl ($C_{18:1}$ or 18:1c $\Delta^9$), elaidyl ($C_{18:1}$), linoleyl ($C_{18:2}$ or 18:2cc $\Delta^{9,12}$), linolenyl ($C_{18:3}$ or 18:3ccc $\Delta^{9,12,15}$) eicosenyl ($C_{20:1}$), eicosadienyl ($C_{20:2}$), eicosatrienyl ($C_{20:3}$), eicosatetraenyl ($C_{20:4}$ or 20:4cccc $\Delta^{5,8,11,14}$), eicosapentenyl ($C_{20:5}$), docosenyl or erucyl ($C_{22:1}$), docosatetraenyl ($C_{22:4}$), docosahexenyl ($C_{22:6}$), tetracosenyl ($C_{24:1}$), and the like. The alkenyl group can also be substituted or unsubstituted. For example, the alkenyl group can be substituted with one or more substitution groups, as described herein for alkyl.

By "alkynyl" is meant an optionally substituted $C_{2-50}$ alkyl group having one or more triple bonds. The alkynyl group can be cyclic or acyclic. The alkynyl group can also be substituted or unsubstituted. For example, the alkynyl group can be substituted with one or more substitution groups, as described herein for alkyl.

By "biomass" is meant a compound or a material produced by growth and/or propagation of cells. In particular, a "lignocellulosic biomass" is used according to its plain ordinary meaning and refers to plant dry matter including carbohydrate (e.g., cellulose or hemicellulose) and polymer (e.g., lignin).

As used herein, the term "isolating one or more lipid-derived compounds" or "isolating one or more fatty alcohols" may be understood in the broadest sense as the purification of the lipid-derived compounds (including fatty alcohols or others described herein) from the culture or the culture broth. The compound(s) may be accumulated in the cells or may be secreted by the cells and, therefore, present in the culture medium.

By "attached," "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIGS. 1A-1B show non-limiting examples of cytoplasmic tRNA 2-thiolation protein 2 (NCS2). Provided is (A) an unrooted phylogenetic tree of NSC2 homologs in model eukaryotic species. Protein identifiers are provided as UniProt short IDs for CTU2, which is the human ortholog of S.

Figure 5:
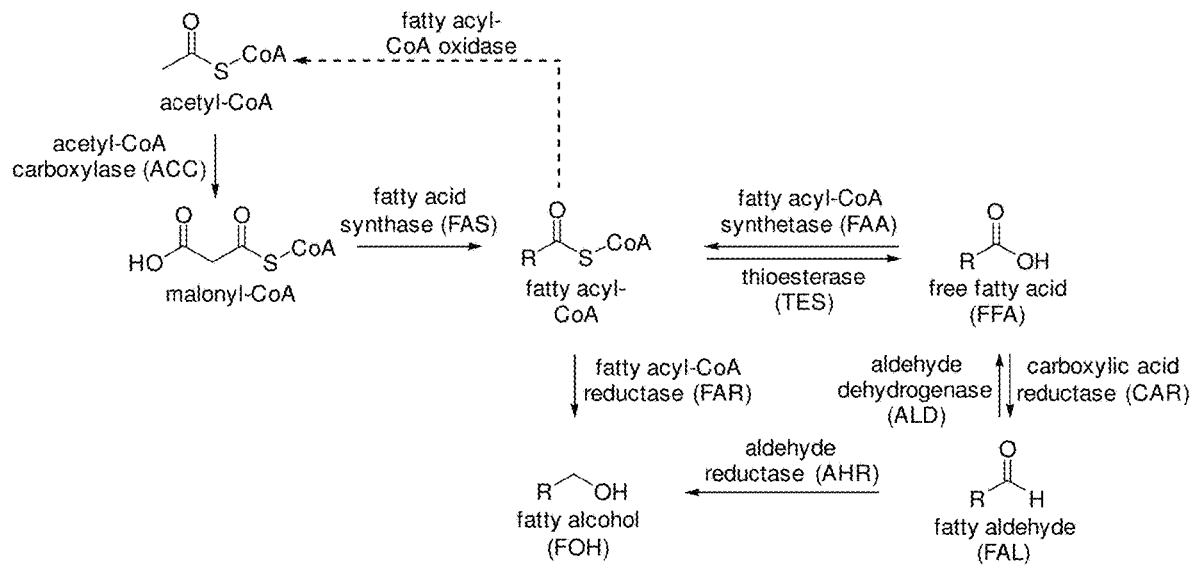

cerevisiae ncs2 and is used as the base of the UniProt name for the family. Protein identifiers include those for *Homo sapiens* (identified as "CTU2 Human," UniProtKB Entry No. Q2VPK5); *Caenorhabditis elegans* (identified as "CTU2 CAEEL," UniProtKB Entry No. Q19906); *Drosophila melanogaster* (identified as "CTU2 DROME," UniProtKB Entry No. Q9VIV3); *Rhizopus delemar* (identified as "I1CPB8 RHIO9," UniProtKB Entry No. I1CPB8); *Arabidopsis thaliana* (identified as "CTU2 ARATH," UniProtKB Entry No. O65628); *Chlamydomonas reinhardtii* (identified as "A0A2K3E7L8 CHLRE," UniProtKB Entry No. A0A2K3E7L8); *Dictyostelium discoideum* (identified as "CTU2 DICDI," UniProtKB Entry No. Q55EX7); *Tetrahymena thermophila* (identified as "I7M9N8 TETTS," UniProtKB Entry No. I7M9N8); *Ustilago maydis* (identified as "A0A0D1EOS3 USTMA," UniProtKB Entry No. A0A0D1EOS3); *Cryptococcus neoromans* (identified as "Q5KJL1 CRYNJ," UniProtKB Entry No. Q5KJL1); *Rhodosporidium toruloides* (identified as "A0A2S9ZXY4 RHOTO," UniProtKB Entry No. A0A2S9ZXY4); *Schizosaccharomyces pombe* (identified as "CTU2 SCHPO," UniProtKB Entry No. Q9UUC7); *Neurospora crassa* (identified as "U9W2Q7 NEUCR," UniProtKB Entry No. U9W2Q7); *Emericella* (*Aspergillus*) *nidulans* (identified as "CTU2 EMENI," UniProtKB Entry No. Q5BHB8); *Yarrowia lipolytica* (identified as "CTU2 YARLI," UniProtKB Entry No. Q6CF50); *Saccharomyces cerevisiae* (identified as "CTU2 YEAST," UniProtKB Entry No. P53923); and *Candida albicans* (identified as "CTU2 CANAL," UniProtKB Entry No. Q59ZY9). Also provided is (B) the sequence for cytoplasmic tRNA 2-thiolation protein 2 (NCS2) for *Rhodosporidium toruloides* (SEQ ID NO: 1).

Figure 2B:
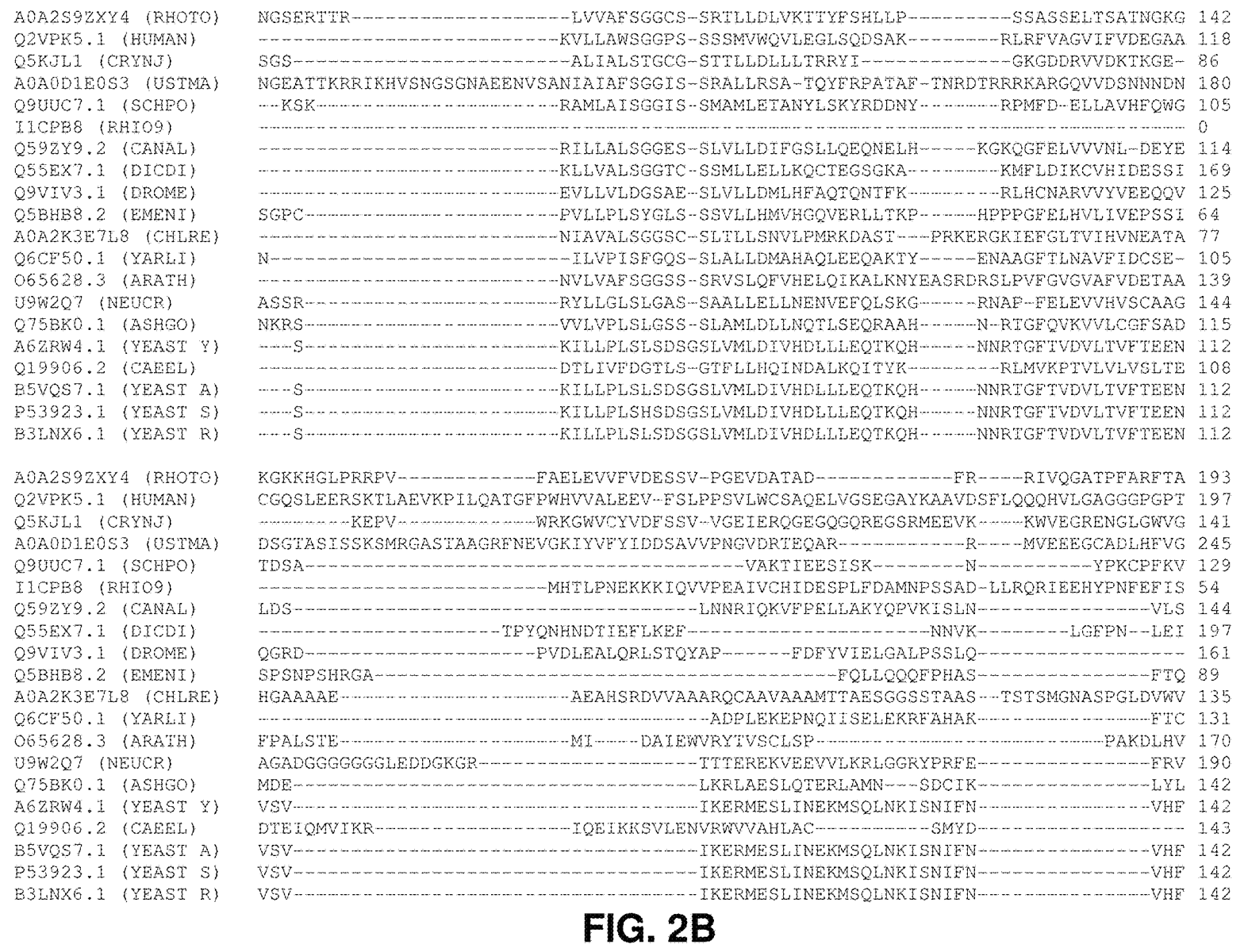
Figure 2C:
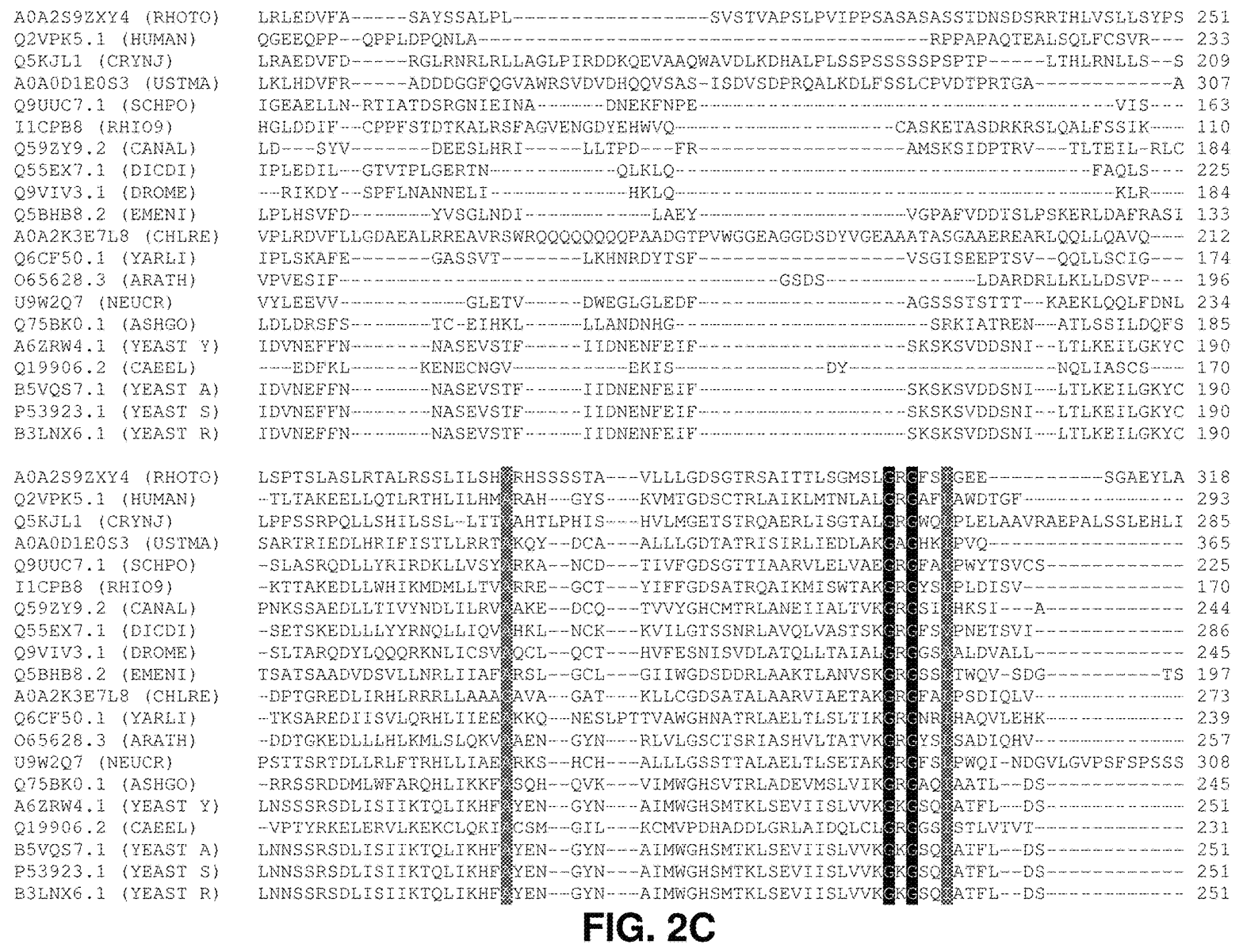
Figure 2D:
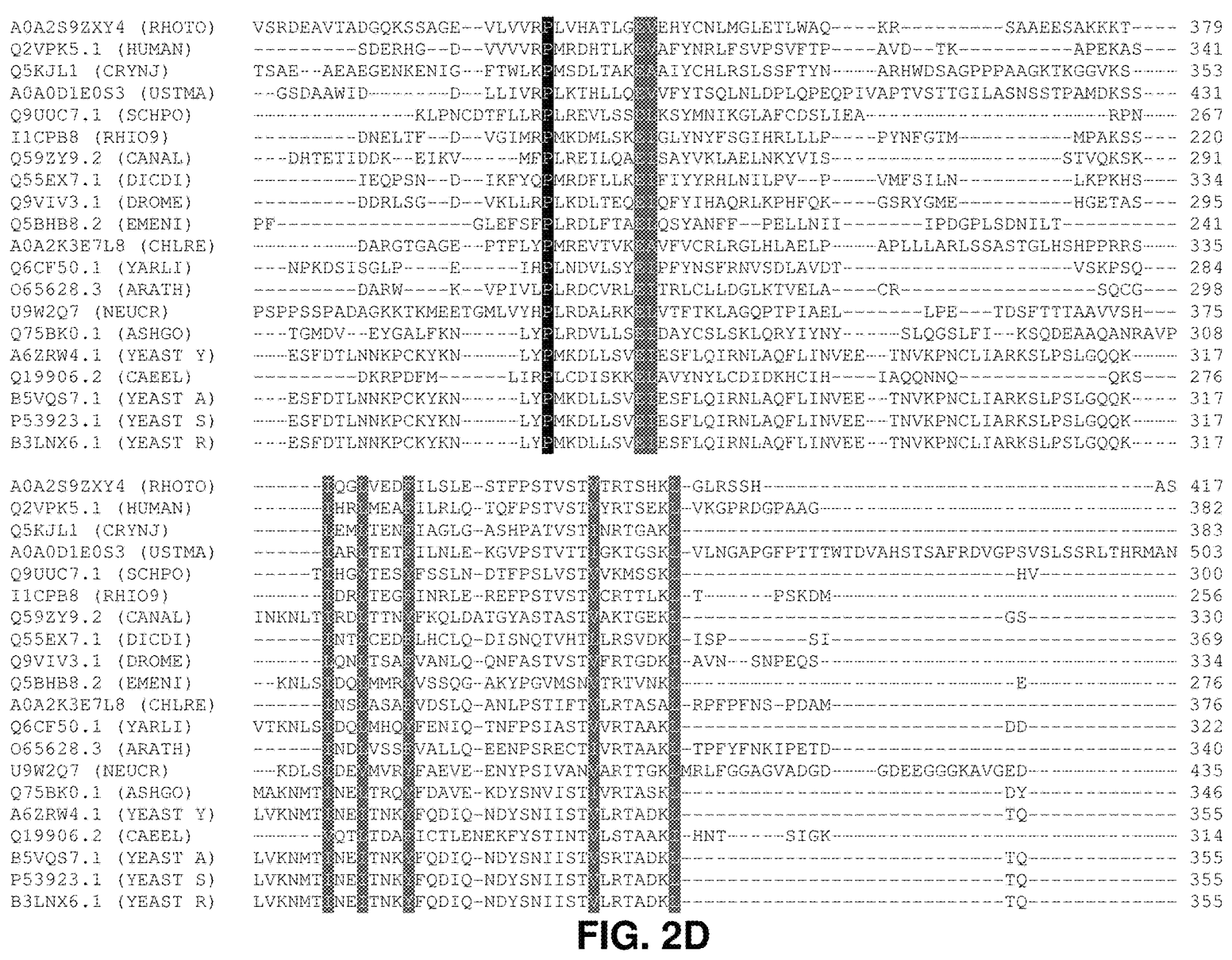
Figure 2E:
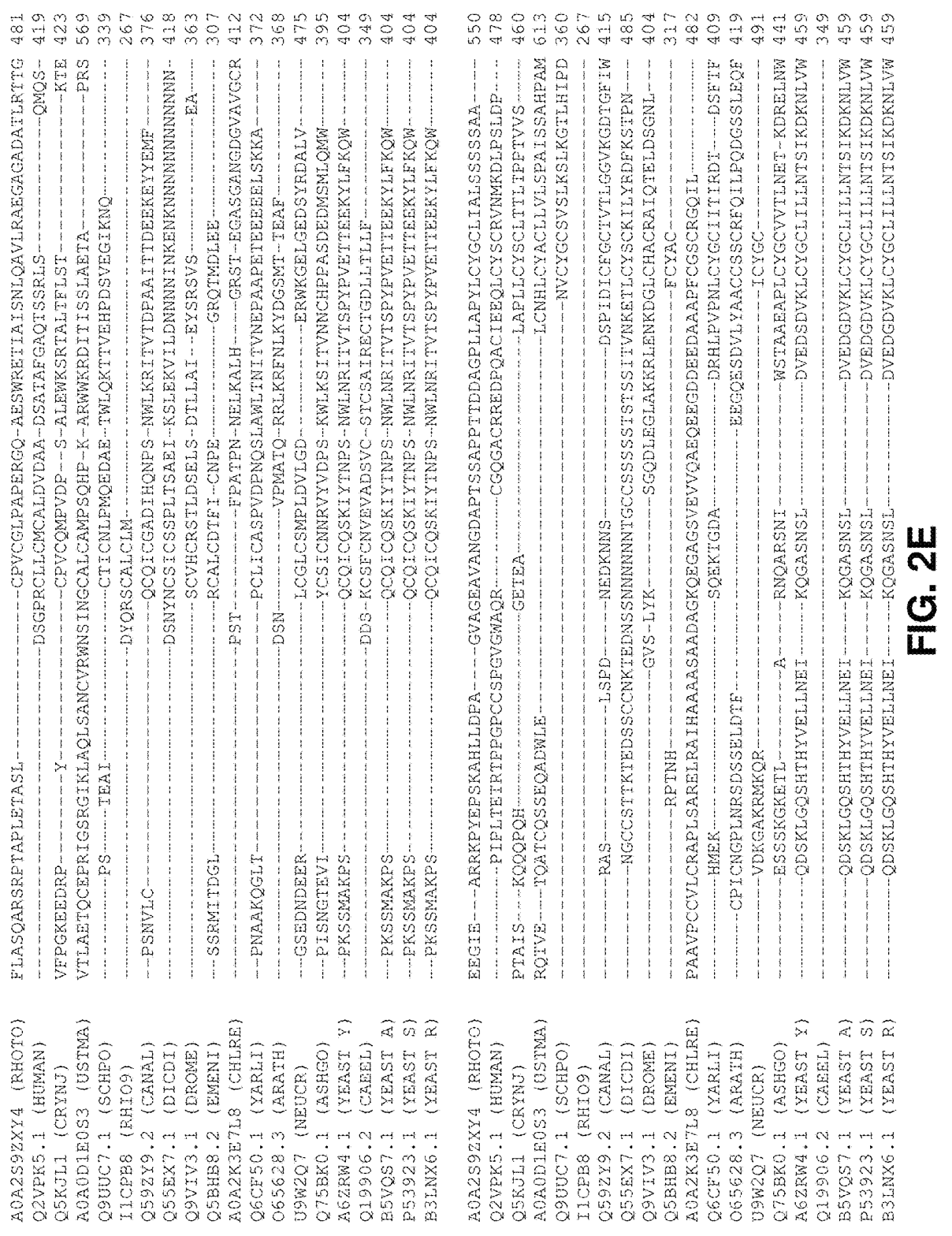

FIGS. 2A-2F show non-limiting amino acid sequences for various cytoplasmic tRNA 2-thiolation protein 2. Provided are sequences for *R. toruloides* (A0A2S9ZXY4 (RHOTO), SEQ ID NO: 1); *H. sapiens* (Q2VPK5.1 (HUMAN), SEQ ID NO: 2); *C. neoromans* (Q5KJL1 (CRYNJ), SEQ ID NO: 3); *U. maydis* (A0A0D1EOS3 (USTMA), SEQ ID NO: 4); *S. pombe* (Q9UUC7.1 (SCHPO), SEQ ID NO: 5); *R. delemar* (I1CPB8 (RHIO9), SEQ ID NO: 6); *C. albicans* (Q59ZY9.2 (CANAL), SEQ ID NO: 7); *D. discoideum* (Q55EX7.1 (DICDI), SEQ ID NO: 8); *D. melanogaster* (Q9VIV3.1 (DROME), SEQ ID NO: 9); *E. nidulans* (Q5BHB8.2 (EMENI), SEQ ID NO: 10); *C. reinhardtii* (A0A2K3E7L8 (CHLRE), SEQ ID NO: 11); *Y. lipolytica* (Q6CF50.1 (YARLI), SEQ ID NO: 12); *A. thaliana* (O65628.3 (ARATH), SEQ ID NO: 13); *N. crassa* (U9W2Q7 (NEUCR), SEQ ID NO: 14); *Ashbya gossypii* (Q75BK0.1 (ASHGO), SEQ ID NO: 15); *S. cerevisiae* (strain YJM789) (Baker's yeast) (A6ZRW4.1 (YEAST Y), SEQ ID NO: 16); *C. elegans* (Q19906.2 (CAEEL), SEQ ID NO: 17); *S. cerevisiae* (strain AWRI1631) (Baker's yeast) (B5VQS7.1 (YEAST A), SEQ ID NO: 18); *S. cerevisiae* (strain ATCC 204508/S288c) (Baker's yeast) (P53923.1 (YEAST S), SEQ ID NO: 19); and *S. cerevisiae* (strain RM11-1a) (Baker's yeast) (B3LNX6.1 (YEAST R), SEQ ID NO: 20).

Figure 3A:
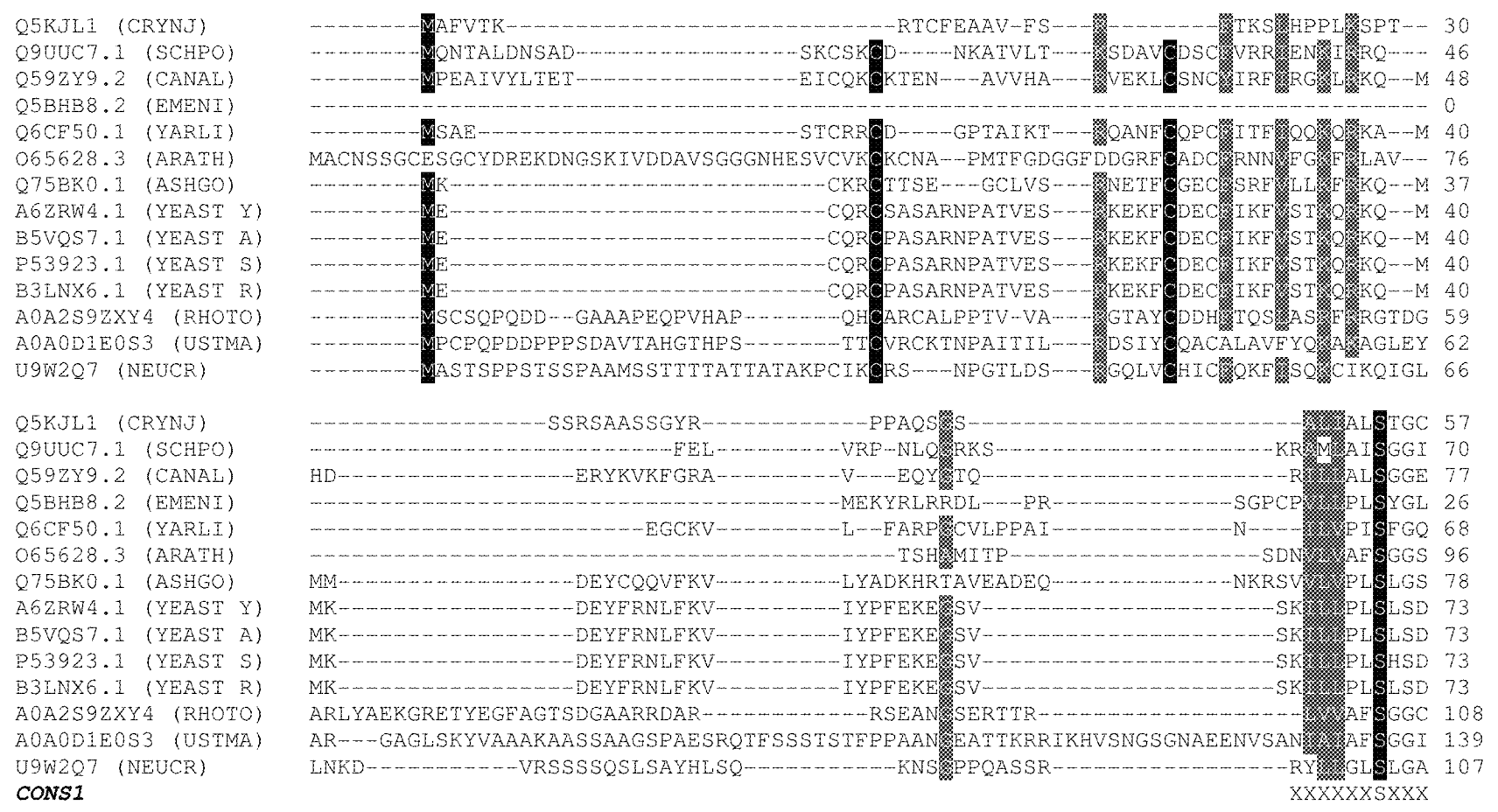
Figure 3B:
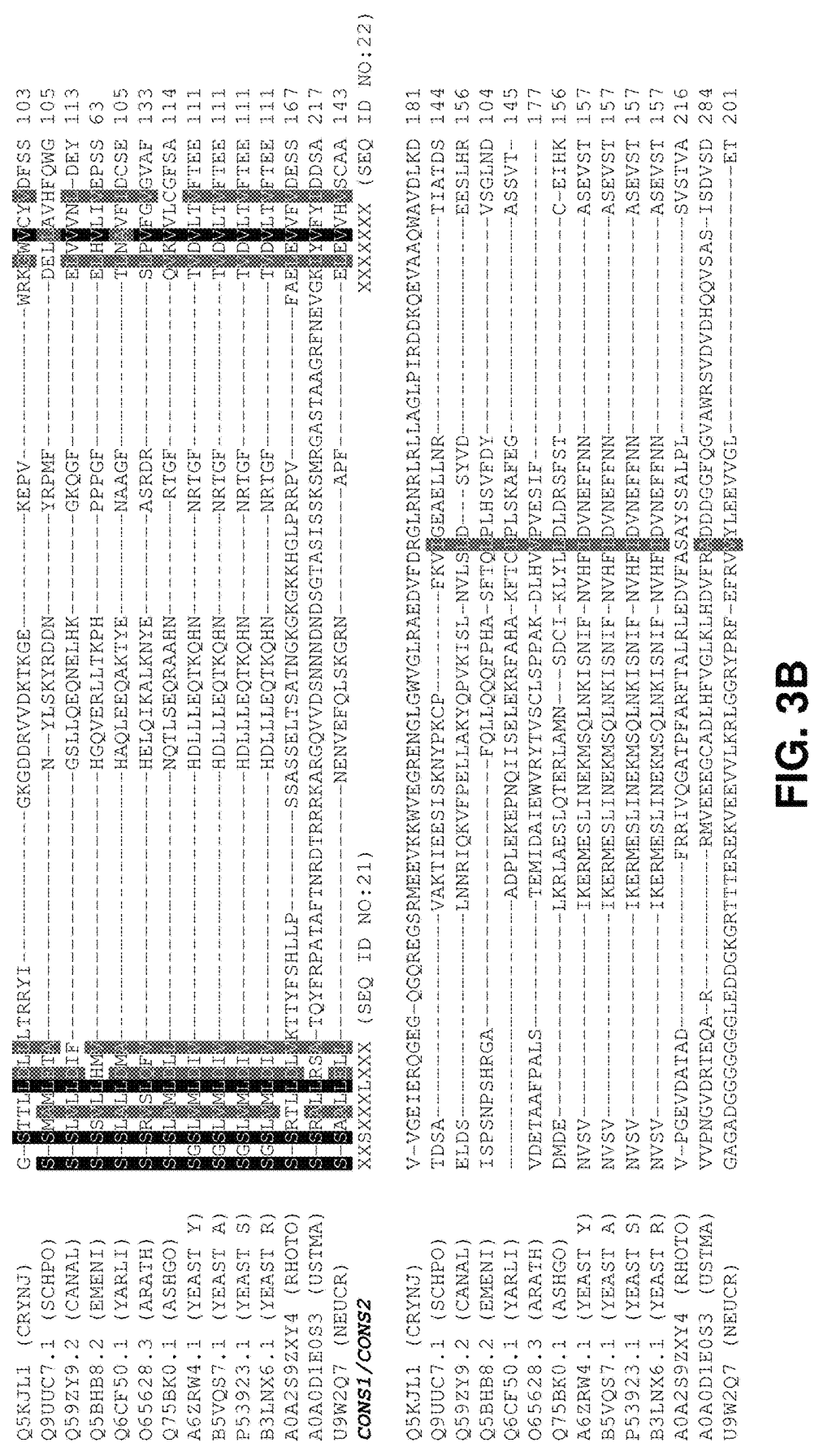
Figure 3C:
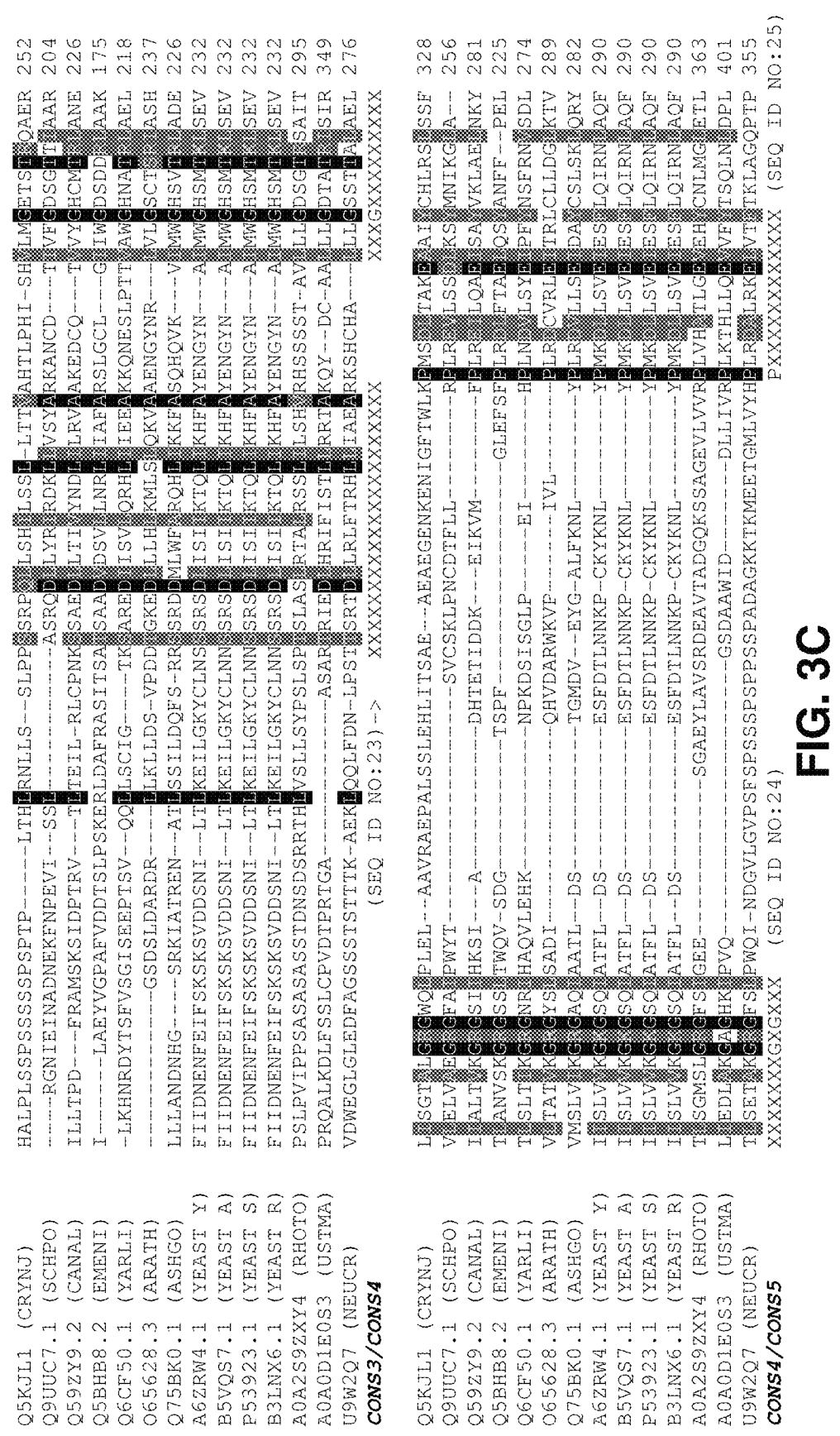
Figure 3D:
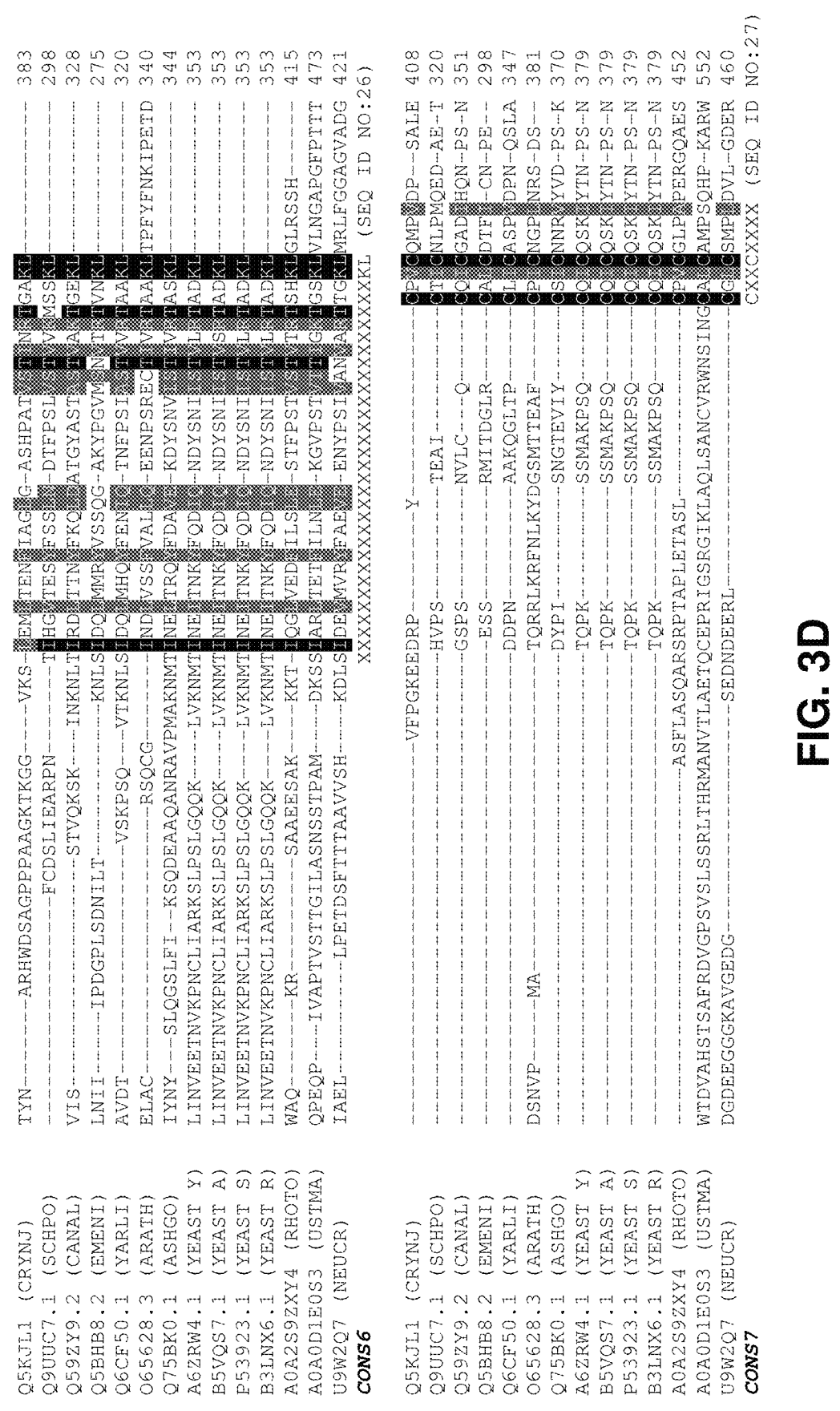

FIGS. 3A-3F show non-limiting amino acid sequences for various cytoplasmic tRNA 2-thiolation protein 2. Provided are sequences for *C. neoromans* (Q5KJL1 (CRYNJ), SEQ ID NO: 3); *S. pombe* (Q9UUC7.1 (SCHPO), SEQ ID NO: 5); *C. albicans* (Q59ZY9.2 (CANAL), SEQ ID NO: 7); *E. nidulans* (Q5BHB8.2 (EMENI), SEQ ID NO: 10); *Y. lipolytica* (Q6CF50.1 (YARLI), SEQ ID NO: 12); *A. thaliana* (O65628.3 (ARATH), SEQ ID NO: 13); *A. gossypii* (Q75BK0.1 (ASHGO), SEQ ID NO: 15); *S. cerevisiae* (strain YJM789) (Baker's yeast) (A6ZRW4.1 (YEAST Y), SEQ ID NO: 16); *S. cerevisiae* (strain AWRI1631) (Baker's yeast) (B5VQS7.1 (YEAST A), SEQ ID NO: 18); *S. cerevisiae* (strain ATCC 204508/S288c) (Baker's yeast) (P53923.1 (YEAST S), SEQ ID NO: 19); *S. cerevisiae* (strain RM11-1a) (Baker's yeast) (B3LNX6.1 (YEAST R), SEQ ID NO: 20); *R. toruloides* (A0A2S9ZXY4 (RHOTO), SEQ ID NO: 1); *U. maydis* (A0A0D1EOS3 (USTMA), SEQ ID NO: 4); and *N. crassa* (U9W2Q7 (NEUCR), SEQ ID NO: 14). Also provided are consensus sequences, including CONS1 (SEQ ID NO: 21), CONS2 (SEQ ID NO: 22), CONS3 (SEQ ID NO: 23), CONS4 (SEQ ID NO: 24), CONS5 (SEQ ID NO: 25), CONS6 (SEQ ID NO: 26), CONS7 (SEQ ID NO: 27), and CONS8 (SEQ ID NO: 28). In another embodiment, for each consensus sequence (SEQ ID NOs: 21-28), each X at each position is an amino acid (or a modified form thereof) that is provided in an aligned reference sequence. For instance, this X can be any amino acid provided in an aligned reference sequence (e.g., aligned reference sequences SEQ ID NOs: 1-20 or SEQ ID NOs: 1, 3-5, 7, 10, 12-16, and 18-20 for the consensus sequence in one of SEQ ID NOs: 21-28). A black background indicates a conserved amino acid, a gray background indicates a similar amino acid, and a dash indicates an absent amino acid.

FIGS. 4A-4G show non-limiting amino acid sequences for (A) acetyl-CoA carboxylase 1 (ACC1) for *R. toruloides* (SEQ ID NO: 30), (B) lysophospholipid acyltransferase (ALE1) for *R. toruloides* (SEQ ID NO: 31), (C) fatty alcohol oxidase (FAO1) for *R. toruloides* (SEQ ID NO: 32), (D) aldehyde dehydrogenase (HFD1) for *R. toruloides* (SEQ ID NO: 33), (E) isocitrate dehydrogenase (IDH) for *R. toruloides* (SEQ ID NO: 34), (F) pyruvate decarboxylase (PDC) for *R. toruloides* (SEQ ID NO: 35), and (G) aldehyde dehydrogenase (ALD) for *R. toruloides* (SEQ ID NO: 36).

FIG. 5 shows a non-limiting pathway to provide a fatty alcohol (FOH).

Figure 6:
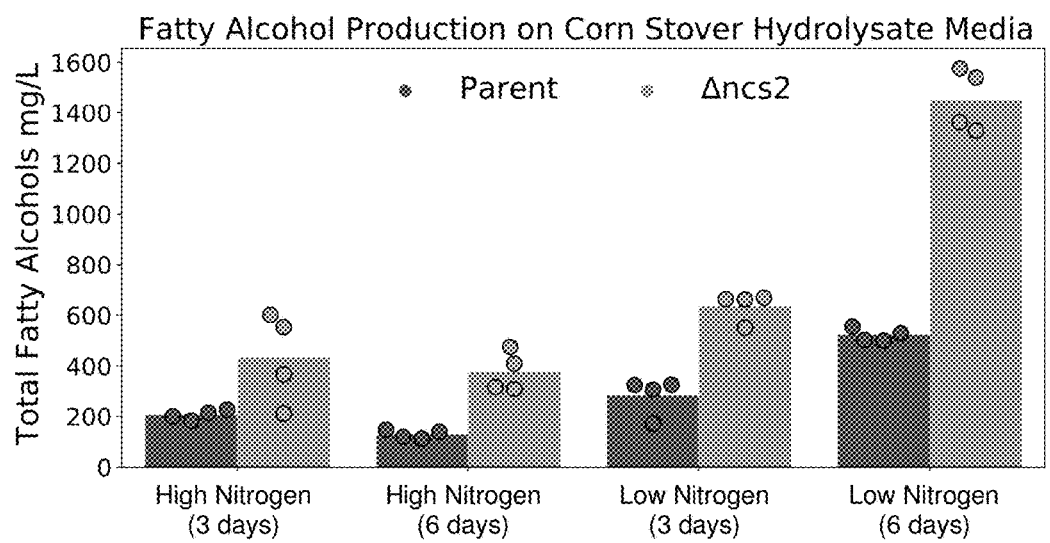

FIG. 6 shows fatty alcohol production in the Ancs2 strain versus a parent strain. The total fatty alcohol content was measured by GC-FID (gas chromatography-flame ionization detection).

Figure 7A:
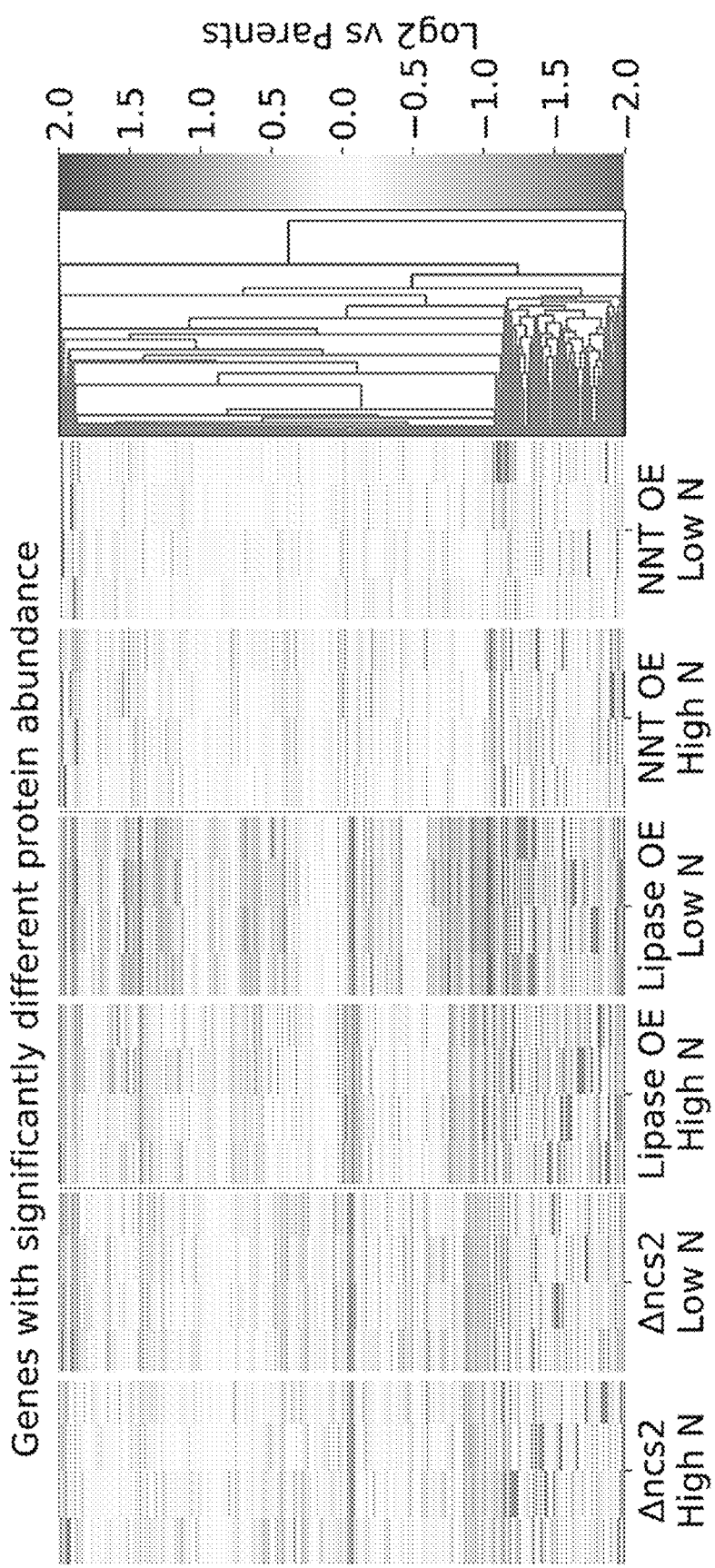
Figure 7B:
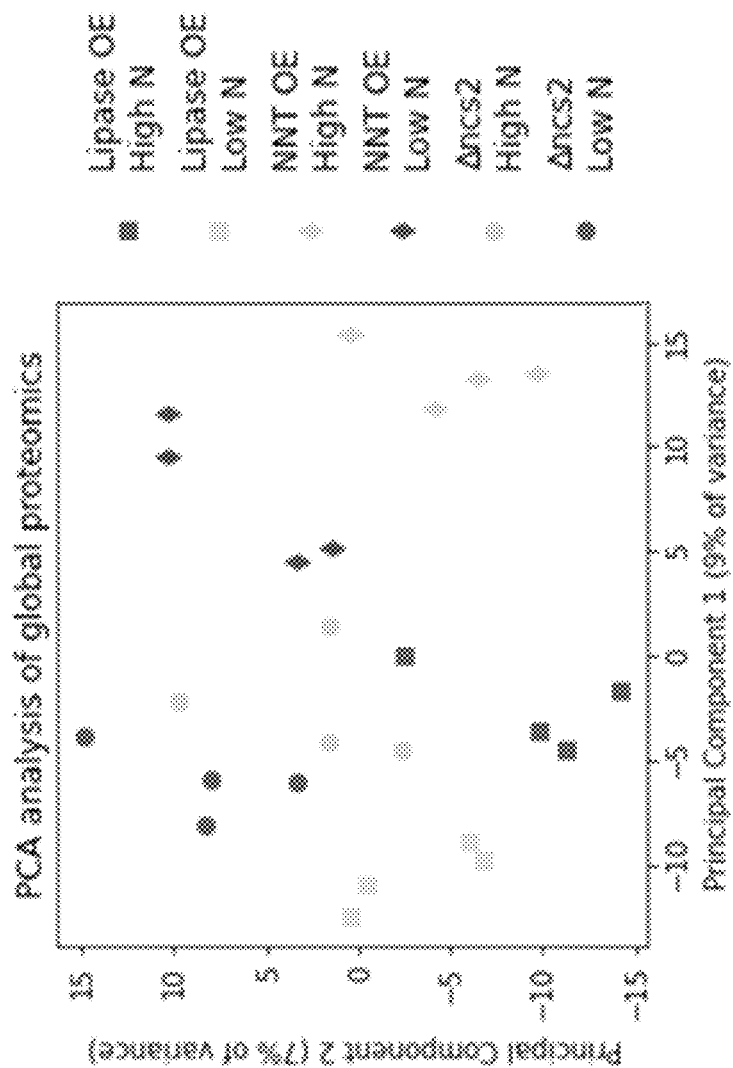

FIGS. 7A-7B show (A) hierarchical clustering of 883 proteins with significantly altered abundance (P value <0.5, fold change > two-fold between mutant and parent strains in at least one condition). Provided are data for a strain having deletion of the ncs2 gene (identified as "Ancs2"), a strain having over expression of a lipase (identified as "Lipase OE"), and a strain having over expression of NNT transhydrogenase (identified as "NNT OE"). Conditions include a high nitrogen (about 5 g/L) or a low nitrogen (about 1 g/L) environment. Also provided are (B) principal component analysis (PCA) of global proteomics.

Figure 8:
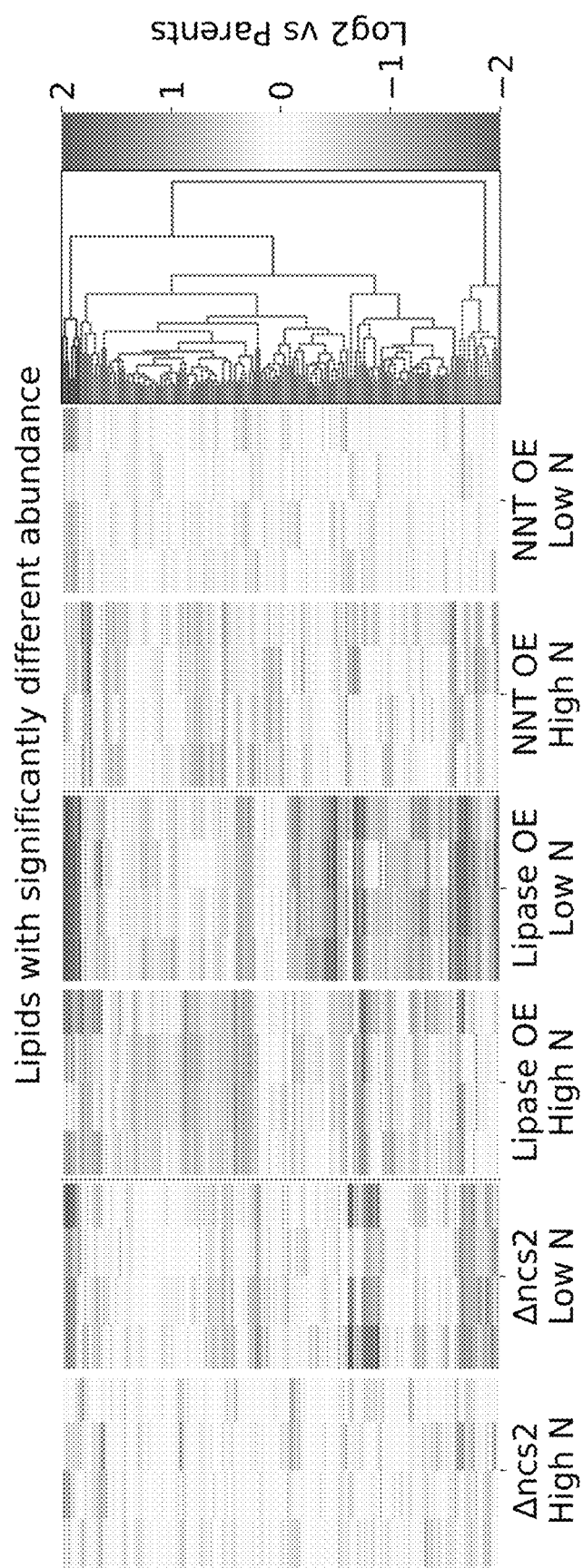

FIG. 8 shows hierarchical clustering of 165 lipids with significantly altered abundance (P value <0.5, at least 25% difference between mutant and parent strains in at least one condition). Provided are data for a strain having deletion of the ncs2 gene (identified as "Ancs2"), a strain having over expression of a lipase (identified as "Lipase OE"), and a strain having over expression of NNT transhydrogenase (identified as "NNT OE"). Conditions include a high nitrogen (about 5 g/L) or a low nitrogen (about 1 g/L) environment.

Figure 9:
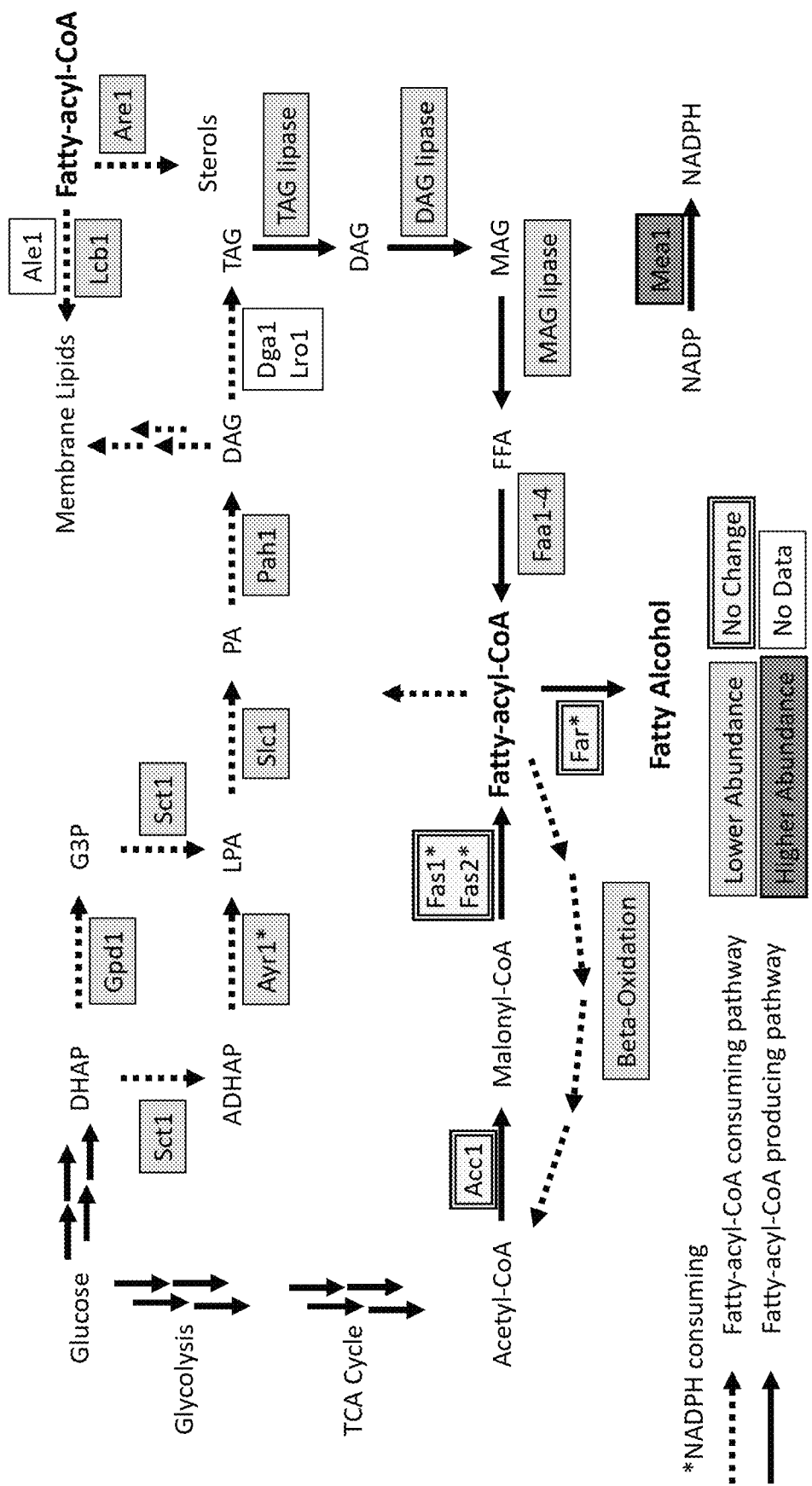
Figure 10A:
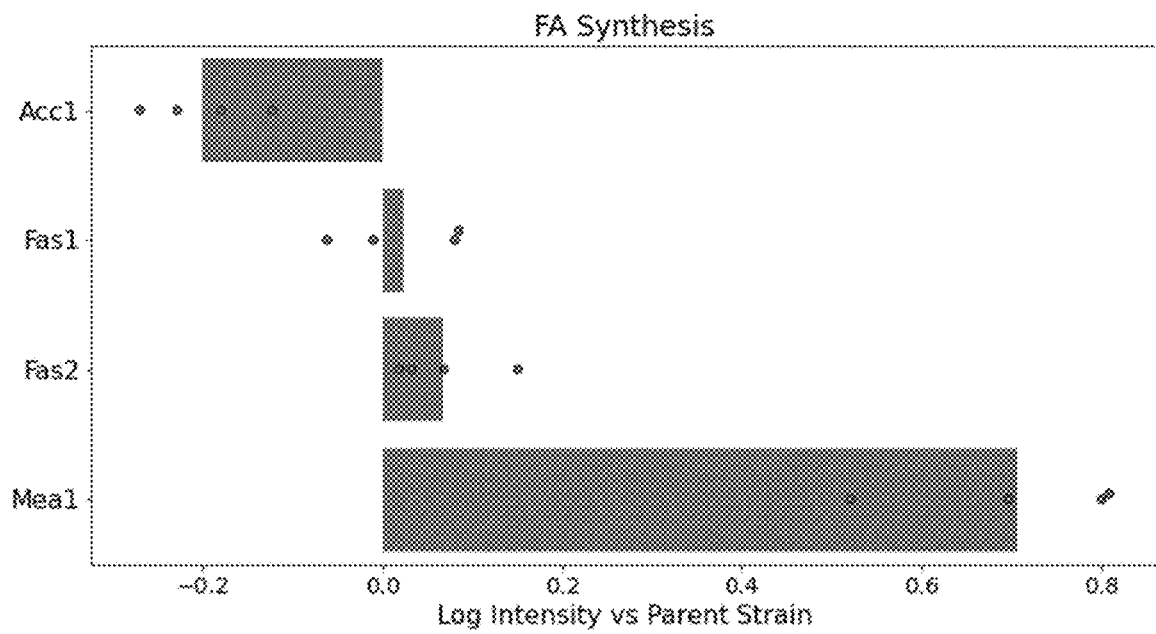
Figure 10B:
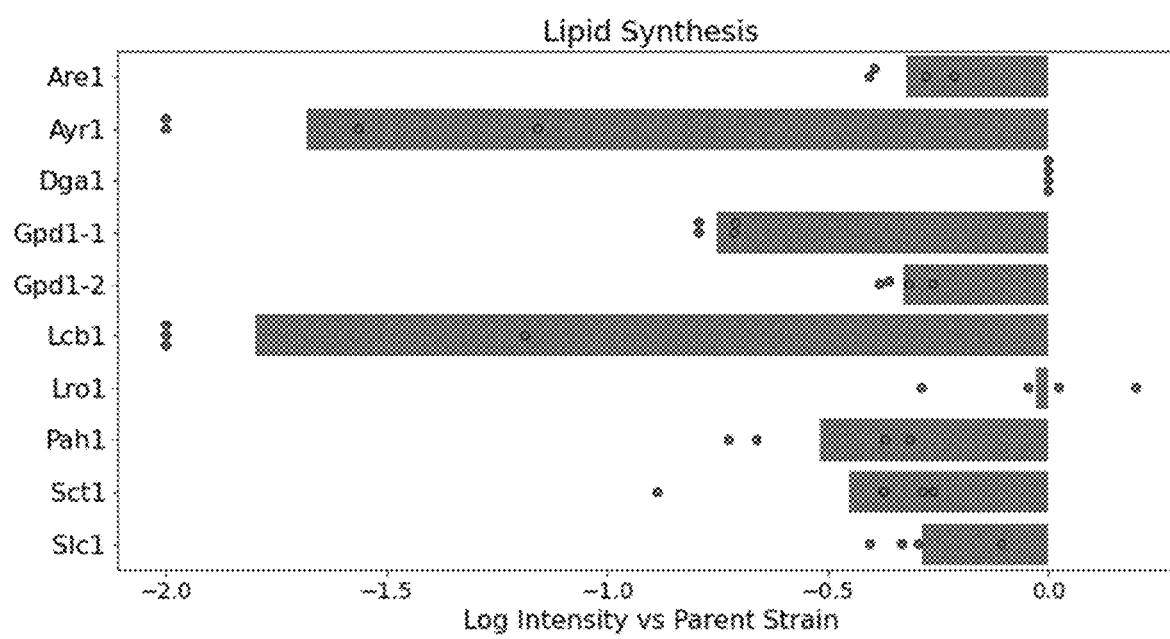
Figure 10C:
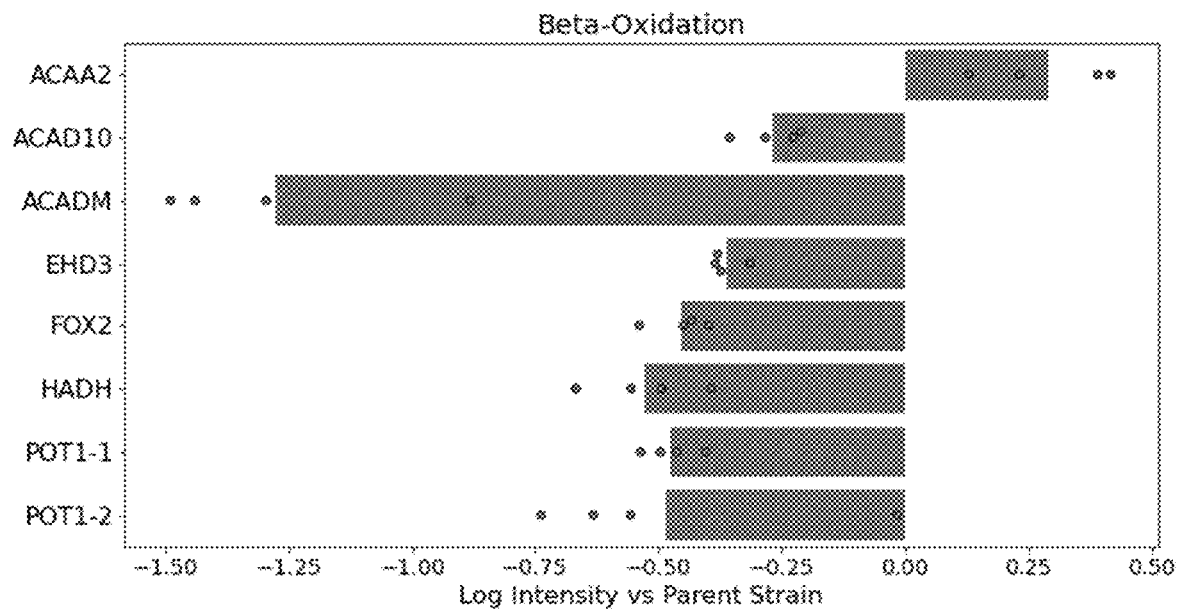
Figure 10D:
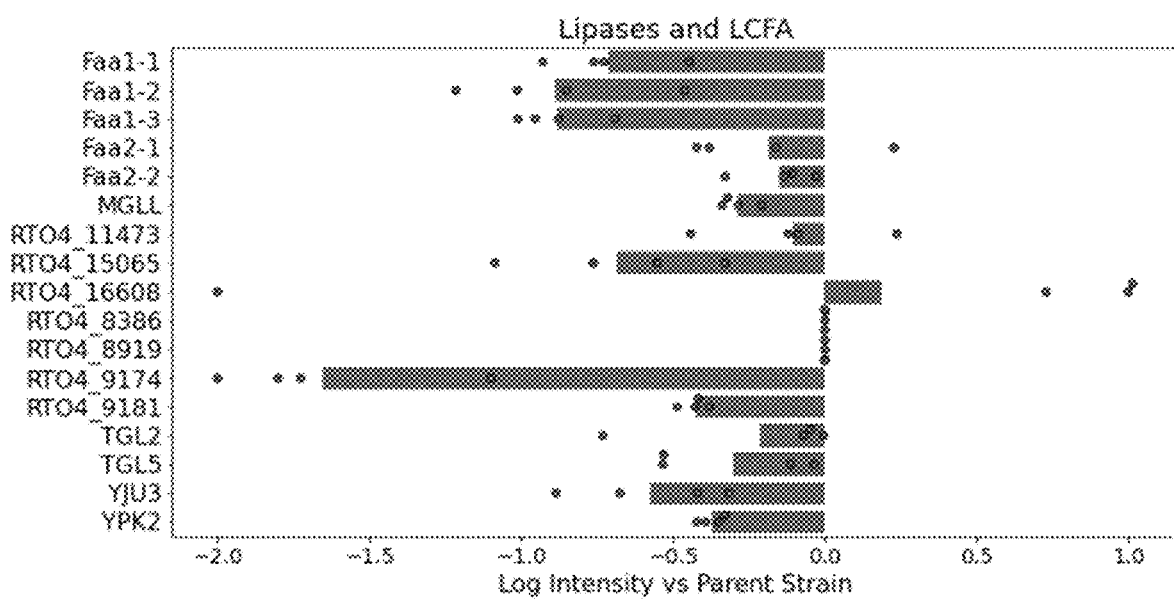

FIG. 9 shows a non-limiting pathway showing synergistic effects of the Ancs2 mutation on competing pathways for fatty-acyl-CoA.

FIGS. 10A-10D show relative abundance of proteins from pathways shown in FIG. 9 in the Ancs2 mutant versus the parental strain by global proteomics. Provided are graphs showing log base 2 ratios of total protein intensities for (A)

proteins related to fatty-acyl-CoA synthesis; (B) proteins related to lipid synthesis; (C) proteins related to beta oxidation; and (D) proteins related to lipases and long chain fatty acids (LCFA).

Figure 11:
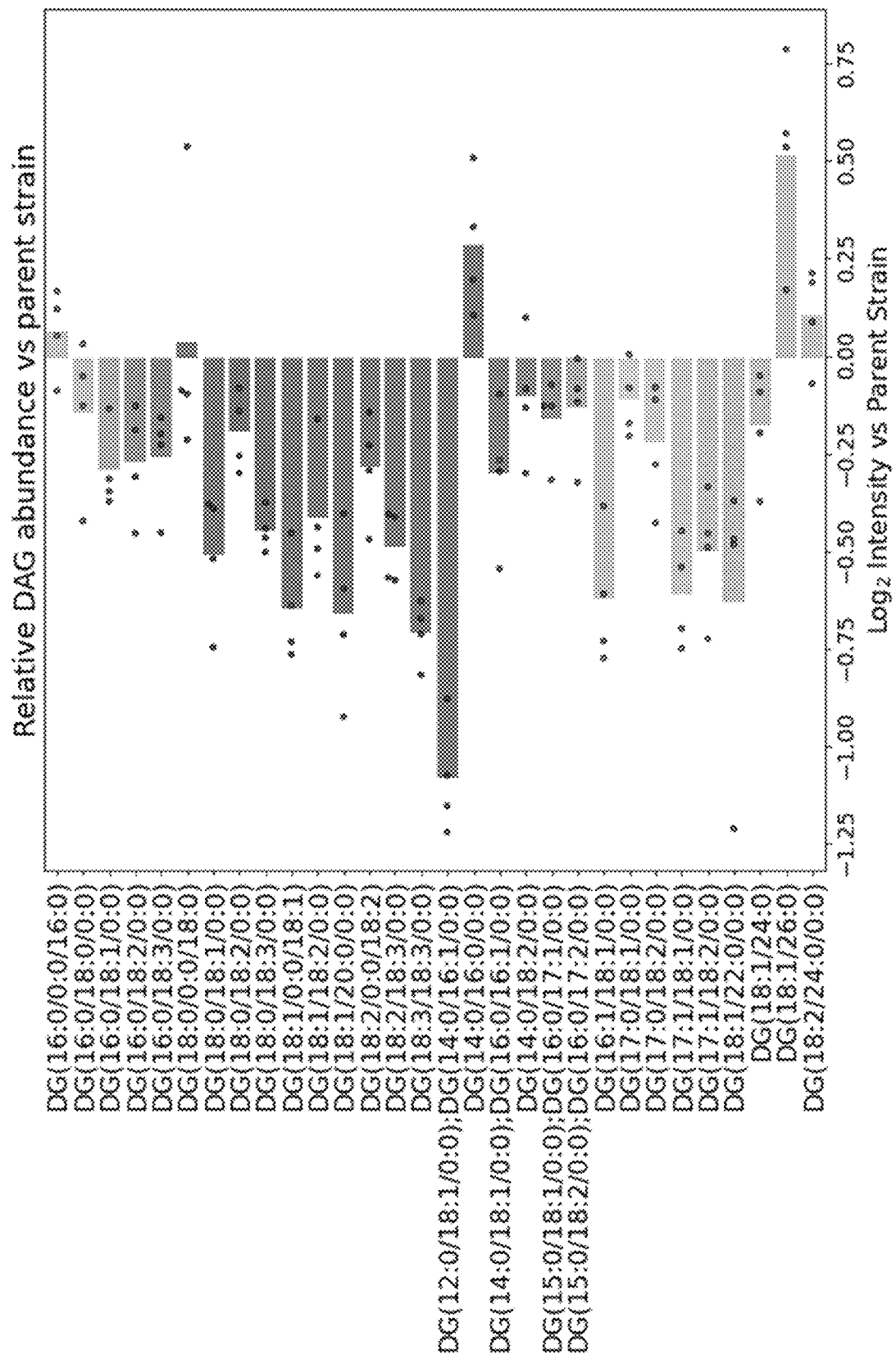

FIG. 11 shows relative abundance of diacylglycerol species in a Ancs2 mutant versus the parent strain as determined by global proteomics.

Figure 12:
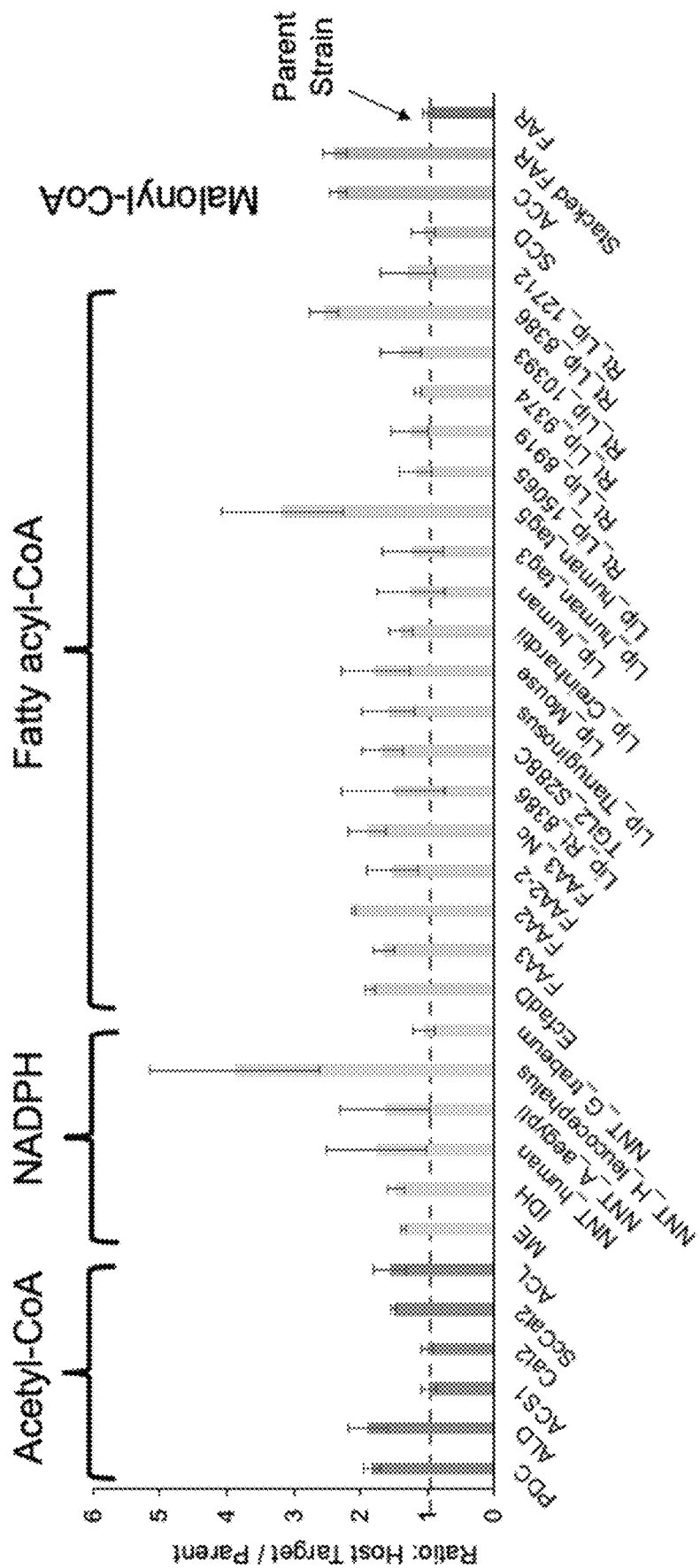

FIG. 12 shows fatty alcohol (FOH) production in various strains that overexpress particular target genes.

Figure 13:
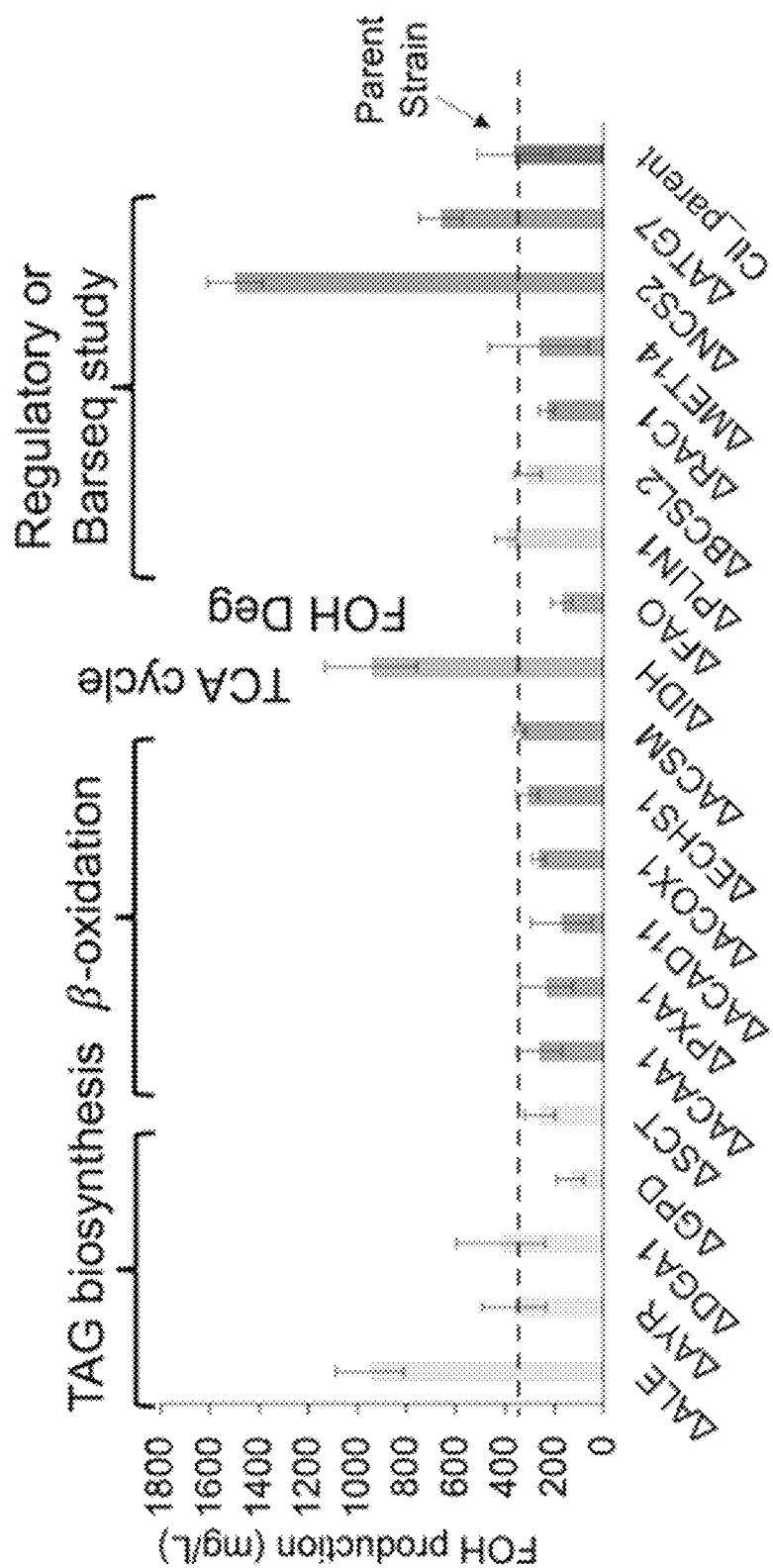

FIG. 13 shows fatty alcohol (FOH) production in various knock-out strains that lack particular target genes.

Figure 14:
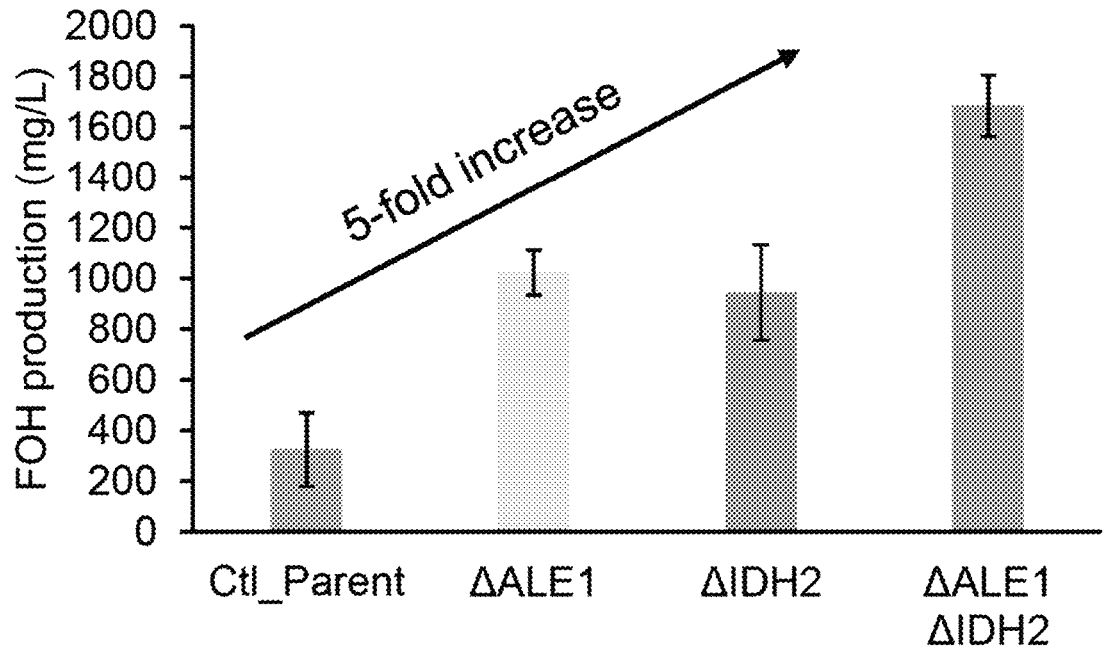

FIG. 14 shows fatty alcohol (FOH) production in single knock-out strains (ΔALE1 or ΔIDH2) and a multi-knock-out strain (ΔALE1 and ΔIDH2), as compared to the control parental strain.

Figure 15:
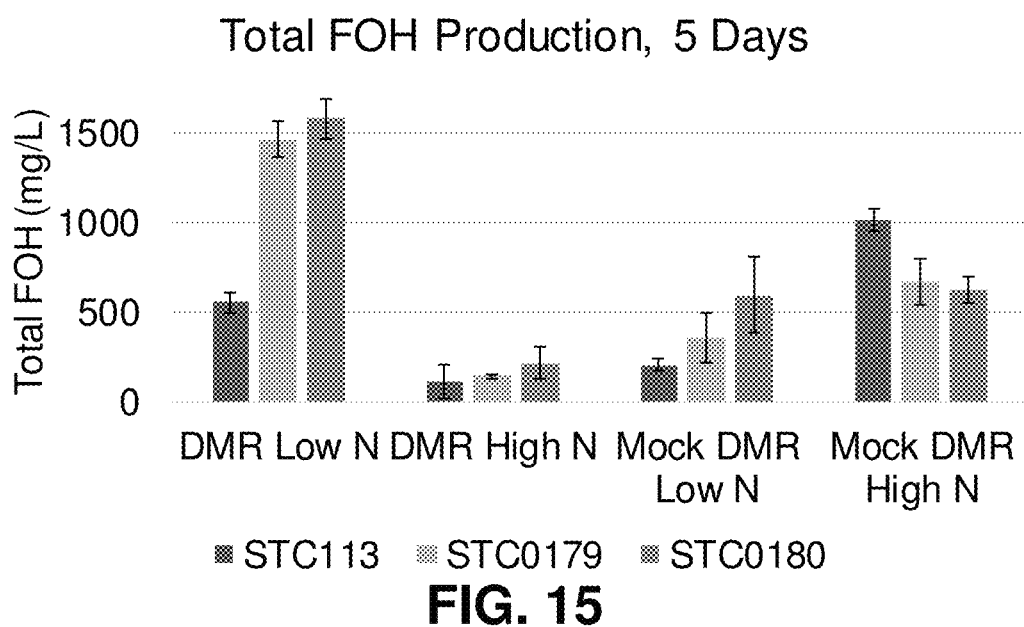

FIG. 15 shows the effect of culture conditions of fatty alcohol (FOH) production for the NCS2 mutant strain (indicated as "STC0179" and "STC0180") and its parental strain (indicated as "STC0113").

Figure 16A:
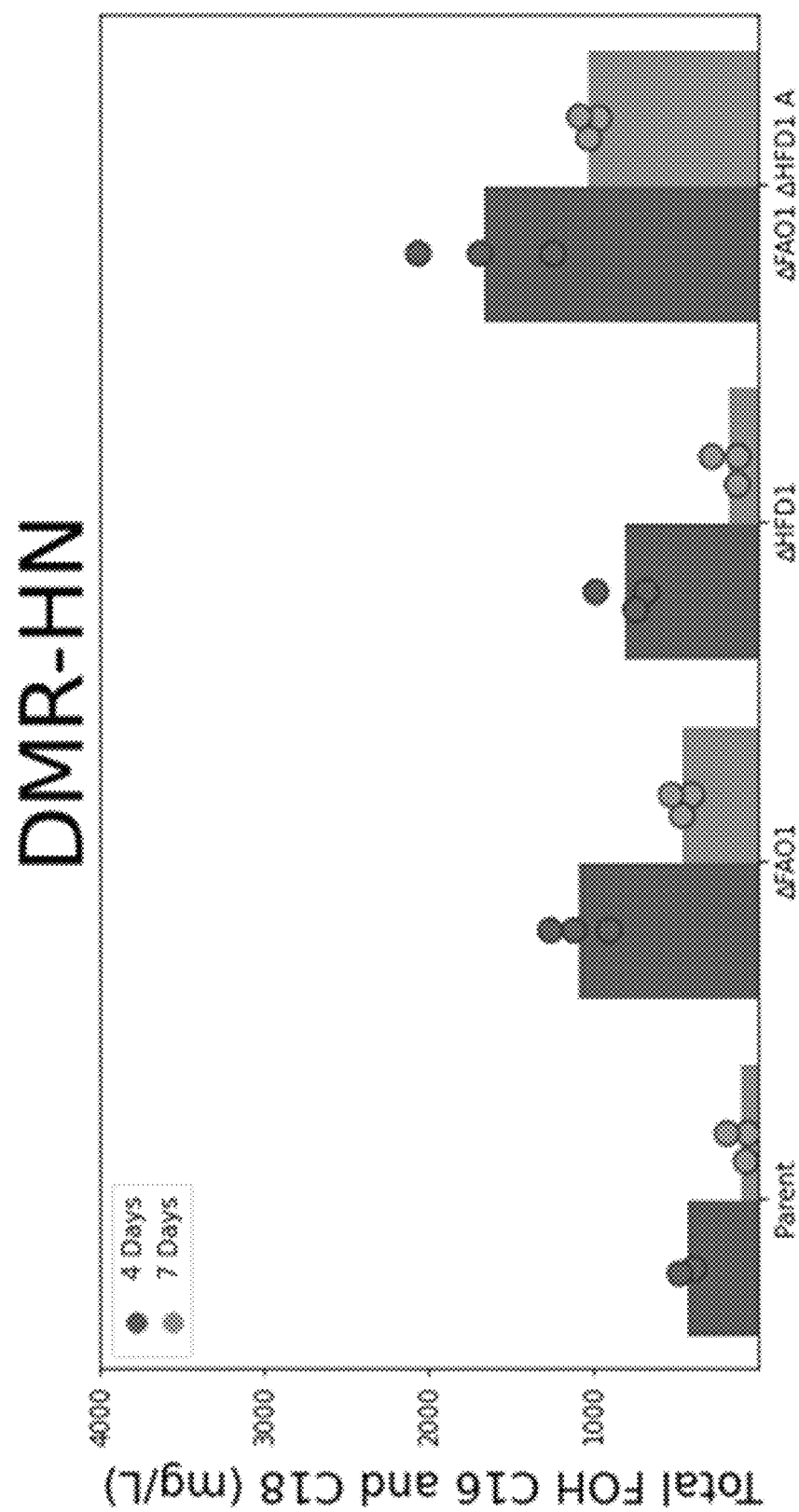
Figure 16B:
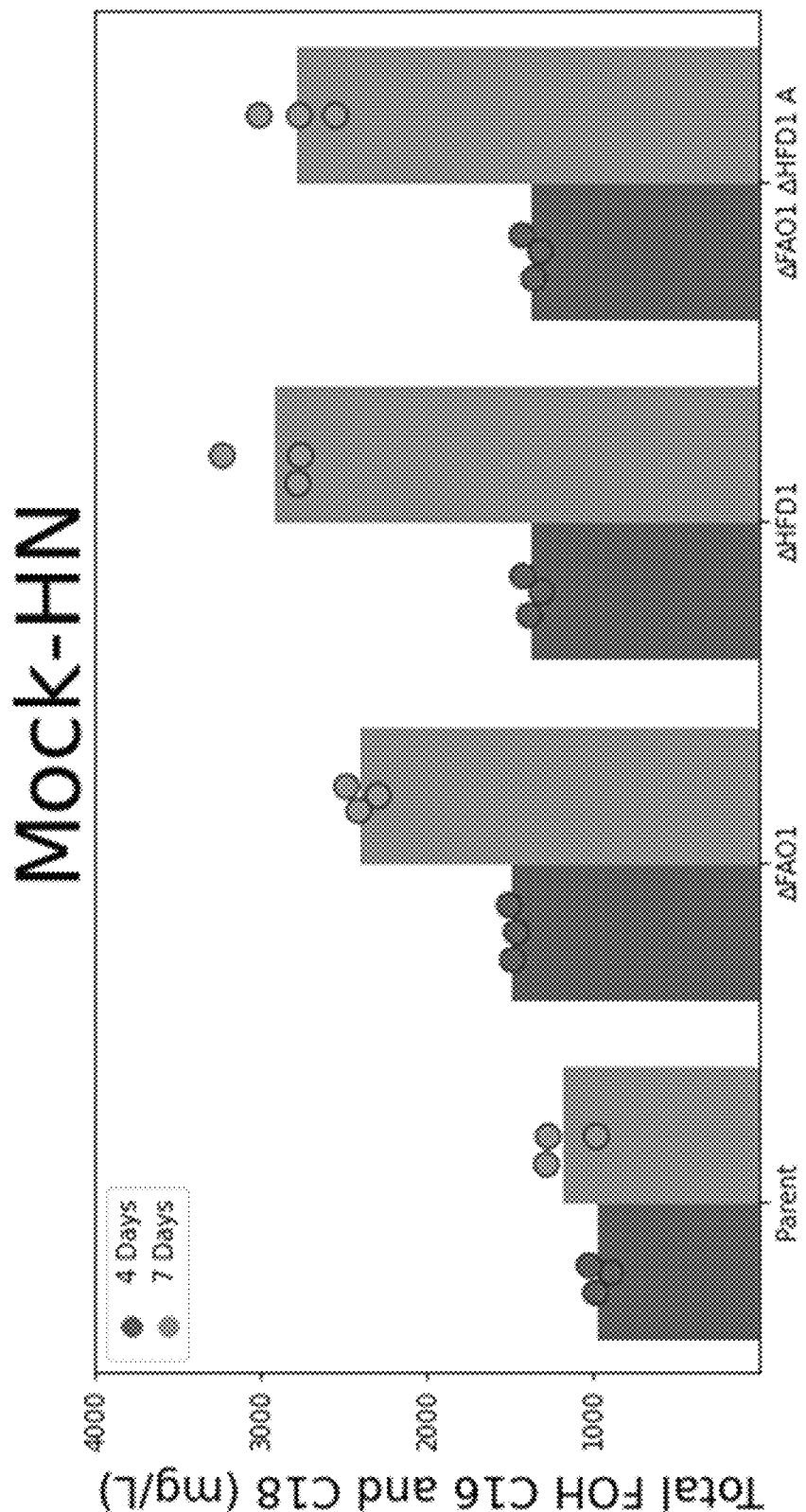

FIGS. 16A-16B show C16 and C18 fatty alcohol (FOH) production in single knock-out strains (ΔFAO1 or ΔHFD1) or a multi-knock-out strain (ΔFAO1 and ΔHFD1), as compared to the control parental strain. Provided are data for corn stover hydrolysate media (indicated as "DMR") and for a defined media (indicated as "Mock") under high nitrogen (HN) conditions (5 g/L ammonium sulfate).

Figure 17A:
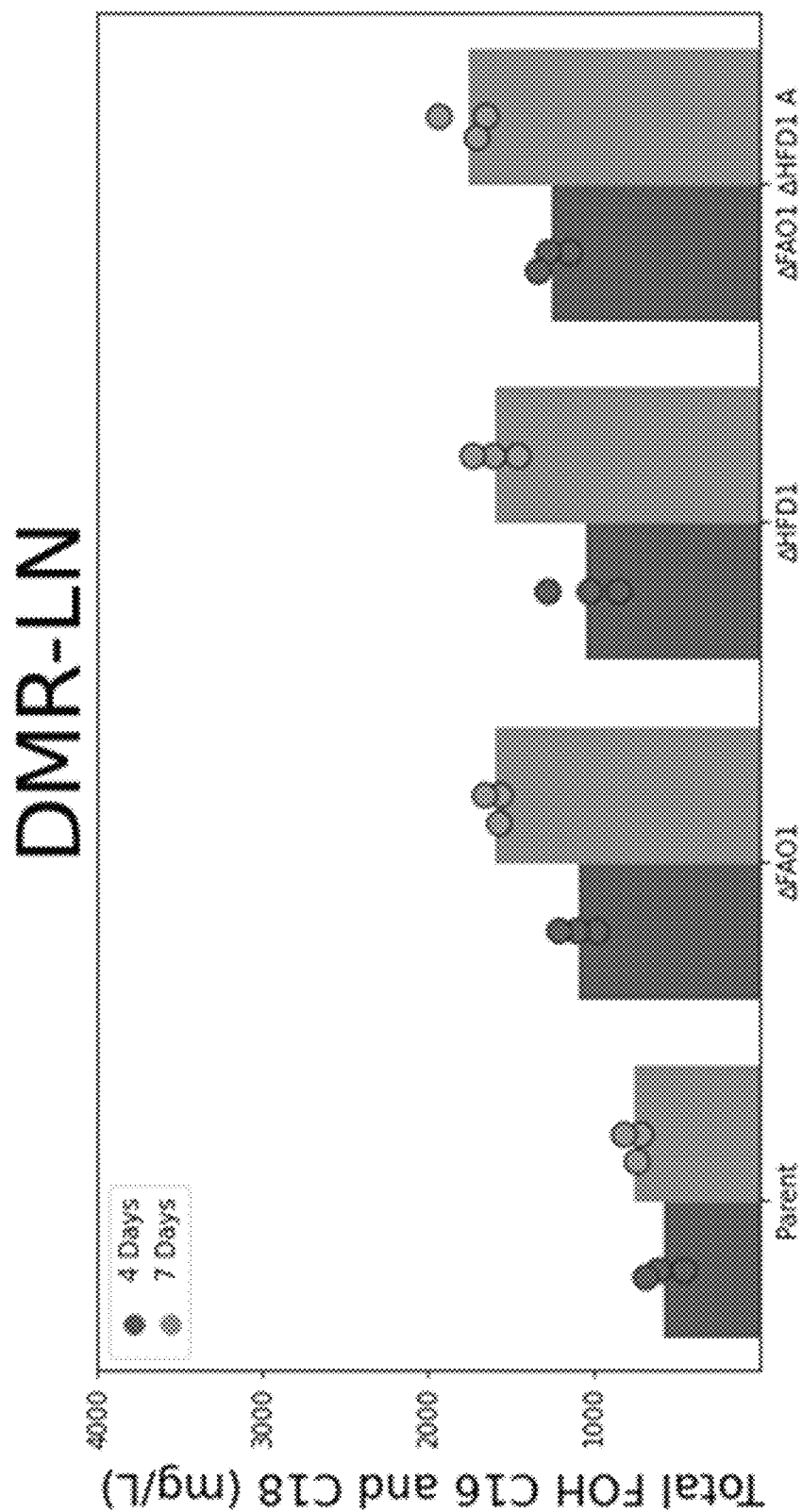
Figure 17B:
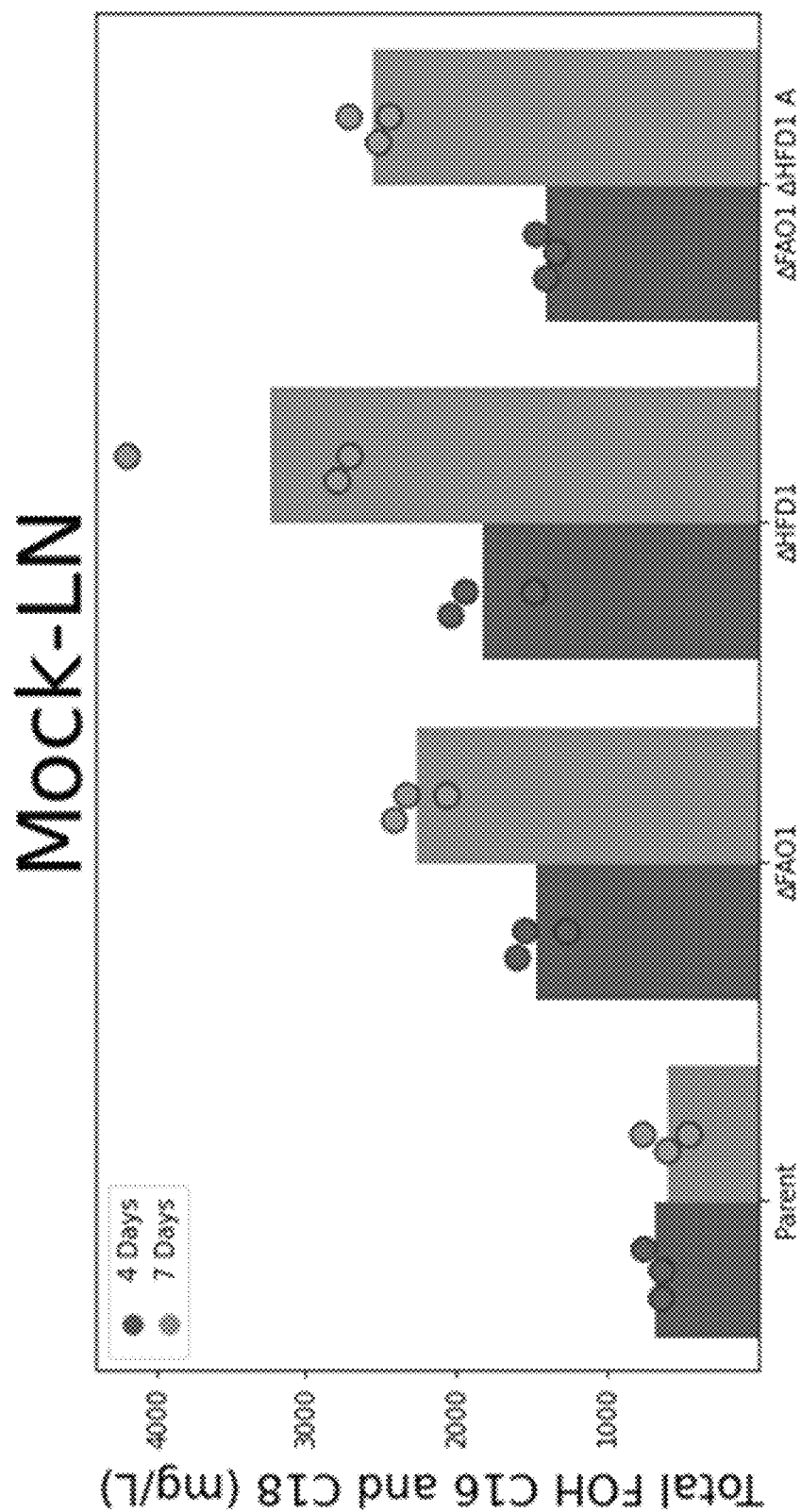

FIGS. 17A-17B show C16 and C18 fatty alcohol (FOH) production in single knock-out strains (ΔFAO1 or ΔHFD1) or a multi-knock-out strain (ΔFAO1 and ΔHFD1), as compared to the control parental strain. Provided are data for corn stover hydrolysate media (indicated as "DMR") and for a defined media (indicated as "Mock") under low nitrogen (LN) conditions (1 g/L ammonium sulfate).

DETAILED DESCRIPTION

The present disclosure relates to host cells having one or more mutant genes. In one embodiment, the mutant gene includes a target gene related to a tRNA thiolation protein (e.g., the ncs2 gene). Such host cells can be used to produce lipid-derived compounds, such as fatty alcohols.

In some non-limiting embodiments, the tRNA thiolation protein is the ncs2 gene, which plays a role in 2-thiolation of tRNA. Without wishing to be limited by mechanism, the modification of tRNA wobble positions (e.g., by way of thiolation) has been implicated in regulation of gene expression in response to heat shock, but the overall effect of this metabolic modification is unclear. In culture, the ncs2 deletion (Ancs2) mutant provides overall reduced lipid content. However, surprising, the same mutant also provide overall increased fatty alcohol (FOH) content. In some embodiments, the deletion of ncs2 resulted in at least a two- to three-fold increase in FOH production over the parent strain.

This observation is supported by combined metabolomic, proteomic, and lipidomic analysis, as described herein. This analysis shows a global shift in lipid and proteomic profiles in the Ancs2 mutant with decreased flux from fatty-acyl-CoA to storage lipids (e.g., thereby providing reduced fatty-acyl-CoA incorporation into diacylglycerides), reduced fatty-acyl-CoA consumption by beta-oxidation, and increased fatty-acyl-CoA production through higher expression of malic enzyme (NADPH generating). In some embodiments, deletion of ncs2 coordinately reduces the expression of several enzymes essential for triacylglycerides biosynthesis, while maintaining fatty-acyl-CoA production.

To investigate how various mutants with altered lipid accumulation might enhance or inhibit production of fatty-acyl-CoA derived chemicals, deletion mutants for several genes identified in a functional genomic screen of R. toruloides were created in a fatty alcohol producing strain expressing fatty acyl-CoA reductase for Marinobacter aquaeolei. In particular embodiments, the Ancs2 mutant include one or more further mutant genes. In particular embodiments, the further mutant gene includes deletion or overexpression of proteins that provides low FOH catabolism and/or low re-importation of secreted FOH. Overexpression can include random or targeted integration of the gene to be expressed.

Accordingly, the host cell can include any useful mutant having a mutant gene encoding a cytoplasmic tRNA thiolation protein. The mutant gene can include deletion of the gene that encodes the cytoplasmic tRNA protein or modification of that gene that results in lower expression of the NCS2 protein. In one embodiment, the host cell include a ncs2 gene deletion or a ncs2 gene modification, which results in lowered expression of the NCS2 protein. The ncs2 gene or NCS2 protein can include any provided herein, such as homologs. For instance, FIG. 1A provides an unrooted phylogenetic tree of NCS2 homologs in model eukaryotic species. The NCS2 protein for R. toruloides is provided in FIG. 1B (SEQ ID NO: 1).

Further non-limiting amino acid sequences for various NCS2 proteins are provided in FIGS. 2A-2F (SEQ ID NOs: 1-20). In some embodiments, the host cell includes a mutant gene encoding a cytoplasmic tRNA thiolation protein, in which the protein includes a polypeptide sequence having at least 90% sequence identity to one of SEQ ID NOs: 1-20. In particular embodiments, the mutant gene includes deletion of the gene encoding the cytoplasmic tRNA thiolation protein. In other embodiments, the mutant gene includes lower expression or under expression of the gene encoding the cytoplasmic tRNA thiolation protein.

The NCS2 protein can also be characterized by one or more consensus sequences. In one embodiment, NCS2 protein has one or more consensus sequences provided as SEQ ID NOs: 21-28 (FIGS. 3A-3F). In some embodiments, the host cell includes a mutant gene encoding a cytoplasmic tRNA thiolation protein, in which the protein includes a polypeptide sequence having at least 90% sequence identity to one or more of the following SEQ ID NOs: 21-28.

In one embodiment, protein includes a polypeptide sequence having at least 90% sequence identity to SEQ ID NO: 21:

$X_1X_2X_3X_4X_5X_6SX_8X_9X_{10}X_{11}X_{12}SX_{14}X_{15}X_{16}LX_{18}X_{19}X_{20}$, wherein:

$X_1$ is A, V, I, L, R, H, K, P, N, Q, or absent;
each of $X_2$, $X_6$, and $X_{20}$ is, independently, A, V, I, L, F, Y, or W;
each of $X_3$, $X_4$, and $X_{16}$ is, independently, A, V, I, L, or M;
$X_5$ is G, A, V, I, L, or P;
$X_8$ is G, A, V, I, L, R, H, K, S, T, F, Y, or W;
each of $X_9$ and $X_{11}$ is, independently, G, C, S, T, or absent;
$X_{10}$ is A, V, I, L, D, E, C, S, T, N, or Q;
$X_{12}$ is G or absent;
$X_{14}$ is A, V, I, L, M, C, S, T, R, H, or K;
$X_{15}$ is A, V, I, L, S, or T;
$X_{18}$ is R, H, K, D, or E; and
$X_{19}$ is A, V, I, L, M, S, T, F, Y, or W.

In one embodiment, protein includes a polypeptide sequence having at least 90% sequence identity to SEQ ID NO: 22:

$X_1X_2X_3X_4X_5X_6X_7$, wherein:

X₁ is G, A, V, I, L, R, H, K, or absent;
X₂ is R, H, K, D, E, S, T, N, or Q;
X₃ is G, A, V, I, L, D, or E;
X₄ is A, V, I, L, R, H, K, D, E, N, Q, P, F, Y, or W;
X₅ is A, V, I, or L;
X₆ is A, V, I, L, C, S, T, F, Y, or W; and
X₇ is G, A, V, I, L, R, H, K, S, T, N, Q, F, Y, or W.

In one embodiment, protein includes a polypeptide sequence having at least 90% sequence identity to SEQ ID NO: 23:

$$X_1X_2X_3X_4X_5X_6X_7X_8X_9X_{10}X_{11}X_{12}X_{13}X_{14}X_{15}X_{16}X_{17}X_{18}X_{19}X_{20}X_{21}, \text{ wherein:}$$

X₁ is any amino acid or absent;
each of X₂, X₇, X₁₅, and X₁₆ is, independently, A, V, I, L, M, S, or T;
X₃ is G, A, V, I, L, R, H, K, S, or T;
X₄ is A, V, I, L, R, H, or K;
X₅ is A, V, I, L, D, E, N, Q, S, T, or P;
X₆ is D, E, N, Q, S, or T;
X₈ is A, V, I, L, D, E, R, H, or K;
each of X₉ and X₂₁ is, independently, A, V, I, L, R, H, K, S, T, F, Y, or W;
X₁₀ is A, V, I, L, R, H, K, F, Y, or W;
X₁₁ is A, V, I, L, F, Y, or W;
X₁₂ is A, V, I, L, R, H, K, N, Q, F, Y, or W;
X₁₃ is D, E, N, Q, S, T, R, H, K, or M;
each of X₁₄ and X₁₈ is, independently, A, V, I, L, D, E, R, H, K, N, Q, S, or T;
X₁₇ is A, V, I, L, R, H, K, N, or Q;
X₁₉ is A, V, I, L, D, E, R, H, K, S, T, F, Y, or W; and
X₂₀ is A, V, I, or L.

In one embodiment, protein includes a polypeptide sequence having at least 90% sequence identity to SEQ ID NO: 24:

$$X_1X_2X_3GX_5X_6X_7X_8X_9X_{10}X_{11}X_{12}X_{13}X_{14}X_{15}X_{16}X_{17}X_{18}X_{19}X_{20}GX_{22}GX_{24}X_{25}X_{26}, \text{ wherein:}$$

each of X₁ and X₂₆ is, independently, A, V, I, or L;
each of X₂, X₁₁, X₁₄, X₁₅, X₁₈, and X₁₉ is, independently, A, V, I, L, M, S, or T;
X₃ is A, V, I, L, M, S, T, F, Y, or W;
X₅ is R, H, K, D, E, S, or T;
X₆ is C, S, T, N, or Q;
each of X₇ and X₁₆ is, independently, G, A, V, I, L, M, D, E, S, or T;
X₈ is D, E, S, or T;
each of X₉ and X₂₂ is, independently, A, V, I, L, R, H, K, S, or T;
X₁₀ is A, V, I, L, N, Q, S, or T;
each of X₁₂ and X₁₇ is, independently, G, A, V, I, L, D, E, N, Q, S, or T;
each of X₁₃ and X₂₀ is, independently, A, V, I, L, R, H, K, D, E, S, or T; and each of X₂₄ and X₂₅ is, independently, A, V, I, L, R, H, K, S, T, N, Q, F, Y, or W.

In one embodiment, protein includes a polypeptide sequence having at least 90% sequence identity to SEQ ID NO: 25:

$$PX_2X_3X_4X_5X_6X_7X_8X_9X_{10}X_{11}X_{12}X_{13}, \text{ wherein:}$$

X₂ is A, V, I, L, M, S, or T;
each of X₃ and X₇ is, independently, A, V, I, L, R, H, K, N, Q, S, or T;
X₄ is R, H, K, D, E, S, or T;
X₅ is A, V, I, L, R, H, K, C, S, or T;
each of X₆ and X₁₃ is, independently, A, V, I, L, S, T, F, Y, or W;
X₈ is any amino acid;

X₉ is D or E;
X₁₀ is A, V, I, or L;
X₁₁ is A, V, I, L, R, H, K, D, E, N, Q, S, T, or P; and
X₁₂ is A, V, I, L, R, H, K, S, T, F, Y, or W.

In one embodiment, protein includes a polypeptide sequence having at least 90% sequence identity to SEQ ID NO: 26:

$$X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}X_{25}X_{26}X_{27}X_{28}$$
$$X_{29}X_{30}KL, \text{ wherein:}$$

each of X₁ and X₂₈ is, independently, M, S, T, or absent;
each of X₂, X₅, and X₂₅ is, independently, A, V, I, or L;
X₃ is A, V, I, L, R, H, K, D, E, N, or Q;
X₄ is G, M, R, H, K, D, E, N, or Q;
each of X₆, X₂₃, and X₂₉ is, independently, G, A, V, I, L, C, M, S, or T;
each of X₇, X₁₁, X₁₆, and X₃₀ is, independently, G, A, V, I, L, M, R, H, K, D, E, N, Q, S, or T;
each of X₈ and X₁₇ is, independently, G, R, H, K, D, E, N, Q, S, or T;
X₉ is F, Y, or W;
X₁₀ is A, V, I, L, F, Y, or W;
X₁₂ is G, A, V, I, L, D, E, N, Q, S, or T;
X₁₃ is A, V, I, L, N, or Q;
X₁₄ is G, D, E, N, or Q;
X₁₅ is G, A, V, I, L, or absent;
X₁₈ is A, V, I, L, R, H, K, N, Q, F, Y, or W;
X₁₉ is A, V, I, L, P, S, or T;
each of X₂₀ and X₂₆ is, independently, G, A, V, I, L, N, Q, S, or T;
X₂₁ is A, V, I, L, R, H, K, S, or T;
X₂₂ is A, V, I, L, M, D, or E;
X₂₄ is N, Q, S, or T; and
X₂₇ is R, H, or K.

In one embodiment, protein includes a polypeptide sequence having at least 90% sequence identity to SEQ ID NO: 27:

$$CX_2X_3CX_5X_6X_7X_8, \text{ wherein:}$$

X₂ is G, A, V, I, L, P, N, Q, S, or T;
X₃ is A, V, I, or L;
X₅ is G, A, V, I, L, D, E, N, Q, S, or T;
X₆ is G, A, V, I, L, M, N, Q, S, or T;
X₇ is R, H, K, D, E, P, F, Y, or W; and
X₈ is A, V, I, L, M, S, or T.

In one embodiment, protein includes a polypeptide sequence having at least 90% sequence identity to SEQ ID NO: 28:

$$X_1CX_3X_4CX_6X_7X_8X_9, \text{ wherein:}$$

X₁ is A, V, I, L, F, Y, W, or absent;
X₃ is S, T, F, Y, or W;
X₄ is G, A, V, I, L, S, or T;
X₆ is A, V, I, L, R, H, K, D, E, S, or T;
X₇ is A, V, I, L, R, H, K, S, T, F, Y, or W;
X₈ is A, V, I, L, N, Q, S, or T; and
X₉ is A, V, I, L, R, H, or K.

In addition to a first mutant gene encoding a cytoplasmic tRNA thiolation protein, the host cell can include one or more second mutant genes. In one embodiment, the second mutant gene encodes a target protein selected from the group consisting of an acetyl-CoA carboxylase, a lysophospholipid acyltransferase, a fatty-acyl-CoA oxidase, a fatty acid synthase, a fatty-acyl-CoA reductase, an aldehyde reductase, a fatty-acyl-CoA synthetase, a thioesterase, a carboxylic acid reductase, a fatty alcohol oxidase, a fatty alcohol reductase, an aldehyde dehydrogenase, an isocitrate dehydrogenase, or a pyruvate decarboxylase.

In particular embodiments, the second mutant gene provides a host cell having low FOH catabolism, as compared to a parent or control strain lacking the second gene. In other embodiments, the second mutant gene provides a host cell having low re-importation of secreted FOH, as compared to a parent or control strain lacking the second gene. In yet other embodiments, the second mutant gene provides a host cell having high export of FOH and/or having improved or alleviated FOH toxicity, as compared to a parent or control strain lacking the second gene.

In one embodiment, the host cell includes a mutant gene that encodes a target protein that is an acetyl-CoA carboxylase. In particular embodiments, the mutant gene includes deletion of the nucleic acid encoding the acetyl-CoA carboxylase. In some embodiments, the acetyl-CoA carboxylase includes a polypeptide sequence having at least 90% sequence identity to SEQ ID NO: 30 (FIG. 4A).

In another embodiment, the host cell includes a mutant gene that encodes a target protein that is a lysophospholipid acyltransferase. In particular embodiments, the mutant gene includes expression or overexpression of the nucleic acid encoding the lysophospholipid acyltransferase. In some embodiments, the lysophospholipid acyltransferase includes a polypeptide having at least 90% sequence identity to SEQ ID NO: 31 (FIG. 4B). Expression or overexpression can include random integration using a plasmid, in which the target gene can be under the control of a promoter (e.g., a glyceraldehyde-3-phosphate dehydrogenase (GAPDH) promoter); or include targeted integration, in which the target gene is under the control of a promoter (e.g., a translational elongation factor Ef-1 (TEF1) promoter). The location of gene integration can be at any locus, e.g., in which the target locus can include ku70, NCS2 and ALE1, all in FOH producing strains.

In yet another embodiment, the host cell includes a mutant gene that encodes a target protein that is a fatty alcohol oxidase. In particular embodiments, the mutant gene includes deletion of the nucleic acid encoding the fatty alcohol oxidase. In some embodiments, the fatty alcohol oxidase includes a polypeptide sequence having at least 90% sequence identity to SEQ ID NO: 32 (FIG. 4C).

In another embodiment, the host cell includes a mutant gene that encodes a target protein that is an alcohol dehydrogenase. In particular embodiments, the mutant gene includes deletion of the nucleic acid encoding the alcohol dehydrogenase. In some embodiments, the alcohol dehydrogenase includes a polypeptide sequence having at least 90% sequence identity to SEQ ID NO: 33 (FIG. 4D) or SEQ ID NO: 36 (FIG. 4G).

In one embodiment, the host cell includes a mutant gene that encodes a target protein that is an isocitrate dehydrogenase. In particular embodiments, the mutant gene includes deletion of the nucleic acid encoding the isocitrate dehydrogenase. In some embodiments, the isocitrate dehydrogenase includes a polypeptide sequence having at least 90% sequence identity to SEQ ID NO: 34 (FIG. 4E).

In another embodiment, the host cell includes a mutant gene that encodes a target protein that is a pyruvate decarboxylase. In particular embodiments, the mutant gene includes deletion of the nucleic acid encoding the pyruvate decarboxylase. In some embodiments, the pyruvate decarboxylase includes a polypeptide sequence having at least 90% sequence identity to SEQ ID NO: 35 (FIG. 4F).

In particular embodiments, modification (e.g., over-expression) of a lipase, a transhydrogenase (e.g., a NADPH transhydrogenase), and/or an acyl-CoA synthetase/ligase may be synergistic. In some embodiments, a mutant herein include two or more mutations that exhibit additive or synergistic effects.

The host cell can include a first mutant gene encoding a first target protein and a second mutant gene encoding a second target protein, in which the first and second target proteins are different. The first target protein can include a cytoplasmic tRNA thiolation protein, and the second target protein can be any in a pathway that can enhance fatty alcohol (FOH) production. FIG. 5 shows a non-limiting lipid synthesis pathway, which shows various proteins and lipid-derived compounds. Non-limiting lipid-derived compounds include acetyl-CoA, malonyl Co-A, fatty-acyl-CoA, fatty alcohol (FOH), free fatty acid (FFA), and free aldehyde (FAL). Non-limiting target proteins (e.g., which can be encoded as the second mutant gene) include acetyl-CoA carboxylase (ACC), fatty acid synthase (FAS), fatty-acyl-CoA oxidase, fatty-acyl-CoA reductase (FAR), fatty-acyl-CoA synthetase (FAA), thioesterase (TES), aldehyde dehydrogenase (ALD), carboxylic acid reductase (CAR), and aldehyde reductase (AHR).

Lipid-Derived Compound

The host cells and methods herein can be used to provide a lipid-derived compound. In particular embodiments, the host cell provides an increased concentration of the lipid-derived compound, as compared to a control cell. The control cell can be a parental cell or parental strain that lacks any of the modifications described herein for the first mutant gene and/or second mutant gene.

Non-limiting lipid-derived compounds include a fatty alcohol, a fatty acid, a fatty aldehyde, a fatty alkene, a fatty amide, a fatty ester, a fatty alkane, and a fatty diacid. Yet other lipid-derived compounds can include an oil, a lipid, a glycerolipid, a sphingolipid, a sterol lipid, or a triacylglyceride. In some embodiments, a lipid-derived compound includes a class of molecules that are soluble in nonpolar solvents (e.g., ether or chloroform), are relatively or completely insoluble in water, and include one or more hydrocarbon chains which are hydrophobic.

In particular embodiments, the lipid-derived compound is a fatty alcohol. Non-limiting fatty alcohols can include at least one hydroxyl group (—OH) and at least on aliphatic group, as defined herein. In particular embodiments, the fatty alcohol includes a structure of R'OH, in which R' is an optionally substituted $C_{4-32}$ aliphatic. In other embodiments, the fatty alcohol is lauryl alcohol (1-dodecanol), tridecyl alcohol (1-tridecanol), myristyl alcohol (1-tetradecanol), pentadecyl alcohol (1-pentadecanol), cetyl alcohol (1-hexadecanol), palmitoleyl alcohol (cis-9-hexadecen-1-ol), heptadecyl alcohol (1-n-heptadecanol), stearyl alcohol (1-octadecanol), oleyl alcohol (1-octadecenol), nonadecyl alcohol (1-nonadecanol), arachidyl alcohol (1-eicosanol), or combinations thereof.

In other embodiments, the lipid-derived compound is a fatty-acyl-coenzyme A (CoA) derived chemical. Non-limiting chemicals include a fatty alcohol, as well as combinations including two or more different fatty alcohols.

Host Cells

The host cells herein are genetically modified in that heterologous nucleic acid have been introduced into the host cells, and as such the genetically modified host cells do not occur in nature. The suitable host cell is one capable of expressing a protein (e.g., any described herein) from a nucleic acid configured to encode that protein.

In one embodiment, the host cell is a genetically modified oleaginous organism. As used herein, an oleaginous organism includes an organism that can accumulate more than about 20% (w/w) of lipid-derived compounds on a cell dry weight basis. Non-limiting oleaginous organisms include microalgae, bacteria, fungi, and yeast (e.g., an oleaginous yeast cell, *Rhodosporidium*, and the like).

In some embodiments, the oleaginous organism is an oleaginous yeast. Non-limiting examples include *Apiotrichum* (e.g., *A. curvatum*), *Candida* (e.g., *C. ortholopsis, C. pseudolambica*, or *C. viswanathii*), *Cryptococcus* (e.g., *C. albidus, C. curvatus, C. phenolicus, C. podzolicus, C. terricola*, or *C. vishniaccii*), *Cutaneotrichosporon* (e.g., *C. oleaginosus*), *Cystobasidium* (e.g., *C. oligophagum*), *Cystofilobasidium* (e.g., *C. informiminiatum*), *Debaromyces* (e.g., *D. hansenii*), *Issatchenika* (e.g., *I. occidentalis*), *Leucosporidium* (e.g., *L. scottii*), *Lipomyces* (e.g., *L. starkeyi*), *Occultifur* (e.g., *O. externus*), *Pichia* (e.g., *P. deserticola* or *P. segobiensis*), *Rhizopus* (e.g., *R. arrhizus*), *Rhodosporidium* (e.g., *R. azoricum, R. bajevae, R. diobovatum, R. fluviale, R. kratochvilovae, R. paludigenum, R. sphaerocarpum*, or *R. toruloides*), *Rhodotorula* (e.g., *R. araucariae, R. bogoriensis, R. colostri, R. dairenensis, R. glutinis, R. graminis, R. minuta*, or *R. mucilaginosa*), *Sporidiobolus* (e.g., *S. johnsonii, S. pararoseus, S. ruineniae*, or *S. salmonicolor*), *Sporobolomyces* (e.g., *S. bannaensis, S. carnicolor, S. metaroseus, S. odoratus, S. poonsookiae*, or *S. singularis*), *Starmerella* (e.g., *S. bombicola*), *Trichosporon* (e.g., *T. oleaginosus* or *T. porosum*), and *Yarrowia* (e.g., *Y. lipolytica*).

Any prokaryotic or eukaryotic host cell may be used in the present method so long as it remains viable after being transformed with a sequence of nucleic acids configured to encode a protein described herein (e.g., NCS2, ACC1, ALE1, or others). Prokaryotic cells include bacteria or archaea cells. Suitable eukaryotic cells include, but are not limited to, fungal, insect, or mammalian cells. Suitable fungal cells are yeast cells, which may belong to the genus *Rhodosporidium, Blastomyces, Candida, Citeromyces, Crebrothecium, Cryptococcus, Debaryomyces, Eremothecium, Geotrichum, Kloeckera, Lipomyces, Pichia, Rhodotorula, Saccharomyces* (e.g., *S. bayanus, S. carlsbergensis, S. cerevisiae*, or *S. pastorianus*), *Schizosaccharomyces, Sporobolomyces, Trichosporon*, or *Wickerhamia*.

Preferably, the host cell is not adversely affected by the transduction of the necessary nucleic acid sequences, the subsequent expression of the proteins (e.g., enzymes), or the resulting intermediates required for carrying out the steps associated with the fatty alcohol pathway. In one embodiment, it is preferred that minimal "cross-talk" (i.e., interference) occur between the host cell's own metabolic processes and those processes involved with the fatty alcohol pathway. In another embodiment, it is preferred that the host cell includes other mutant gene(s) that provide low catabolism of fatty alcohol and/or provide minimal re-importation of secreted fatty alcohol.

Incubation in a Culture

The host cell can be incubated in a culture having any useful medium. Such medium can include growth medium, biomass, nutrients, micronutrients, cofactors, and such, as well as combinations thereof. Non-limiting components within the medium can include a carbon source, an amino acid, a peptide, a lipid, a vitamin, a trace element, a salt, a growth factor, a buffer, or combinations thereof.

The medium can include any useful carbon source, such as and without limitation, acetate, arabinose, carboxymethylcellulose, cellulose, cellulosic material (e.g., depolymerized cellulose material), corn starch, fructose, galactose, glucose, glycerol, lactose, mannose, milk whey, molasses, potato, rhamnose, ribose, rice, sorghum, starch, sucrose, sugar alcohol, sugar beet pulp (e.g., depolymerized sugar beet pulp), sugar cane, switchgrass, wheat, xylose, a feedstock (e.g., whole whey, modified whey products, dairy permeates, crop residues, and the like), and/or a biomass (e.g., lignocellulosic biomass or a hydrolysate thereof), as well as mixtures thereof. Yet other carbon sources include monosaccharides, disaccharides, oligosaccharides, polysaccharides, monoglycerides, diglycerides, triglycerides, alkanes, fatty acids, fatty acid esters, phospholipids, vegetable oils (e.g., soybean oil), or animal fats.

Any useful biomass can be employed. A biomass (e.g., a lignocellulosic biomass) may include agricultural residues (e.g., corn stover or sugarcane bagasse), energy crops (e.g., grass, such as elephant grass, silver grass, Sudan grass, or switchgrass; poplar trees; willow; maize; millet; white sweet clover; rapeseed; jatropha; or sugarcane), food waste (e.g., Brewers' spent grain), wood residues (e.g., sawmill or papermill discard), or municipal paper waste.

Yet other exemplary biomass includes corn stover (e.g., deacetylation and mechanical refining (DMR) processed corn stover or de-acetylated corn stover hydrolysate from the National Renewable Energy Laboratory (NREL), Golden, Colo.), corn cob hydrolysate, fishwaste hydrolysate, paper industry effluent or waste product (e.g., black liquor), rice residue hydrolysate, sugar beet molasses, sugarcane molasses, wastewater (e.g., distillery wastewater, livestock wastewater, or municipal wastewater), distillers grains or co-products (e.g., wet distillers grains (WDGs), dried distillers grains (DDGs), dried distillers grains with solubles (DDGS), fatty acids from oil hydrolysis, lipids from evaporation of thin stillage, syrup, distillers grains, distillers grains with or without solubles, solids from a mash before fermentation, solids from a whole stillage after fermentation, biodiesel, and acyl glycerides), oilseed meals (e.g., soybean meal or canola meal), feeds (e.g., alfalfa meal, cottonseed meal, DDGS, rice bran, or wheat bran), and others.

The medium may be supplemented with a nitrogen source (to increase the concentration of nitrogen) or supplemented within an agent to capture nitrogen (to decrease the concentration of nitrogen, such as with a chelating agent). For instance, nitrogen may be supplied from an inorganic source (e.g., $(NH_4)_2SO_4$, $NH_4Cl$, or another ammonium source) or organic source (e.g., urea, glutamate, or an amino acid). The nitrogen source can be any nitrogen-containing composition (e.g., compound, mixture of compounds, salts, etc.) that an organism may metabolize for organism viability. The concentration of nitrogen within the medium can be controlled to provide a nitrogen-rich environment, a standardized nitrogen-containing environment, or a nitrogen-poor environment. In particular embodiments, the concentration of nitrogen is from about 0.5 to 5 g/L of ammonium (e.g., $NH_4SO_4$).

In embodiments, the medium can include one or more micronutrients. Non-limiting micronutrients include cobalt, copper, zinc, iron, and/or potassium. In particular embodiments, the growth medium can include from about 0 to 2 $\mu M$ of zinc, 0 to 20 $\mu M$ of cobalt, and/or 0 to 20 $\mu M$ of copper.

In one embodiment, the medium includes corn stover hydrolysate medium (mechanically refined de-acetylated corn stover hydrolysate from NREL) diluted to a concentration, such that final glucose concentration is approximately 75 g/L glucose and xylose is approximately 40 g/L, plus 100 mM potassium phosphate and 1 g/L ammonium sulfate.

In another embodiment, the medium includes a mixture (e.g., a 10:1 to 5:1 mixture) of Difco™ Yeast Nitrogen Base (YNB) without amino acids (includes a long list of trace elements and some vitamins like thiamine and 5 g/L ammonium sulfate) with Complete Supplement Mix (CSM, several amino acids and some nucleotides, from Sunrise Science Products, Inc.) plus 100 mM potassium phosphate plus 75 g/L glucose plus 40 g/L xylose.

The host cell can be incubated in any useful medium. The terms "culture," "cultivate," "ferment", and "incubate" are used interchangeably and refer to the intentional growth, propagation, proliferation, and/or enablement of metabolism, catabolism, and/or anabolism of one or more host cells. The combination of both growth and propagation may be termed proliferation. Culture does not refer to the growth or propagation of microorganisms in nature or otherwise without human intervention. Exemplarily, host cells may be cultivated in a suspension culture or on plates such as, e.g., agar plates. The suspension medium or agar may contain nutrients suitable for the host cells. The cells may be cultivated at aerobic or anaerobic conditions.

Preferably, the cultivation of cells leads to the reproduction of the cells. Reproduction may occur form cell division of the yeast cell(s), budding of the yeast cell(s), formation of spores, formation of one or more gamete(s) and/or sexual reproduction. More preferably, the reproduction of the yeast cell(s) is cell division or budding.

Cultivation of the cells may include cultivation in a laboratory scale, e.g., cultivation of several culture plates or suspension cultures of several milliliters up to few liters culture broth. Cultivation of the cells may further include cultivation in a semi-technical scale, e.g., cultivation of suspension cultures of several liters culture broth and cultivation in an industrial scale, e.g., cultivation of suspension cultures of several liters or even several square meters culture broth. A culture broth can include both host cells and the medium. A suspension culture may optionally be stirred or shaken. A suspension culture may optionally be aerated, ventilated and/or degassed. The cells may be cultivated at a suitable pressure, the pressure may be atmospheric pressure, excess pressure or underpressure. Typically, the cells may be cultivated at atmospheric pressure or slight excess pressure.

Conditions for cultures can be optimized to promote growth. For instance, non-limiting temperatures for cultures can be from about 28° C. to 32° C., and non-limiting culture times can be from three to ten days (e.g., from four to seven days).

Isolation from a Culture

The host cells or byproducts of the host cell can be isolated from the culture. Non-limiting byproducts can be a lipid-derived compound, such as a fatty alcohol or a combination of different fatty alcohols.

In one embodiment, the host cell is cultured in the presence of an organic solvent (e.g., a hydrocarbon solvent, such as dodecane or pentadecane) as an overlay. Upon mixing, the aqueous media and the organic overlay can form an emulsion. As FOH is produced from the cells, it can partition into the organic layer. After mixing is stopped, the organic layer and aqueous layer can be easily separated by way of any isolating methods described herein.

Isolation from culture can include separating the host cells from other components within the suspension, culture, or culture broth. Such separating can include harvesting the host cells or harvesting the lipid-derived compound from the culture. Isolating can include any useful methodology, e.g., centrifugation, chromatography (e.g., affinity, size exclusion, ion-exchange chromatography, and others), crossflow filtration, filtration, or abrasion or swabbing off a solid surface or culture plate. Alternatively, the cells may descent over time or may float due to gassing of the container including such cells. Alternatively, the cells are not isolated, but the cells and the medium are treated further together.

The cells can be harvested and optionally washed. Subsequently, the cells may be optionally lysed by any means known in the art and indicated above. Optionally, the lipid-derived compound(s) may be extracted by solvent extraction, e.g., with an organic solvent. Optionally, the organic solvent may be evaporated subsequently. Alternatively or additionally, the lipid-derived compound(s) may be isolated, depending on their specific chemical nature, by chromatographic methods (e.g., phase chromatography, ion-exchange chromatography, reverse phase chromatography, size exclusion chromatography, high performance liquid chromatography (HPLC), ultrahigh pressure liquid chromatography (UPLC), fast protein chromatography (FPLC)), by electrophoresis, capillary electrophoresis (CE), or by distillation.

The lipid-derived compounds from the culture can be captured by distillation, filtration, phase separation, as well as and/or solvent co-extraction. Any useful distillation and extraction techniques can be employed, including flash extraction, ionic liquid extraction, etc., to isolate one or more lipid phases, oils, aqueous phases, aqueous co-products, nutrients, etc. Phase separation can include any that separate liquid from solid phases, as well as separate two or more phases that can be differentiated based on solubility, miscibility, etc., (e.g., as those present in non-aqueous phases, aqueous phases, lipophilic phases, etc.) in any useful solvent (e.g., an organic solvent, an aqueous solvent, water, buffer, etc.). Phase separation techniques include flash separation, acid absorption, filtration, distillation, solvent extraction, ion liquid extraction, etc. The resultant products and co-products can include one or more intermediate products that can optionally be processed to form useful end-use products.

EXAMPLES

Example 1: Manipulation of tRNA Thiolation Gene Ncs2 for Enhanced Production of Fatty-Acyl-CoA Derived Chemicals in *R. toruloides*

Fatty alcohols are a versatile class of chemicals with many consumer and industrial applications. The Agile Biofoundry is developing strains of the oleaginous yeast *Rhodosporidium toruloides* (also known as *Rhodotorula toruloides*) to convert lignocellulosic hydrolysate into fatty alcohols (see, e.g., Liu D et al., "Exploiting nonionic surfactants to enhance fatty alcohol production in *Rhodosporidium toruloides*," *Biotechnology and Bioengineering* 2020; 117: 1418-1425).

There are several aspects of bioconversion of lignocellulose derived carbon to fatty alcohols in *R. toruloides* that may include optimization to achieve a commercially viable process. These include process optimization of extraction and separation of hydrophobic fatty alcohols from liquid cultures, mitigation of toxic effects of high concentrations of fatty alcohols on production the production host, fermentation and media optimization, and/or optimization of expression of heterologous enzymes in a non-model yeast. In particular, we explored global remodeling of central carbon metabolism to improve flux to fatty alcohols.

The immediate precursor to long chain fatty alcohols is fatty-acyl-CoA. Fatty-acyl-CoA sits at the nexus of the fatty acid biosynthesis pathway at the cytosol/endoplasmic reticulum (ER) membrane, the network of pathways that participate in membrane lipid synthesis and recycling in the ER and endomembrane network, the carbon storage pathway for triacylglyceride synthesis and the interface of the ER and the lipid droplet, and the fatty acid catabolic pathway through beta-oxidation of fatty-acyl-CoA in the peroxisome and mitochondria. Thus, fatty-acyl-CoA is the product or substrate of numerous enzymes in all cellular compartments, as well as a participant in many reactions essential for cell survival.

In order to maximize carbon flux to fatty alcohol, the flux into these alternate fates for fatty acyl-CoA can be minimized. However, in many cases, crude gene deletions and elimination of the competing pathways could be lethal to the cell, and the enzymes involved are so numerous as to make direct targeting of them all prohibitively laborious given the current state of genome engineering tools for R. toruloides. Thus, as part of our genome engineering strategy, we set out to identify single gene deletions with global effects on carbon metabolism that are synergistically beneficial to increasing available fatty-acyl-CoA. Such single gene deletions can be optionally combined with other gene modifications to further tune production of desired lipid-derived compounds, such as fatty alcohol.

We have identified dozens of genes with altered lipid accumulation in R. toruloides through a global functional genomics screen of cell buoyancy and fluorescence activated cell sorting (see, e.g., Coradetti S T et al., "Functional genomics of lipid metabolism in the oleaginous yeast Rhodosporidium toruloides," eLife 2018; 7: Article No. e32110 (55 pages)). Many of the identified genes had only very general functional predictions by sequence homology or functional predictions that did not obviously explain their lipid accumulation phenotypes. Several of these mutants were selected for further study in a fatty alcohol production context, in the hopes that altered lipid accumulation would also result in altered fatty alcohol production and shed light on function the metabolic regulatory network we aim to optimize.

One of these mutations was the deletion of protein ID 10764, ortholog of Saccharomyces cerevisiae gene ncs2. This gene has annotated function in the thiolation of several tRNAs. It has been noted in S. cerevisiae that carbon metabolism are altered in the ncs2 deletion mutants, with major changes in phosphate acquisition, amino acid metabolism, and storage carbohydrates, leading to a hypothesis that gene has some role in nutrient sensing (see, e.g., Gupta R et al., "A tRNA modification balances carbon and nitrogen metabolism by regulating phosphate homeostasis," eLife 2019; 8: Article No. e44795 (33 pages)), but the mechanism and adaptive function of that regulation remains unclear. To date, we are aware of no investigation of ncs2s effect on lipid metabolism in S. cerevisiae or any other species.

Protein ID 10764 is predicted to be a 612 amino acid protein containing the interpro domain IPR019407 conserved in cytoplasmic tRNA thiolation proteins. The most closely related gene in S. cerevisiae is the tRNA thiolation protein ncs2, apparently orthologous to R. toruloides protein ID 10764. The Ncs2 protein sequence is well conserved across diverse eukaryotes. FIG. 1A shows a phylogenetic tree built from significant sequence matches (BLAST) from 17 model eukaryote proteomes. Orthologs are present in single copy across fungi, plants, animals and early diverging eukaryotes, suggesting highly conserved molecular function.

Thus far, the function of ncs2 function has been characterized mainly in S. cerevisiae. This function is the thiolation of the wobble position in tRNAs for glutamine, glutamate, and lysine. Thiolation enhances translation efficiency of codons using those tRNAs, but only modestly. Currently, the adaptive function of ncs2 thus remains unclear, though multiple studies have demonstrated altered carbon and amino acid metabolism. Gupta et al., supra, argued that thiolation of these tRNAs may be an indirect way of sensing sulfur availability, with hypo-thiolation serving as a signal for sulfur scarcity, which in turn triggers a phosphate-limited metabolic response through regulation of phosphate acquisition genes.

Deletions for ncs2 and other proteins in the tRNA thiolation pathway had significant reductions in lipid accumulation in a high throughput functional genomics study of R. toruloides. How this low lipid phenotype might be consistent with a role in sulfur sensing is unclear, as previous studies on nutrient limitation in R. toruloides have observed increased lipid accumulation in conditions of sulfur limitation and phosphate limitation (see, e.g., Wu S et al., "Microbial lipid production by Rhodosporidium toruloides under sulfate-limited conditions," Bioresource Technology 2011; 102(2): 1803-1807; and Wang Y et al., "Systems analysis of phosphate-limitation-induced lipid accumulation by the oleaginous yeast Rhodosporidium toruloides," Biotechnology for Biofuels 2018; 11: Article No. 148 (15 pages)).

Example 2: Deletion Mutants for Ncs2 have Increased Fatty Alcohol Production

The ncs2 gene was deleted by transforming a Ku70 deficient strain of R. toruloides IFO 0880 expressing fatty acyl-CoA reductase from Marinobacter aquaeolei (ABF archived strain ABF_006072) with a nourseothricin resistance cassette, replacing the ncs2 coding sequence by homologous recombination. The resulting strain is stored in the ABF strain archive as strain ABF_006749.

The ncs2 deletion strain was grown on media prepared from deacetylated mechanically refined enzymatic hydrolysate (DMR-EH) from corn stover (see, e.g., Chen X et al., "DMR (deacetylation and mechanical refining) processing of corn stover achieves high monomeric sugar concentrations (230 g/L) during enzymatic hydrolysis and high ethanol concentration (>10% v/v) during fermentation without hydrolyzate purification or concentration," Energy & Environmental Science 2016; 9(4): 1237-1245) provided by NREL.

In the final media composition, concentrated DMR-EH was diluted to approximately 75 g/L glucose, 40 g/L xylose, with addition of 1 g/L or 5 g/L ammonium sulfate, 100 mM potassium phosphate, and 0.1% (v/v) Tergitol™ (an ethoxylated alcohol that serves as a linear non-ionic surfactant). Cultures were incubated 3 to 6 days at 30° C., 1000 rpm in an M2P labs 48-well flower plate with 800 µl culture volume and 200 µl dodecane overlay. Total fatty alcohol was measured from the dodecane overlay by the additional of 100 µl dodecane with 100 mg of 1-tridecanol, mixing, and then separating the organic overlay for analysis by GC-FID. Fatty alcohols of 16 and 18 carbon length were then quantified against the 1-tridecanol internal standard. Total fatty alcohol concentrations in Δncs2 cultures were 2-3 times that of the parent strain (FIG. 6).

Example 3: Deletion Mutants for Ncs2 have Globally Altered Lipid and Proteomic Profiles To explore the mechanism of increased fatty alcohol production in Δncs2 mutants, we subjected three day old DMR-EH grown cultures to metabolomic, proteomic, and lipidomic analysis and compared them to the parent strain in the same conditions. A similar analysis was carried out on several other mutant strains as part of a larger study. In FIGS. 7-8, comparable data from strain STC105

(ABF_006090, fatty alcohol producing strain over-expressing a native lipase) and strain STC153 (ABF_006597, fatty alcohol producing strain expressing a nicotinamide nucleotide transhydrogenase, NNT) are included as an informative control as STC105 and STC153 also exhibit increased fatty alcohol production through independent mechanisms.

Of 100 water soluble metabolites quantified, relatively few had different abundance in the Ancs2 mutant sufficient for a P-value <0.05 with an independent T-test, without multiple hypothesis correction. In the low nitrogen condition, which had the greatest fatty alcohol production, only 3-phosphoglycerate, citrate, glycerol-3-phosphate, D-ribose-5-phosphate, and sucrose were less abundant in the Ancs2 mutant than the parent strain, and only 1-octadecanol was more abundant.

Of 3375 proteins with measurable peptide abundances in global proteomics analysis, 562 had significantly different abundances in the ncs2 deletion mutant than the parent strain in the same condition and this differential abundance was similar between high and low nitrogen cultures. Notably, there was a high degree of overlap between the proteomic changes in the ncs2 mutant and the lipase over-expression mutant (FIGS. 7A-7B), but essentially no overlap with the NNT mutant. These results demonstrate that the proteomic changes are not a result of fatty alcohol toxicity or another indirect effect of increased flux to fatty alcohols.

For FIGS. 7A-7B, the lipase overexpression (OE) strain was ABF_006090 (or STC0105), which included a putative triacylglycerol (TAG) lipase (R. toruloides IF00880 v4.0, Protein Id: 8386; UniProtKB No. A0A2T0AH33) driven by the Tef1 promoter. The NNT overexpression strain was ABF_006596 (aka STC0152), which included an NNT (NAD(P) transhydrogenase or nicotinamide nucleotide transhydrogenase) from Haliaeetus leucocephalus driven by the Tef1 promoter.

Generally, proteomic analysis of the ncs2 mutant were more comparable to the global expression profile for the lipase overexpression (OE) mutant than the NNT OE mutant. Without wishing to be limited by mechanism, lipid metabolism is likely perturbed in the ncs2 mutant, which may provide the higher FOH production.

Of 301 lipid species measured with global proteomics, 60 had significantly altered abundance in the ncs2 deletion strain versus its parent, particularly in low nitrogen conditions (FIG. 8). This pattern of altered lipid abundance was markedly different in the lipase over expression strain. These results suggest that while altered lipid abundance is sufficient to trigger many elements of the Ancs2 mutants proteomic shift, it is unlikely that the Ancs2 mutant achieves this through a shared mechanism with the lipase over expression strain, as their lipid profiles are globally divergent and in particular that Ancs2 mutant has only modest lipid changes in the high nitrogen condition, yet a very consistent proteomic profile between high and low nitrogen conditions. Without wishing to be limited by mechanism, the Ancs2 mutant is altering proteomic abundance through an unknown, lipid independent mechanism.

Regardless of mechanism, the Ancs2 mutant exhibit a synergistic combination of altered protein abundance that shifted carbon flux from lipid synthesis towards fatty alcohol synthesis by inhibiting several early steps in the diacylglycerol and phospholipid synthesis, thus removing a major sink for fatty-acyl-CoA, while increasing abundance of NADPH though activity of malic enzyme Mea1, thus promoting fatty-acyl-CoA synthesis. Liberation of fatty-acyl-CoA from storage lipids acids is also reduced by down regulation of several lipases and long chain fatty acyl-CoA synthetases, but that is balanced by concomitant down regulation of fatty-acyl-CoA degradation through beta-oxidation. These changes are summarized in FIG. 9.

Quantitative changes in relative protein intensity for several proteins (provided in Table 1) in these pathways are shown in FIGS. 10A-10D. While many of these changes in abundance are modest (less than 2-fold, or smaller than 1 in log 2 space), the combined effect across multiple pathways is significant. This effect can be evidenced by the consistent depletion of several lipid classes, particularly diacylglycerides, the final shared precursor of triacylglycerides and several membrane lipids (FIG. 11).

In Table 1, the Protein Id correspond to protein IDs provided for the JGI's genome assembly for Rhodosporidium toruloides, which can be accessed at mycocosm.jgi.doe.gov/Rhoto_IFO0880_4/Rhoto_IF00880_4.home.html.

TABLE 1

List of genes and Protein Id

| Abbreviation | Annotation | Group | Protein Id |
|---|---|---|---|
| Mea1 | malate dehydrogenase (oxaloacetate-decarboxylating) (NADP+); malic enzyme (EC: 1.1.1.40); NAD-dependent malic enzyme (EC: 1.1.1.38) | Fatty Acid (FA) Synthesis | 12761 |
| Gpd1-1 | glycerol-3-phosphate dehydrogenase (NAD+) (EC:1.1.1.8) | Lipid Synthesis | 12154 |
| Gpd1-2 | glycerol-3-phosphate dehydrogenase (NAD+)(EC:1.1.1.8) | Lipid Synthesis | 14576 |
| Ayr1 | 1-acyl dihydroxyacetone phosphate reductase and related dehydrogenases; acylglycerone-phosphate reductase (EC:1.1.1.101) | Lipid Synthesis | 15575 |
| Sct1 | phospholipid/glycerol acyltransferase; glycerol-3-phosphate O-acyltransferase/dihydroxyacetone phosphate acyltransferase | Lipid Synthesis | 15435 |
| Slc1 | lysophosphatidate acyltransferase; 1-acylglycerol-3-phosphate O-acyltransferase (EC:2.3.1.51) | Lipid Synthesis | 10427 |
| Pah1 | LPIN phosphatidate phosphatase; phosphatidate phosphatase (EC:3.1.3.4) | Lipid Synthesis | 12485 |

TABLE 1-continued

List of genes and Protein Id

| Abbreviation | Annotation | Group | Protein Id |
|---|---|---|---|
| Ale1 | lysophospholipid acyltransferase; membrane-bound O-acyltransferase (MBOAT) family; acyltransferase | Lipid Synthesis | 16030 |
| Lcb1 | serine C-palmitoyltransferase (EC:2.3.1.50) | Lipid Synthesis | 10303 |
| Are1 | sterol O-acyltransferase/diacyl O-acyltransferase (EC:2.3.1.26); MBOAT family | Lipid Synthesis | 11799 |
| Dga1 | MGAT2 2-acylglycerol O-acyltransferase 2; 2-acylglycerol O-acyltransferase (EC:2.3.1.22) | Lipid Synthesis | 16460 |
| Lro1 | phospholipid:diacylglycerol acyltransferase (EC:2.3.1.158); lechitin:cholesterol acyltransferase | Lipid Synthesis | 16477 |
| Acc1 | acetyl-CoA carboxylase; acetyl-CoA carboxylase, biotin carboxylase subunit (EC:6.4.1.2, 6.3.4.14); acetyl-CoA carboxyl transferase domain of homomeric ACCase (EC 6.4.1.2) | FA Synthesis | 8639 |
| Fas1 | fatty-acyl-CoA synthase system (EC:2.3.1.86); fatty acid synthase subunit beta, fungi type | FA Synthesis | 8670 |
| Fas2 | fatty-acyl-CoA synthase system (EC:2.3.1.86); fatty acid synthase subunit alpha, fungi type | FA Synthesis | 8777 |
| ACAD10 | acyl-CoA dehydrogenase family member 10; medium-chain acyl-CoA dehydrogenase (EC:1.3.8.7); acyl-CoA dehydrogenase (EC: 1.3.99.3) | Beta-Oxidation | 10408 |
| FOX2 | multifunctional beta-oxidation protein (EC: 1.1.1.-4.2.1.-]); short-chain dehydrogenase/reductase (SDR) | Beta-Oxidation | 11362 |
| POT1-1 | acetyl-CoA C-acyltransferase 1 (EC:2.3.1.16) | Beta-Oxidation | 13813 |
| POT1-2 | acetyl-CoA C-acyltransferase (EC:2.3.1.16); 3-oxoacyl CoA thiolase; 3-ketoacyl-CoA thiolase (EC:2.3.1.16) | Beta-Oxidation | 9065 |
| ACADM | acd acyl-CoA dehydrogenase; acyl-CoA dehydrogenase (EC: 1.3.99.3); medium-chain acyl-CoA dehydrogenase (EC:1.3.8.7) | Beta-Oxidation | 12570 |
| EHD3 | enoyl-CoA hydratase (EC:4.2.1.17) | Beta-Oxidation | 14805 |
| HADH | 3-hydroxyacyl-CoA dehydrogenase (EC: 1.1.1.35) | Beta-Oxidation | 11203 |
| ACAA2 | acetyl-CoA acyltransferase 2; acetyl-CoA C-acyltransferase (EC: 2.3.1.16) | Beta-Oxidation | 8885 |
| TGL2 | triacylglycerol lipase (EC:3.1.1.3) | Lipases and LCFA | 10393 |
| TGL2 | triacylglycerol lipase (EC:3.1.1.3) | Lipases and LCFA | 14317 |
| YEH2 | lysosomal acid lipase/cholesteryl ester hydrolase; sterol esterase (EC:3.1.1.13) | Lipases and LCFA | 14617 |
| TGL5 | Predicted esterase of the alpha-beta hydrolase superfamily; patatin-like phospholipase | Lipases and LCFA | 9746 |
| RTO4_8386 | arylacetamide deacetylase; triacylglycerol lipase (EC:3.1.1.3) | Lipases and LCFA | 8386 |
| RTO4_8726 | arylacetamide deacetylase; alpha/beta hydrolase fold | Lipases and LCFA | 8726 |
| RTO4_8745 | arylacetamide deacetylase; alpha/beta hydrolase fold | Lipases and LCFA | 8745 |
| RTO4_8919 | arylacetamide deacetylase; alpha/beta hydrolase fold | Lipases and LCFA | 8919 |
| RTO4_9174 | arylacetamide deacetylase; alpha/beta hydrolase fold | Lipases and LCFA | 9174 |
| RTO4_9181 | arylacetamide deacetylase; alpha/beta hydrolase fold; 2-oxoglutarate dehydrogenase E1 component (EC: 1.2.4.2) | Lipases and LCFA | 9181 |
| RTO4_10002 | arylacetamide deacetylase; alpha/beta hydrolase fold | Lipases and LCFA | 10002 |
| RTO4_11473 | arylacetamide deacetylase; alpha/beta hydrolase fold | Lipases and LCFA | 11473 |
| RTO4_11568 | arylacetamide deacetylase; alpha/beta hydrolase fold | Lipases and LCFA | 11568 |

TABLE 1-continued

List of genes and Protein Id

| Abbreviation | Annotation | Group | Protein Id |
|---|---|---|---|
| RTO4_14459 | arylacetamide deacetylase; triacylglycerol lipase (EC:3.1.1.3) | Lipases and LCFA | 14459 |
| RTO4 14706 | arylacetamide deacetylase; alpha/beta hydrolase fold | Lipases and LCFA | 14706 |
| RTO4_16608 | arylacetamide deacetylase; alpha/beta hydrolase fold | Lipases and LCFA | 16608 |
| RTO4_11739 | predicted lipase/calmodulin-binding heat-shock protein; DAGL sn1-specific diacylglycerol lipase | Lipases and LCFA | 11739 |
| RTO4_15065 | hormone-sensitive lipase (HSL) | Lipases and LCFA | 15065 |
| MGLL | lysophospholipase; acylglycerol lipase (EC:3.1.1.23) | Lipases and LCFA | 14158 |
| YJU3 | lysophospholipase; acylglycerol lipase (EC:3.1.1.23) | Lipases and LCFA | 9728 |
| Faa2-1 | long-chain acyl-CoA synthetase (AMP-forming) | Lipases and LCFA | 12538 |
| Faa2-2 | long-chain acyl-CoA synthetase (AMP-forming); long-chain-fatty-acid - CoA ligase (EC:6.2.1.3) | Lipases and LCFA | 12555 |
| Faa1-1 | acyl-CoA synthetase | Lipases and LCFA | 15746 |
| Faa1-2 | acyl-CoA synthetase; long-chain-fatty-acid---CoA ligase (EC:6.2.1.3) | Lipases and LCFA | 11167 |
| Faa1-3 | acyl-CoA synthetase; long-chain-fatty-acid---CoA ligase (EC:6.2.1.3) | Lipases and LCFA | 15748 |

Example 4: Further Mutants for Increasing Fatty Alcohol Production

The host cell can include one, two, or more gene modifications to promote fatty alcohol (FOH) production. Such gene modification can result in overexpression, under expression, or no expression of the target gene. Expression, including overexpression, of the target gene can include insertion of the gene using a plasmid, in which expression can include use of a promoter (e.g., an inducible promoter). To reduce or remove expression, the target gene can be removed or modified.

FIG. 12 shows FOH production in various strains that overexpress particular target genes, and Table 2 provides a list of these target genes. Such targets can include proteins that are implicated in increasing acetyl-CoA, NADPH (nicotinamide adenine dinucleotide phosphate), and/or fatty-acyl-CoA production. In Table 2, sources include the JGI's genome assembly for Rhodosporidium toruloides (accessed at mycocosm.jgi.doe.gov/Rhoto_IFO0880_4/Rhoto_IF00880_4.home.html), in which proteins are provided as RTO4_XXX and XXX indicates the protein ID. Also provided are RefSeq numbers (accessed at ncbi.nlm.nih.gov/protein) and UniProtKB numbers (accessed at uniprot.org).

TABLE 2

List of genes in FIG. 12

| Abbreviation | Annotation | Source |
|---|---|---|
| PDC | pyruvate decarboxylase | RTO4_15791 |
| ALD | aldehyde dehydrogenase (NAD+) | RTO4_12042 |
| ACS1 | acetyl-CoA synthetase | RTO4_14597 |
| Cat2 | carnitine O-acetyltransferase | RT04_14245 |
| ScCat2 | carnitine O-acetyltransferase, mitochondrial | UniProtKB No. P32796 |
| ACL | ATP citrate (pro-S)-lyase | RTO4_9726 |
| ME | malate dehydrogenase (oxaloacetate-decarboxylating) (NADP+) | RTO4_12761 |
| IDH | isocitrate dehydrogenase | RTO4_11129 |
| NNT_human | NAD(P) transhydrogenase, mitochondrial | UniProtKB No. Q13423 |
| NNT_A_aegypti | proton-translocating NAD(P)(+) transhydrogenase | RefSeqNo. XP_001662741.2; UniProtKB No. Q16LL0 |
| NNT_H_leucocephalus | proton-translocating NAD(P)(+) transhydrogenase | RefSeqNo. XP_009919164.1; UniProtKB No. A0A091Q7M4 |
| NNT_G_trabeum | Proton-translocating NAD(P)(+) transhydrogenase | RefSeqNo. XP_007863552.1; UniProtKB No. S7QGM1 |
| EcfadD | long-chain-fatty-acid-CoA ligase | UniProtKB No. P69451 |
| FAA3 | long-chain acyl-CoA synthetase | RTO4_12555 |
| FAA2 | long-chain acyl-CoA synthetase | RTO4_11167 |
| FAA2-2 | long-chain acyl-CoA synthetase | RTO4_15748 |

TABLE 2-continued

List of genes in FIG. 12

| Abbreviation | Annotation | Source |
| --- | --- | --- |
| FAA3_Nc | long-chain acyl-CoA synthetases (AMP-forming) | RTO4_12538 |
| Lip_Rt_8386 | arylacetamide deacetylase | RTO4_8386 |
| TGL2_S288C | triacylglycerol lipase 2 | UniProtKB No. P54857 |
| Lip_Tlanuginosus | lipase | UniProtKB No. O59952 |
| Lip_Mouse | patatin-like phospholipase domain-containing protein 2 | UniProtKB No. Q8BJ56 |
| Lip_Creinhardtii | Lipase-3 domain-containing protein | JGI Phytosome Cre09.g390615; UniProtKB No. A0A2K3DE56 |
| Lip_human | hormone-sensitive lipase | UniProtKB No. Q05469-2 (without tag) |
| Lip_human_tag3 | hormone-sensitive lipase | UniProtKB No. Q05469-2 (with tag at the C-terminus) |
| Lip_human_tag5 | hormone-sensitive lipase | UniProtKB No. Q05469-2 (with tag at the N-terminus) |
| Rt_Lip_15065 | hormone-sensitive lipase | RTO4_15065 |
| Rt_Lip_8919 | arylacetamide deacetylase | RTO4_8919 |
| Rt_Lip_9374 | predicted lipase | RTO4_9374 |
| Rt_Lip_10393 | Superfamily SSF53474 protein (alpha/beta-hydrolases) | RTO4_10393 |
| Rt_Lip_8386 | arylacetamide deacetylase | RTO4_8386 |
| Rt_Lip_12712 | Superfamily SSF53474 protein (secretory lipase) | RTO4_12712 |
| SCD | stearoyl-CoA desaturase | RTO4_9730 |
| ACC | acetyl-CoA carboxylase/biotin carboxylase 1 | RTO4_8639 |
| Stacked FAR | NAD-dependent epimerase/ dehydratase | Multiple copies of FAR (RefSeq No. YP_959486.1) |
| FAR | NAD-dependent epimerase/ dehydratase | Parent strain expressing FAR (RefSeq No. YP_959486.1) |

Knock-out strains were also characterized. FIG. 13 shows FOH production in various knock-out strains that lack particular target genes. Such targets can include proteins that are implicated in triacylglyceride (TAG) biosynthesis, β-oxidation of fatty acid molecules, and other processes. FIG. 14 shows single knock-out of a target gene, as well as multiple knock-out of two target genes. Multi-knock-out strains can be developed to further enhance FOH production, and the present disclosure encompasses strains having a plurality of mutant genes, in which each gene encodes a different target protein. Non-limiting target proteins can be any combination of proteins described herein.

Example 5: Effect of Culture Conditions on Fatty Alcohol Production

FIG. 15 shows the effect of culture conditions of fatty alcohol (FOH) production for the NCS2 mutant strain (indicated as "STC0179"), its parental strain (indicated as "STC0113"), and STC0180. The culture can include various media, including DMR hydrolysate media or "mock DMR" media having entirely synthetic components to simulate the composition of a corn stover hydrolysate. As can be seen in FIG. 15, the type of culture media and concentration of nitrogen within the culture can affect FOH production. Such differences can be controlled by using host cells having low catabolism of FOH, in which such catabolism may be influenced by minor components of the media (e.g., trace metals and byproducts of the biomass hydrolysis process).

The effect of culture conditions was also assessed for different single knock-out and multi-knock-out strains. These strains included deletion of a fatty alcohol oxidase (RTO4_10253, FAO1) and/or an aldehyde dehydrogenase (RTO4_16323, HFD1) in a strain expressing fatty alcohol reductase (Maq_2220). The strain displayed dramatically reduced growth on fatty alcohols as a sole carbon source (~90% reduction in growth rate on 1-hexadecanol, demonstrating that we did indeed disrupt fatty alcohol catabolism) and significantly increased fatty alcohol production (2-4 fold depending on condition tested) (FIGS. 16A-16B and FIGS. 17A-17B).

The defined media (indicated as "Mock" in FIG. 16B and FIG. 17B) included Difco™ Yeast Nitrogen Base (YNB) without amino acids (includes a long list of trace elements and some vitamins like thiamine and 5 g/L ammonium sulfate) plus Complete Supplement Mix (CSM, several amino acids and some nucleotides, from Sunrise Science Products, Inc., Knoxville, Tenn.) plus 100 mM potassium phosphate plus 75 g/L glucose plus 40 g/L xylose.

Notably, fatty alcohol production was more consistent between media conditions than for the parental strain, consistent with our hypothesis that variation in fatty alcohol production between those conditions can be strongly influenced by variation in fatty alcohol catabolism.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

CONCLUSION

Although the foregoing embodiments have been described in some detail for purposes of clarity of understanding, it will be apparent that certain changes and modifications may be practiced within the scope of the appended claims. It should be noted that there are many alternative ways of implementing the processes, systems, and apparatus of the present embodiments. Accordingly, the present embodiments are to be considered as illustrative and not restrictive, and the embodiments are not to be limited to the details given herein.

The invention claimed is:

1. An isolated, genetically engineered host cell comprising:
a first mutant gene that is a deletion of a gene encoding a cytoplasmic tRNA thiolation protein; and
one or more expressed nucleic acids encoding 1) a fatty acyl-CoA reductase, or 2) a thioesterase, a carboxylicacid reductase and an aldehyde reductase.

2. The host cell of claim 1, wherein the cytoplasmic tRNA thiolation protein is cytoplasmic tRNA 2-thiolation protein 2.

3. The host cell of claim 1 wherein the cytoplasmic tRNA thiolation protein comprises a polypeptide sequence having at least 90% sequence identity to any one of the following SEQ ID NOs: 1, 3-8, 10-16 and 18-20.

4. The host cell of claim 1, wherein the engineered host cell further comprises a second mutant gene comprising insertion of a nucleic acid encoding an acetyl-CoA carboxylase, thereby providing overexpression of the acetyl-CoA carboxylase.

5. The host cell of claim 4, wherein the acetyl-CoA carboxylase comprises a polypeptide sequence having at least 90% sequence identity to SEQ ID NO:30.

6. The host cell of claim 1, wherein the engineered host cell further comprises a second mutant gene comprising deletion of a nucleic acid encoding a lysophospholipid acyltransferase, a fatty alcohol oxidase, an aldehyde dehydrogenase, an isocitrate dehydrogenase, or a pyruvate decarboxylase.

7. The host cell of claim 6, wherein the lysophospholipid acyltransferase comprises a polypeptide sequence having at least 90% sequence identity to SEQ ID NO: 31; the fatty alcohol oxidase comprises a polypeptide sequence having at least 90% sequence identity to SEQ ID NO: 32; the aldehyde dehydrogenase comprises a polypeptide sequence having at least 90% sequence identity to SEQ ID NO: 33 or SEQ ID NO: 36; the isocitrate dehydrogenase comprises a polypeptide sequence having at least 90% sequence identity to SEQ ID NO: 34; or the pyruvate decarboxylase comprises a polypeptide sequence having at least 90% sequence identity to SEQ ID NO: 35.

8. A method of producing a fatty alcohol, the method comprising:
incubating an isolated, genetically engineered host cell in a culture; and
isolating one or more fatty alcohols from the culture,
wherein the genetically engineered host cell comprises a first mutant gene that is a deletion of a gene encoding a cytoplasmic tRNA thiolation protein, and further one or more expressed nucleic acids encoding 1) a fatty acyl-CoA reductase, or 2) a thioesterase, a carboxylic acid reductase and an aldehyde reductase.

9. The method of claim 8, said incubating comprises 0 to 2 µM of zinc, 0 to 20 µM of cobalt, 0 to 20 µM of copper and/or 0.5 to 5 g/L ammonium in the culture.

10. The method of claim 8, wherein the host cell provides an increased amount of the one or more fatty alcohols, as compared to a corresponding control cell lacking deletion of the first mutant gene.

11. The method of claim 8, wherein the cytoplasmic tRNA thiolation protein is cytoplasmic tRNA 2-thiolation protein 2.

12. The method of claim 8, wherein the cytoplasmic tRNA thiolation protein comprises a polypeptide sequence having at least 90% sequence identity to any one of the following SEQ ID NOs: 1, 3-8, 10-16 and 18-20.

13. The method of claim 8, wherein the host cell further comprises a second mutant gene comprising insertion of a nucleic acid encoding an acetyl-CoA carboxylase or a fatty alcohol reductase, thereby providing overexpression of the acetyl-CoA carboxylase or overexpression of the fatty alcohol reductase.

14. The method of claim 8, wherein the host cell further comprises a second mutant gene comprising deletion of a nucleic acid encoding a lysophospholipid acyltransferase, a fatty alcohol oxidase, an aldehyde dehydrogenase, an isocitrate dehydrogenase, or a pyruvate decarboxylase.

15. The method of claim 8, wherein the fatty alcohol comprises a structure of R'OH, in which R' is a C4-32 aliphatic that is optionally substituted.

\* \* \* \* \*

SEQUENCE LISTING

```
<160> NUMBER OF SEQ ID NOS: 36

<210> SEQ ID NO 1
<211> LENGTH: 612
<212> TYPE: PRT
<213> ORGANISM: Rhodosporidium toruloides

<400> SEQUENCE: 1
```

| Met | Ser | Cys | Ser | Gln | Pro | Gln | Asp | Asp | Gly | Ala | Ala | Pro | Glu | Gln |
|---|---|---|---|---|---|---|---|---|---|---|---|---|---|---|
| 1 | | | | 5 | | | | | 10 | | | | | 15 |
| Pro | Val | His | Ala | Pro | Gln | His | Cys | Ala | Arg | Cys | Ala | Leu | Pro | Pro | Thr |
| | | | 20 | | | | | 25 | | | | | 30 | | |
| Val | Val | Ala | Arg | Gly | Thr | Ala | Tyr | Cys | Asp | Asp | His | Phe | Thr | Gln | Ser |
| | | | 35 | | | | 40 | | | | | 45 | | | |
| Leu | Ala | Ser | Arg | Phe | Arg | Arg | Gly | Thr | Asp | Gly | Ala | Arg | Leu | Tyr | Ala |
| | 50 | | | | | 55 | | | | | 60 | | | | |
| Glu | Lys | Gly | Arg | Glu | Thr | Tyr | Glu | Gly | Phe | Ala | Gly | Thr | Ser | Asp | Gly |
| 65 | | | | | 70 | | | | | 75 | | | | | 80 |
| Ala | Ala | Arg | Arg | Asp | Ala | Arg | Arg | Ser | Glu | Ala | Asn | Gly | Ser | Glu | Arg |
| | | | | 85 | | | | | 90 | | | | | 95 | |
| Thr | Thr | Arg | Leu | Val | Val | Ala | Phe | Ser | Gly | Gly | Cys | Ser | Ser | Arg | Thr |
| | | | | 100 | | | | | 105 | | | | | 110 | |
| Leu | Leu | Asp | Leu | Val | Lys | Thr | Thr | Tyr | Phe | Ser | His | Leu | Leu | Pro | Ser |
| | | | 115 | | | | | 120 | | | | | 125 | | |
| Ser | Ala | Ser | Ser | Glu | Leu | Thr | Ser | Ala | Thr | Asn | Gly | Lys | Gly | Lys | Gly |
| | | 130 | | | | | 135 | | | | | 140 | | | |
| Lys | Lys | His | Gly | Leu | Pro | Arg | Arg | Pro | Val | Phe | Ala | Glu | Leu | Glu | Val |
| 145 | | | | | 150 | | | | | 155 | | | | | 160 |
| Val | Phe | Val | Asp | Glu | Ser | Ser | Val | Pro | Gly | Glu | Val | Asp | Ala | Thr | Ala |
| | | | | 165 | | | | | 170 | | | | | 175 | |
| Asp | Phe | Arg | Arg | Ile | Val | Gln | Gly | Ala | Thr | Pro | Phe | Ala | Arg | Phe | Thr |
| | | | 180 | | | | | 185 | | | | | 190 | | |
| Ala | Leu | Arg | Leu | Glu | Asp | Val | Phe | Ala | Ser | Ala | Tyr | Ser | Ser | Ala | Leu |
| | | | 195 | | | | | 200 | | | | | 205 | | |
| Pro | Leu | Ser | Val | Ser | Thr | Val | Ala | Pro | Ser | Leu | Pro | Val | Ile | Pro | Pro |
| | | 210 | | | | | 215 | | | | | 220 | | | |
| Ser | Ala | Ser | Ala | Ser | Ala | Ser | Ser | Thr | Asp | Asn | Ser | Asp | Ser | Arg | Arg |
| 225 | | | | | 230 | | | | | 235 | | | | | 240 |
| Thr | His | Leu | Val | Ser | Leu | Leu | Ser | Tyr | Pro | Ser | Leu | Ser | Pro | Thr | Ser |
| | | | | 245 | | | | | 250 | | | | | 255 | |
| Leu | Ala | Ser | Leu | Arg | Thr | Ala | Leu | Arg | Ser | Ser | Leu | Ile | Leu | Ser | His |
| | | | 260 | | | | | 265 | | | | | 270 | | |
| Val | Arg | His | Ser | Ser | Ser | Ser | Thr | Ala | Val | Leu | Leu | Leu | Gly | Asp | Ser |
| | | | 275 | | | | | 280 | | | | | 285 | | |
| Gly | Thr | Arg | Ser | Ala | Ile | Thr | Thr | Leu | Ser | Gly | Met | Ser | Leu | Gly | Arg |
| | | 290 | | | | | 295 | | | | | 300 | | | |
| Gly | Phe | Ser | Ile | Gly | Glu | Glu | Ser | Gly | Ala | Glu | Tyr | Leu | Ala | Val | Ser |
| 305 | | | | | 310 | | | | | 315 | | | | | 320 |

```
Arg Asp Glu Ala Val Thr Ala Asp Gly Gln Lys Ser Ala Gly Glu
            325                 330                 335

Val Leu Val Val Arg Pro Leu Val His Ala Thr Leu Gly Glu Val Glu
        340                 345                 350

His Tyr Cys Asn Leu Met Gly Leu Glu Thr Leu Trp Ala Gln Lys Arg
            355                 360                 365

Ser Ala Ala Glu Glu Ser Ala Lys Lys Lys Thr Ile Gln Gly Leu Val
        370                 375                 380

Glu Asp Phe Ile Leu Ser Leu Glu Ser Thr Phe Pro Ser Thr Val Ser
385                 390                 395                 400

Thr Val Thr Arg Thr Ser His Lys Leu Gly Leu Arg Ser Ser His Ala
            405                 410                 415

Ser Phe Leu Ala Ser Gln Ala Arg Ser Arg Pro Thr Ala Pro Leu Glu
        420                 425                 430

Thr Ala Ser Leu Cys Pro Val Cys Gly Leu Pro Ala Pro Glu Arg Gly
            435                 440                 445

Gln Ala Glu Ser Trp Arg Glu Thr Ile Ala Ile Ser Asn Leu Gln Ala
        450                 455                 460

Val Leu Arg Ala Glu Gly Ala Gly Ala Asp Ala Thr Leu Arg Thr Thr
465                 470                 475                 480

Gly Glu Glu Gly Ile Glu Ala Arg Arg Lys Pro Tyr Glu Pro Ser Lys
            485                 490                 495

Ala His Leu Leu Asp Pro Ala Gly Val Ala Gly Glu Ala Val Ala Asn
        500                 505                 510

Gly Asp Ala Pro Thr Ser Ser Ala Pro Thr Thr Asp Asp Ala Gly
            515                 520                 525

Pro Leu Leu Ala Pro Tyr Leu Cys Tyr Gly Cys Leu Ile Ala Leu Ser
530                 535                 540

Ser Ser Ser Ser Ala Ala Ala Lys Lys Pro Ser Ser Thr Ser Ser Thr
545                 550                 555                 560

Leu Val Leu Pro Pro Tyr Val Gln Gly Ala Leu Arg Ser Arg Val Glu
            565                 570                 575

Arg Asp Gln Gly Ile Val Gly Lys Lys Glu Leu Arg Ser Glu Glu Asp
        580                 585                 590

Leu Arg Arg Glu Val Glu Glu Phe Leu Leu Asp Asp Glu Gly Asp Arg
            595                 600                 605

Ala Glu Ala Val
        610

<210> SEQ ID NO 2
<211> LENGTH: 515
<212> TYPE: PRT
<213> ORGANISM: Homo sapiens

<400> SEQUENCE: 2

Met Cys Gln Val Gly Glu Asp Tyr Gly Glu Pro Ala Pro Glu Glu Pro
1               5                   10                  15

Pro Pro Ala Pro Arg Pro Ser Arg Glu Gln Lys Cys Val Lys Cys Lys
            20                  25                  30

Glu Ala Gln Pro Val Val Ile Arg Ala Gly Asp Ala Phe Cys Arg
            35                  40                  45

Asp Cys Phe Lys Ala Phe Tyr Val His Lys Phe Arg Ala Met Leu Gly
        50                  55                  60

Lys Asn Arg Leu Ile Phe Pro Gly Glu Lys Val Leu Leu Ala Trp Ser
```

```
                65                  70                  75                  80
        Gly Gly Pro Ser Ser Ser Met Val Trp Gln Val Leu Glu Gly Leu
                        85                  90                  95

Ser Gln Asp Ser Ala Lys Arg Leu Arg Phe Val Ala Gly Val Ile Phe
                       100                 105                 110

Val Asp Glu Gly Ala Ala Cys Gly Gln Ser Leu Glu Arg Ser Lys
                       115                 120                 125

Thr Leu Ala Glu Val Lys Pro Ile Leu Gln Ala Thr Gly Phe Pro Trp
        130                 135                 140

His Val Ala Leu Glu Glu Val Phe Ser Leu Pro Pro Ser Val Leu
        145                 150                 155                 160

Trp Cys Ser Ala Gln Glu Leu Val Gly Ser Glu Gly Ala Tyr Lys Ala
                        165                 170                 175

Ala Val Asp Ser Phe Leu Gln Gln His Val Leu Gly Ala Gly Gly
                       180                 185                 190

Gly Pro Gly Pro Thr Gln Gly Glu Gln Pro Pro Gln Pro Pro Leu
                       195                 200                 205

Asp Pro Gln Asn Leu Ala Arg Pro Pro Ala Pro Ala Gln Thr Glu Ala
        210                 215                 220

Leu Ser Gln Leu Phe Cys Ser Val Arg Thr Leu Thr Ala Lys Glu Glu
        225                 230                 235                 240

Leu Leu Gln Thr Leu Arg Thr His Leu Ile Leu His Met Ala Arg Ala
                       245                 250                 255

His Gly Tyr Ser Lys Val Met Thr Gly Asp Ser Cys Thr Arg Leu Ala
                       260                 265                 270

Ile Lys Leu Met Thr Asn Leu Ala Leu Gly Arg Gly Ala Phe Leu Ala
                       275                 280                 285

Trp Asp Thr Gly Phe Ser Asp Glu Arg His Gly Asp Val Val Val
                       290                 295                 300

Arg Pro Met Arg Asp His Thr Leu Lys Glu Val Ala Phe Tyr Asn Arg
        305                 310                 315                 320

Leu Phe Ser Val Pro Ser Val Phe Thr Pro Ala Val Asp Thr Lys Ala
                       325                 330                 335

Pro Glu Lys Ala Ser Ile His Arg Leu Met Glu Ala Phe Ile Leu Arg
                       340                 345                 350

Leu Gln Thr Gln Phe Pro Ser Thr Val Ser Thr Val Tyr Arg Thr Ser
                       355                 360                 365

Glu Lys Leu Val Lys Gly Pro Arg Asp Gly Pro Ala Ala Gly Asp Ser
                       370                 375                 380

Gly Pro Arg Cys Leu Leu Cys Met Cys Ala Leu Asp Val Asp Ala Ala
        385                 390                 395                 400

Asp Ser Ala Thr Ala Phe Gly Ala Gln Thr Ser Ser Arg Leu Ser Gln
                       405                 410                 415

Met Gln Ser Pro Ile Pro Leu Thr Glu Thr Arg Thr Pro Pro Gly Pro
                       420                 425                 430

Cys Cys Ser Pro Gly Val Gly Trp Ala Gln Arg Cys Gly Gln Gly Ala
                       435                 440                 445

Cys Arg Arg Glu Asp Pro Gln Ala Cys Ile Glu Gln Leu Cys Tyr
                       450                 455                 460

Ser Cys Arg Val Asn Met Lys Asp Leu Pro Ser Leu Asp Pro Leu Pro
        465                 470                 475                 480

Pro Tyr Ile Leu Ala Glu Ala Gln Leu Arg Thr Gln Arg Ala Trp Gly
                       485                 490                 495
```

```
Leu Gln Glu Ile Arg Asp Cys Leu Ile Glu Asp Ser Asp Asp Glu Ala
                500                 505                 510

Gly Gln Ser
        515

<210> SEQ ID NO 3
<211> LENGTH: 510
<212> TYPE: PRT
<213> ORGANISM: Cryptococcus neoromans

<400> SEQUENCE: 3

Met Ala Phe Val Thr Lys Arg Thr Cys Phe Glu Ala Ala Val Phe Ser
1               5                   10                  15

Arg Phe Thr Lys Ser Leu His Pro Pro Leu Lys Ser Pro Thr Ser Ser
            20                  25                  30

Arg Ser Ala Ala Ser Ser Gly Tyr Arg Pro Ala Gln Ser Gly Ser
        35                  40                  45

Ala Leu Ile Ala Leu Ser Thr Gly Cys Gly Ser Thr Thr Leu Leu Asp
    50                  55                  60

Leu Leu Leu Thr Arg Arg Tyr Ile Gly Lys Gly Asp Asp Arg Val Val
65                  70                  75                  80

Asp Lys Thr Lys Gly Glu Lys Glu Pro Val Trp Arg Lys Gly Trp Val
                85                  90                  95

Cys Tyr Val Asp Phe Ser Ser Val Gly Glu Ile Glu Arg Gln Gly
            100                 105                 110

Glu Gly Gln Gly Gln Arg Glu Gly Ser Arg Met Glu Gly Val Lys Lys
            115                 120                 125

Trp Val Glu Gly Arg Glu Asn Gly Leu Gly Trp Val Gly Leu Arg Ala
    130                 135                 140

Glu Asp Val Phe Asp Arg Gly Leu Arg Asn Arg Leu Arg Leu Leu Ala
145                 150                 155                 160

Gly Leu Pro Ile Arg Asp Asp Lys Gln Glu Val Ala Ala Gln Trp Ala
                165                 170                 175

Val Asp Leu Lys Asp His Ala Leu Pro Leu Ser Ser Pro Ser Ser Ser
            180                 185                 190

Ser Ser Pro Ser Pro Thr Pro Leu Thr His Leu Arg Asn Leu Leu Ser
        195                 200                 205

Ser Leu Pro Pro Ser Ser Arg Pro Gln Leu Leu Ser His Ile Leu Ser
    210                 215                 220

Ser Leu Leu Thr Thr Val Ala His Thr Leu Pro His Ile Ser His Val
225                 230                 235                 240

Leu Met Gly Glu Thr Ser Thr Arg Gln Ala Glu Arg Leu Ile Ser Gly
                245                 250                 255

Thr Ala Leu Gly Arg Gly Trp Gln Leu Pro Leu Glu Leu Ala Ala Val
            260                 265                 270

Arg Ala Glu Pro Ala Leu Ser Ser Leu Glu His Leu Ile Thr Ser Ala
        275                 280                 285

Glu Ala Glu Ala Glu Gly Glu Asn Lys Glu Asn Ile Gly Phe Thr Trp
    290                 295                 300

Leu Lys Pro Met Ser Asp Leu Thr Ala Lys Glu Ala Ala Ile Tyr Cys
305                 310                 315                 320

His Leu Arg Ser Leu Ser Ser Phe Thr Tyr Asn Ala Arg His Trp Asp
                325                 330                 335

Ser Ala Gly Pro Pro Pro Ala Ala Gly Lys Thr Lys Gly Gly Val Lys
```

```
               340                 345                 350
Ser Leu Glu Met Leu Thr Glu Asn Phe Ile Ala Gly Leu Gly Ala Ser
        355                 360                 365

His Pro Ala Thr Val Ser Thr Ile Asn Arg Thr Gly Ala Lys Leu Val
    370                 375                 380

Phe Pro Gly Lys Glu Glu Asp Arg Pro Tyr Cys Pro Val Cys Gln Met
385                 390                 395                 400

Pro Val Asp Pro Ser Ala Leu Glu Trp Lys Ser Arg Thr Ala Leu Thr
                405                 410                 415

Phe Leu Ser Thr Lys Thr Glu Pro Thr Ala Ile Ser Lys Gln Gln Gln
            420                 425                 430

Pro Gln His Gly Glu Thr Glu Ala Leu Ala Pro Leu Leu Cys Tyr Ser
        435                 440                 445

Cys Leu Thr Thr Leu Thr Pro Pro Thr Val Val Ser Lys Ala Lys Ala
    450                 455                 460

Lys Ala Gln Thr Ala Gly Leu Thr Val Asn Gly Asp Glu Pro Val Leu
465                 470                 475                 480

Leu Pro Val Trp Val Asn Glu Gly Val Lys Arg Gln Met Gly Arg
                485                 490                 495

Arg Glu Met Lys Asp Glu Ile Lys Glu Phe Leu Ile Glu Glu
            500                 505                 510

<210> SEQ ID NO 4
<211> LENGTH: 687
<212> TYPE: PRT
<213> ORGANISM: Ustilago maydis

<400> SEQUENCE: 4

Met Pro Cys Pro Gln Pro Asp Asp Pro Pro Ser Asp Ala Val Thr
1               5                   10                  15

Ala His Gly Thr His Pro Ser Thr Thr Cys Val Arg Cys Lys Thr Asn
                20                  25                  30

Pro Ala Ile Thr Ile Leu Arg Asp Ser Ile Tyr Cys Gln Ala Cys Ala
            35                  40                  45

Leu Ala Val Phe Tyr Gln Lys Ala Lys Ala Gly Leu Glu Tyr Ala Arg
        50                  55                  60

Gly Ala Gly Leu Ser Lys Tyr Val Ala Ala Lys Ala Ala Ser Ser
65                  70                  75                  80

Ala Ala Gly Ser Pro Ala Glu Ser Arg Gln Thr Phe Ser Ser Thr
                85                  90                  95

Ser Thr Phe Pro Pro Ala Ala Asn Gly Glu Ala Thr Thr Lys Arg Arg
            100                 105                 110

Ile Lys His Val Ser Asn Gly Ser Gly Asn Ala Glu Glu Asn Val Ser
        115                 120                 125

Ala Asn Ile Ala Ile Ala Phe Ser Gly Gly Ile Ser Ser Arg Ala Leu
    130                 135                 140

Leu Arg Ser Ala Thr Gln Tyr Phe Arg Pro Ala Thr Ala Phe Thr Asn
145                 150                 155                 160

Arg Asp Thr Arg Arg Lys Ala Arg Gly Gln Val Val Asp Ser Asn
                165                 170                 175

Asn Asn Asp Asn Asp Ser Gly Thr Ala Ser Ile Ser Ser Lys Ser Met
            180                 185                 190

Arg Gly Ala Ser Thr Ala Ala Gly Arg Phe Asn Glu Val Gly Lys Ile
        195                 200                 205
```

-continued

```
Tyr Val Phe Tyr Ile Asp Asp Ser Ala Val Val Pro Asn Gly Val Asp
        210             215                 220
Arg Thr Glu Gln Ala Arg Arg Met Val Glu Glu Glu Gly Cys Ala Asp
225                 230                 235                 240
Leu His Phe Val Gly Leu Lys Leu His Asp Val Phe Arg Ala Asp Asp
                245                 250                 255
Asp Gly Gly Phe Gln Gly Val Ala Trp Arg Ser Val Asp Val Asp His
            260                 265                 270
Gln Gln Val Ser Ala Ser Ile Ser Asp Val Ser Asp Pro Arg Gln Ala
                275                 280                 285
Leu Lys Asp Leu Phe Ser Ser Leu Cys Pro Val Asp Thr Pro Arg Thr
290                 295                 300
Gly Ala Ala Ser Ala Arg Thr Arg Ile Glu Asp Leu His Arg Ile Phe
305                 310                 315                 320
Ile Ser Thr Leu Leu Arg Arg Thr Ala Lys Gln Tyr Asp Cys Ala Ala
                325                 330                 335
Leu Leu Leu Gly Asp Thr Ala Thr Arg Ile Ser Ile Arg Leu Ile Glu
                340                 345                 350
Asp Leu Ala Lys Gly Ala Gly His Lys Ile Pro Val Gln Gly Ser Asp
                355                 360                 365
Ala Ala Trp Ile Asp Asp Leu Leu Ile Val Arg Pro Leu Lys Thr His
        370                 375                 380
Leu Leu Gln Glu Val Val Phe Tyr Thr Ser Gln Leu Asn Leu Asp Pro
385                 390                 395                 400
Leu Gln Pro Glu Gln Pro Ile Val Ala Pro Thr Val Ser Thr Thr Gly
                405                 410                 415
Ile Leu Ala Ser Asn Ser Ser Thr Pro Ala Met Asp Lys Ser Ser Ile
                420                 425                 430
Ala Arg Leu Thr Glu Thr Phe Ile Leu Asn Leu Glu Lys Gly Val Pro
                435                 440                 445
Ser Thr Val Thr Thr Ile Gly Lys Thr Gly Ser Lys Leu Val Leu Asn
        450                 455                 460
Gly Ala Pro Gly Phe Pro Thr Thr Thr Trp Thr Asp Val Ala His Ser
465                 470                 475                 480
Thr Ser Ala Phe Arg Asp Val Gly Pro Ser Val Ser Leu Ser Ser Arg
                485                 490                 495
Leu Thr His Arg Met Ala Asn Val Thr Leu Ala Glu Thr Gln Cys Glu
                500                 505                 510
Pro Arg Ile Gly Ser Arg Gly Ile Lys Leu Ala Gln Leu Ser Ala Asn
                515                 520                 525
Cys Val Arg Trp Asn Ser Ile Asn Gly Cys Ala Leu Cys Ala Met Pro
        530                 535                 540
Ser Gln His Pro Lys Ala Arg Trp Trp Lys Arg Asp Ile Thr Ile Ser
545                 550                 555                 560
Ser Leu Ala Glu Thr Ala Pro Arg Ser Arg Gln Thr Val Glu Thr Gln
                565                 570                 575
Ala Thr Cys Gln Ser Ser Glu Gln Ala Asp Trp Leu Glu Leu Cys Asn
                580                 585                 590
His Leu Cys Tyr Ala Cys Leu Leu Val Leu Ser Pro Ala Ile Ser Ser
                595                 600                 605
Ala His Pro Ala Met Leu Pro Ser Thr Val Leu His His Ile His Arg
        610                 615                 620
Ser Thr His His Ala Gly Ala Gln His Pro His His Ile Ala Ser Arg
```

```
                    625                 630                 635                 640

Pro Leu Ala Asp Asp His Glu Leu Pro Pro Glu His Lys Thr Asn Gln
                    645                 650                 655

Ala Ala Cys Ala Thr His Asn Met Pro Asn Pro Ile Pro Gln Pro Leu
                    660                 665                 670

Lys Pro Ser Gln Ile Lys Ala His Ile Ser Glu Phe Leu Ile Glu
                    675                 680                 685

<210> SEQ ID NO 5
<211> LENGTH: 366
<212> TYPE: PRT
<213> ORGANISM: Schizosaccharomyces pombe

<400> SEQUENCE: 5

Met Gln Asn Thr Ala Leu Asp Asn Ser Ala Asp Ser Lys Cys Ser Lys
1               5                   10                  15

Cys Asp Asn Lys Ala Thr Val Leu Thr Lys Ser Asp Ala Val Cys Asp
                20                  25                  30

Ser Cys Phe Val Arg Arg Ile Glu Asn Lys Ile Arg Arg Gln Phe Glu
            35                  40                  45

Leu Val Arg Pro Asn Leu Gln Gly Arg Lys Ser Lys Arg Ala Met Leu
        50                  55                  60

Ala Ile Ser Gly Gly Ile Ser Ser Met Ala Met Leu Glu Thr Ala Asn
65                  70                  75                  80

Tyr Leu Ser Lys Tyr Arg Asp Asp Asn Tyr Arg Pro Met Phe Asp Glu
                85                  90                  95

Leu Leu Ala Val His Phe Gln Trp Gly Thr Asp Ser Ala Val Ala Lys
                100                 105                 110

Thr Ile Glu Glu Ser Ile Ser Lys Asn Tyr Pro Lys Cys Pro Phe Lys
            115                 120                 125

Val Ile Gly Glu Ala Glu Leu Leu Asn Arg Thr Ile Ala Thr Asp Ser
        130                 135                 140

Arg Gly Asn Ile Glu Ile Asn Ala Asp Asn Glu Lys Phe Asn Pro Glu
145                 150                 155                 160

Val Ile Ser Ser Leu Ala Ser Arg Gln Asp Leu Leu Tyr Arg Ile Arg
                165                 170                 175

Asp Lys Leu Leu Val Ser Tyr Ala Arg Lys Ala Asn Cys Asp Thr Ile
                180                 185                 190

Val Phe Gly Asp Ser Gly Thr Thr Ile Ala Ala Arg Val Leu Glu Leu
            195                 200                 205

Val Ala Glu Gly Arg Gly Phe Ala Ile Pro Trp Tyr Thr Ser Val Cys
        210                 215                 220

Ser Lys Leu Pro Asn Cys Asp Thr Phe Leu Leu Arg Pro Leu Arg Glu
225                 230                 235                 240

Val Leu Ser Ser Asp Leu Lys Ser Tyr Met Asn Ile Lys Gly Leu Ala
                245                 250                 255

Phe Cys Asp Ser Leu Ile Glu Ala Arg Pro Asn Thr Ile His Gly Val
                260                 265                 270

Thr Glu Ser Tyr Phe Ser Ser Leu Asn Asp Thr Phe Pro Ser Leu Val
            275                 280                 285

Ser Thr Val Val Lys Met Ser Ser Lys Leu His Val Pro Ser Thr Glu
        290                 295                 300

Ala Ile Cys Thr Ile Cys Asn Leu Pro Met Gln Glu Asp Ala Glu Thr
305                 310                 315                 320
```

```
Trp Leu Gln Lys Thr Thr Val Glu His Pro Asp Ser Val Glu Gly Ile
                325                 330                 335

Lys Asn Gln Asn Val Cys Tyr Gly Cys Ser Val Ser Leu Lys Ser Leu
            340                 345                 350

Lys Gly Thr Leu His Ile Pro Asp Ile Glu Lys Glu Gly Ile
        355                 360                 365

<210> SEQ ID NO 6
<211> LENGTH: 267
<212> TYPE: PRT
<213> ORGANISM: Rhodosporidium delemar

<400> SEQUENCE: 6

Met His Thr Leu Pro Asn Glu Lys Lys Ile Gln Val Val Pro Glu
1               5                   10                  15

Ala Ile Val Cys His Ile Asp Glu Ser Pro Leu Phe Asp Ala Met Asn
                20                  25                  30

Pro Ser Ser Ala Asp Leu Leu Arg Gln Arg Ile Glu Glu His Tyr Pro
            35                  40                  45

Asn Phe Glu Phe Ile Ser His Gly Leu Asp Asp Ile Phe Cys Pro Pro
        50                  55                  60

Phe Ser Thr Asp Thr Lys Ala Leu Arg Ser Phe Ala Gly Val Glu Asn
65                  70                  75                  80

Gly Asp Tyr Glu His Trp Val Gln Cys Ala Ser Lys Glu Thr Ala Ser
                85                  90                  95

Asp Arg Lys Arg Ser Leu Gln Ala Leu Phe Ser Ile Lys Lys Thr
            100                 105                 110

Thr Ala Lys Glu Asp Leu Leu Trp His Ile Lys Met Asp Met Leu Leu
        115                 120                 125

Thr Val Ala Arg Arg Glu Gly Cys Thr Tyr Ile Phe Phe Gly Asp Ser
    130                 135                 140

Ala Thr Arg Gln Ala Ile Lys Met Ile Ser Trp Thr Ala Lys Gly Arg
145                 150                 155                 160

Gly Tyr Ser Leu Pro Leu Asp Ile Ser Val Asp Asn Glu Leu Thr Phe
                165                 170                 175

Asp Val Gly Ile Met Arg Pro Met Lys Asp Met Leu Ser Lys Glu Ile
            180                 185                 190

Gly Leu Tyr Asn Tyr Phe Ser Gly Ile His Arg Leu Leu Leu Pro Pro
        195                 200                 205

Tyr Asn Phe Gly Thr Met Met Pro Ala Lys Ser Ser Ile Asp Arg Leu
    210                 215                 220

Thr Glu Gly Phe Ile Asn Arg Leu Glu Arg Glu Phe Pro Ser Thr Val
225                 230                 235                 240

Ser Thr Val Cys Arg Thr Thr Leu Lys Leu Thr Pro Ser Lys Asp Met
                245                 250                 255

Asp Tyr Gln Arg Ser Cys Ala Leu Cys Leu Met
            260                 265

<210> SEQ ID NO 7
<211> LENGTH: 452
<212> TYPE: PRT
<213> ORGANISM: Candida albicans

<400> SEQUENCE: 7

Met Pro Glu Ala Ile Val Tyr Leu Thr Glu Thr Glu Ile Cys Gln Lys
1               5                   10                  15
```

-continued

Cys Lys Thr Glu Asn Ala Val Val His Ala Arg Val Glu Lys Leu Cys
                20                  25                  30

Ser Asn Cys Tyr Ile Arg Phe Ile Arg Gly Lys Leu Arg Lys Gln Met
        35                  40                  45

His Asp Glu Arg Tyr Lys Val Lys Phe Gly Arg Ala Val Glu Gln Tyr
    50                  55                  60

Gly Thr Gln Arg Ile Leu Leu Ala Leu Ser Gly Glu Ser Ser Leu
65                  70                  75                  80

Val Leu Leu Asp Ile Phe Gly Ser Leu Leu Gln Glu Gln Asn Glu Leu
                85                  90                  95

His Lys Gly Lys Gln Gly Phe Glu Leu Val Val Asn Leu Asp Glu
            100                 105                 110

Tyr Glu Leu Asp Ser Leu Asn Asn Arg Ile Gln Lys Val Phe Pro Glu
            115                 120                 125

Leu Leu Ala Lys Tyr Gln Pro Val Lys Ile Ser Leu Asn Val Leu Ser
        130                 135                 140

Leu Asp Ser Tyr Val Asp Glu Glu Ser Leu His Arg Ile Leu Leu Thr
145                 150                 155                 160

Pro Asp Phe Arg Ala Met Ser Lys Ser Ile Asp Pro Thr Arg Val Thr
                165                 170                 175

Leu Thr Glu Ile Leu Arg Leu Cys Pro Asn Lys Ser Ser Ala Glu Asp
            180                 185                 190

Leu Leu Thr Ile Val Tyr Asn Asp Leu Ile Leu Arg Val Ala Ala Lys
        195                 200                 205

Glu Asp Cys Gln Thr Val Val Tyr Gly His Cys Met Thr Arg Leu Ala
210                 215                 220

Asn Glu Ile Ile Ala Leu Thr Val Lys Gly Arg Gly Ser Ile Ile His
225                 230                 235                 240

Lys Ser Ile Ala Asp His Thr Glu Thr Ile Asp Asp Lys Glu Ile Lys
                245                 250                 255

Val Met Phe Pro Leu Arg Glu Ile Leu Gln Ala Glu Ile Ser Ala Tyr
            260                 265                 270

Val Lys Leu Ala Glu Leu Asn Lys Tyr Val Ile Ser Ser Thr Val Gln
        275                 280                 285

Lys Ser Lys Ile Asn Lys Asn Leu Thr Ile Arg Asp Leu Thr Thr Asn
    290                 295                 300

Tyr Phe Lys Gln Leu Asp Ala Thr Gly Tyr Ala Ser Thr Ala Ser Thr
305                 310                 315                 320

Val Ala Lys Thr Gly Glu Lys Leu Gly Ser Pro Ser Asn Val Leu Cys
                325                 330                 335

Gln Cys Gln Ile Cys Gly Ala Asp Ile His Gln Asn Pro Ser Asn Trp
            340                 345                 350

Leu Lys Arg Ile Thr Val Thr Asp Pro Ala Ala Ile Thr Thr Asp Glu
        355                 360                 365

Glu Lys Glu Tyr Tyr Glu Met Phe Arg Ala Ser Leu Ser Pro Asp Asn
    370                 375                 380

Glu Asp Lys Asn Asn Ser Asp Ser Pro Ile Asp Ile Cys Phe Gly Cys
385                 390                 395                 400

Thr Val Thr Leu Gly Gly Val Lys Gly Asp Thr Gly Phe Ile Trp Pro
                405                 410                 415

Leu Gln Gly Ser Ser Glu Leu Lys Tyr Glu Tyr Arg Asn Asp Asn Gln
            420                 425                 430

Glu Lys Gln Lys Val Leu Asp Glu Phe Val Leu Thr Asp Asp Glu Gly

```
                435                 440                 445

Asp Ile Glu Val
    450

<210> SEQ ID NO 8
<211> LENGTH: 523
<212> TYPE: PRT
<213> ORGANISM: Dictyostelium discoideum

<400> SEQUENCE: 8

Met Ser Ser Glu Glu Leu Pro Ser Cys Gly Ile Asn Asp Asn Asp Ile
1               5                   10                  15

Asn Asn Thr Ile Pro Ile Asn Thr Arg Lys Val Gln Ile Ile Pro Asn
            20                  25                  30

Gly Asn Thr Gln Cys Val Lys Cys Leu Tyr Asn Val Ala Asn Asn Val
        35                  40                  45

Lys Asp Lys Lys Leu Ser Lys Lys Glu Lys Lys Glu Gln Lys Leu Lys
50                  55                  60

Glu Glu Glu Asn Asn Asn Asn Asn Glu Glu Pro Ile Thr Gln Gln
65                  70                  75                  80

Gln Lys Pro Ile Gly Lys Pro Ile Ile Asn Phe Arg Ser Glu Gln Leu
                85                  90                  95

Cys Trp Glu Cys Tyr Arg Glu Leu Ile Leu Lys Lys Phe Lys Leu Asn
            100                 105                 110

Ile Val Lys Val Arg Glu Ser Lys Arg Asp Ala Glu Lys Leu Leu Val
        115                 120                 125

Ala Leu Ser Gly Gly Thr Cys Ser Ser Met Leu Glu Leu Leu Lys
130                 135                 140

Gln Cys Thr Glu Gly Ser Gly Lys Ala Lys Met Phe Leu Asp Ile Lys
145                 150                 155                 160

Cys Val His Ile Asp Glu Ser Ser Ile Thr Pro Tyr Gln Asn His Asn
                165                 170                 175

Asp Thr Ile Glu Phe Leu Lys Glu Phe Asn Asn Val Lys Leu Gly Phe
            180                 185                 190

Pro Asn Leu Glu Ile Ile Pro Leu Glu Asp Ile Leu Gly Thr Val Thr
        195                 200                 205

Pro Leu Gly Glu Arg Thr Asn Gln Leu Lys Leu Gln Phe Ala Gln Leu
210                 215                 220

Ser Ser Glu Thr Ser Lys Glu Asp Leu Leu Leu Tyr Tyr Arg Asn Gln
225                 230                 235                 240

Leu Leu Ile Gln Val Ala His Lys Leu Asn Cys Lys Lys Val Ile Leu
                245                 250                 255

Gly Thr Ser Ser Asn Arg Leu Ala Val Gln Leu Val Ala Ser Thr Ser
            260                 265                 270

Lys Gly Arg Gly Phe Ser Val Pro Asn Glu Thr Ser Val Ile Ile Glu
        275                 280                 285

Gln Pro Ser Asn Asp Ile Lys Phe Tyr Gln Pro Met Arg Asp Phe Leu
290                 295                 300

Leu Lys Glu Ile Phe Ile Tyr Tyr Arg His Leu Asn Ile Leu Pro Val
305                 310                 315                 320

Pro Val Met Phe Ser Ile Leu Asn Leu Lys Pro Lys His Ser Ile Asn
                325                 330                 335

Thr Leu Cys Glu Asp Phe Leu His Cys Leu Gln Asp Ile Ser Asn Gln
            340                 345                 350
```

-continued

```
Thr Val His Thr Leu Leu Arg Ser Val Asp Lys Leu Ile Ser Pro Ser
            355                 360                 365
Ile Asp Ser Asn Tyr Asn Cys Ser Ile Cys Ser Ser Pro Leu Thr Ser
    370                 375                 380
Ala Glu Ile Lys Ser Leu Glu Lys Val Ile Leu Asp Asn Asn Asn Asn
385                 390                 395                 400
Ile Asn Lys Glu Asn Lys Asn Asn Asn Asn Asn Asn Asn Asn Asn Asn
                405                 410                 415
Asn Asn Asn Gly Cys Cys Ser Thr Thr Lys Thr Glu Asp Ser Ser Cys
            420                 425                 430
Cys Asn Lys Thr Glu Asp Asn Ser Ser Asn Asn Asn Asn Asn Asn Thr
            435                 440                 445
Gly Cys Cys Ser Ser Ser Ser Ser Thr Ser Thr Ser Ser Ile Thr Val
            450                 455                 460
Asn Lys Glu Thr Leu Cys Tyr Ser Cys Lys Ile Leu Tyr Arg Asp Phe
465                 470                 475                 480
Lys Ser Thr Pro Asn Ile Ala Pro Tyr Ile Lys Glu Asn Ser Lys Gln
                485                 490                 495
Leu Leu Thr Thr Ser Gln Leu Lys Asn Glu Ile Lys Asp Phe Leu Leu
            500                 505                 510
Asn Ser Asp Asp Asp Asp Asp Glu Asp Asn
            515                 520

<210> SEQ ID NO 9
<211> LENGTH: 405
<212> TYPE: PRT
<213> ORGANISM: Drosophila melanogaster

<400> SEQUENCE: 9

Met Cys Ser Ile Gly Glu Asp Asp Phe Gly Asp Glu Gly Ala Ala His
1               5                   10                  15
Ala Met Val Val Glu Ser Leu Pro Leu Gly Ile Val Leu Ser Pro Gly
                20                  25                  30
Asn Cys Ser Lys Cys Asp Val Asn Ser Gly Glu Leu Tyr Lys Leu Asn
            35                  40                  45
Phe Arg Thr Ala Glu Cys Arg Glu Cys Phe Leu Ala Tyr Ala Arg His
    50                  55                  60
Lys Phe Arg Ala Ala Leu Gly Ala Ala Lys Ile Leu Pro Arg Asn Ala
65                  70                  75                  80
Glu Val Leu Leu Val Leu Asp Gly Ser Ala Glu Ser Leu Val Leu Leu
                85                  90                  95
Asp Met Leu His Phe Ala Gln Thr Gln Asn Thr Phe Lys Arg Leu His
            100                 105                 110
Cys Asn Ala Arg Val Val Tyr Val Glu Glu Gln Val Gln Gly Arg
            115                 120                 125
Asp Pro Val Asp Leu Glu Ala Leu Gln Arg Leu Ser Thr Gln Tyr Ala
    130                 135                 140
Pro Phe Asp Phe Tyr Val Ile Glu Leu Gly Ala Leu Pro Ser Ser Leu
145                 150                 155                 160
Gln Arg Ile Lys Asp Tyr Ser Pro Phe Leu Asn Ala Asn Asn Glu Leu
                165                 170                 175
Ile His Lys Leu Gln Lys Leu Arg Ser Leu Thr Ala Arg Gln Asp Tyr
            180                 185                 190
Leu Gln Gln Gln Arg Lys Asn Leu Ile Cys Ser Val Ala Gln Cys Leu
            195                 200                 205
```

```
Gln Cys Thr His Val Phe Glu Ser Asn Ile Ser Val Asp Leu Ala Thr
    210                 215                 220

Gln Leu Leu Thr Ala Ile Ala Leu Gly Arg Gly Gly Ser Ala Ala Leu
225                 230                 235                 240

Asp Val Ala Leu Leu Asp Asp Arg Leu Ser Gly Asp Val Lys Leu Leu
                245                 250                 255

Arg Pro Leu Lys Asp Leu Thr Glu Gln Glu Ile Gln Phe Tyr Ile His
            260                 265                 270

Ala Gln Arg Leu Lys Pro His Phe Gln Lys Gly Ser Arg Tyr Gly Met
        275                 280                 285

Glu His Gly Glu Thr Ala Ser Leu Gln Asn Leu Thr Ser Ala Phe Val
    290                 295                 300

Ala Asn Leu Gln Gln Asn Phe Ala Ser Thr Val Ser Thr Val Phe Arg
305                 310                 315                 320

Thr Gly Asp Lys Ile Ala Val Asn Ser Asn Pro Glu Gln Ser Ser Cys
                325                 330                 335

Val His Cys Arg Ser Thr Leu Asp Ser Glu Leu Ser Asp Thr Leu Leu
            340                 345                 350

Ala Ile Glu Tyr Ser Arg Ser Val Ser Glu Ala Gly Val Ser Leu Tyr
        355                 360                 365

Lys Ser Gly Gln Asp Leu Glu Gly Leu Ala Lys Lys Arg Leu Glu Asn
    370                 375                 380

Lys Asp Gly Leu Cys His Ala Cys Arg Ala Ile Gln Thr Glu Leu Asp
385                 390                 395                 400

Ser Gly Asn Leu Leu
                405

<210> SEQ ID NO 10
<211> LENGTH: 325
<212> TYPE: PRT
<213> ORGANISM: Emericella nidulans

<400> SEQUENCE: 10

Met Glu Lys Tyr Arg Leu Arg Arg Asp Leu Pro Arg Ser Gly Pro Cys
1               5                   10                  15

Pro Val Leu Leu Pro Leu Ser Tyr Gly Leu Ser Ser Val Leu Leu
            20                  25                  30

His Met Val His Gly Gln Val Glu Arg Leu Leu Thr Lys Pro His Pro
                35                  40                  45

Pro Pro Gly Phe Glu Leu His Val Leu Ile Val Glu Pro Ser Ser Ile
    50                  55                  60

Ser Pro Ser Asn Pro Ser His Arg Gly Ala Phe Gln Leu Leu Gln
65                  70                  75                  80

Gln Phe Pro His Ala Ser Phe Thr Gln Leu Pro Leu His Ser Val Phe
                85                  90                  95

Asp Tyr Val Ser Gly Leu Asn Asp Ile Leu Ala Glu Tyr Val Gly Pro
            100                 105                 110

Ala Phe Val Asp Asp Thr Ser Leu Pro Ser Lys Glu Arg Leu Asp Ala
        115                 120                 125

Phe Arg Ala Ser Ile Thr Ser Ala Thr Ser Ala Ala Asp Val Asp Ser
    130                 135                 140

Val Leu Leu Asn Arg Leu Ile Ile Ala Phe Ala Arg Ser Leu Gly Cys
145                 150                 155                 160

Leu Gly Ile Ile Trp Gly Asp Ser Asp Asp Arg Leu Ala Ala Lys Thr
```

```
                  165                 170                 175
Leu Ala Asn Val Ser Lys Gly Arg Gly Ser Ser Leu Thr Trp Gln Val
                180                 185                 190

Ser Asp Gly Thr Ser Pro Phe Gly Leu Glu Phe Ser Phe Pro Leu Arg
            195                 200                 205

Asp Leu Phe Thr Ala Glu Leu Gln Ser Tyr Ala Asn Phe Phe Pro Glu
        210                 215                 220

Leu Leu Asn Ile Ile Pro Asp Gly Pro Leu Ser Asp Asn Ile Leu
225                 230                 235                 240

Thr Lys Asn Leu Ser Ile Asp Gln Leu Met Met Arg Tyr Val Ser Ser
                245                 250                 255

Gln Gly Ala Lys Tyr Pro Gly Val Met Ser Asn Val Thr Arg Thr Val
            260                 265                 270

Asn Lys Leu Glu Ser Ser Arg Met Ile Thr Asp Gly Leu Arg Cys Ala
        275                 280                 285

Leu Cys Asp Thr Phe Ile Cys Asn Pro Glu Gly Arg Gln Thr Met Asp
    290                 295                 300

Leu Glu Glu Arg Pro Thr Asn His Phe Cys Tyr Ala Cys Glu Arg Ser
305                 310                 315                 320

Arg Pro Gly Leu Ser
                325

<210> SEQ ID NO 11
<211> LENGTH: 518
<212> TYPE: PRT
<213> ORGANISM: Chlamydomonas reinhardtii

<400> SEQUENCE: 11

Met Cys His Ala Cys Leu Glu Leu Ser Val Arg Gly Lys Val Arg Ala
1               5                   10                  15

Leu Lys Thr His Lys Leu Leu Leu Pro Gly Asp Asn Ile Ala Val Ala
                20                  25                  30

Leu Ser Gly Gly Ser Cys Ser Leu Thr Leu Leu Ser Asn Val Leu Pro
            35                  40                  45

Met Arg Lys Asp Ala Ser Thr Pro Arg Lys Glu Arg Gly Lys Ile Glu
        50                  55                  60

Phe Gly Leu Thr Val Ile His Val Asn Glu Ala Thr Ala His Gly Ala
65                  70                  75                  80

Ala Ala Ala Glu Ala Glu Ala His Ser Arg Asp Val Ala Ala Ala
                85                  90                  95

Arg Gln Cys Ala Ala Val Ala Ala Ala Met Thr Thr Ala Glu Ser Gly
            100                 105                 110

Gly Ser Ser Thr Ala Ala Ser Thr Ser Thr Ser Met Gly Asn Ala Ser
        115                 120                 125

Pro Gly Leu Asp Val Trp Val Val Pro Leu Arg Asp Val Phe Leu Leu
    130                 135                 140

Gly Asp Ala Glu Ala Leu Arg Arg Glu Ala Val Arg Ser Trp Arg Gln
145                 150                 155                 160

Gln Gln Gln Gln Gln Gln Gln Pro Ala Ala Asp Gly Thr Pro Val Trp
                165                 170                 175

Gly Gly Glu Ala Gly Gly Asp Ser Asp Tyr Val Gly Glu Ala Ala Ala
            180                 185                 190

Thr Ala Ser Gly Ala Ala Glu Arg Glu Ala Arg Leu Gln Gln Leu Leu
        195                 200                 205
```

Gln Ala Val Gln Asp Pro Thr Gly Arg Glu Asp Leu Ile Arg His Leu
            210                 215                 220

Arg Arg Arg Leu Leu Ala Ala Ala Gly Ala Val Ala Gly Ala Thr Lys
225                 230                 235                 240

Leu Leu Cys Gly Asp Ser Ala Thr Ala Leu Ala Ala Arg Val Ile Ala
                245                 250                 255

Glu Thr Ala Lys Gly Arg Gly Phe Ala Leu Pro Ser Asp Ile Gln Leu
            260                 265                 270

Val Asp Ala Arg Gly Thr Gly Ala Gly Glu Pro Thr Phe Leu Tyr Pro
        275                 280                 285

Met Arg Glu Val Thr Val Lys Glu Ala Val Phe Val Cys Arg Leu Arg
    290                 295                 300

Gly Leu His Leu Ala Glu Leu Pro Ala Pro Leu Leu Leu Ala Arg Leu
305                 310                 315                 320

Ser Ser Ala Ser Thr Gly Leu His Ser His Pro Arg Arg Ser Ile
                325                 330                 335

Asn Ser Leu Ala Ser Ala Phe Val Asp Ser Leu Gln Ala Asn Leu Pro
            340                 345                 350

Ser Thr Ile Phe Thr Val Leu Arg Thr Ala Ser Ala Leu Arg Pro Phe
        355                 360                 365

Pro Phe Asn Ser Pro Asp Ala Met Pro Ser Thr Phe Pro Ala Thr Pro
    370                 375                 380

Asn Asn Glu Leu Lys Ala Leu His Gly Arg Ser Thr Glu Gly Ala Ser
385                 390                 395                 400

Gly Ala Asn Gly Asp Gly Val Ala Val Gly Cys Arg Pro Ala Ala Val
                405                 410                 415

Pro Cys Cys Val Leu Cys Arg Ala Pro Leu Ser Ala Arg Glu Leu Arg
            420                 425                 430

Ala Ile His Ala Ala Ala Ser Ala Ala Asp Ala Gly Lys Gln Glu
        435                 440                 445

Gly Ala Gly Ser Val Glu Val Val Gln Ala Glu Gln Glu Gly Asp
    450                 455                 460

Asp Glu Glu Asp Ala Ala Ala Pro Phe Cys Gly Ser Cys Arg Gly Gln
465                 470                 475                 480

Ile Leu Phe Arg Pro Gly His His Glu Ala Arg Gly Arg Glu Glu Ala
                485                 490                 495

Gly Gly Ser Gly Asn Val Asp Gly Pro Ser Leu Val Gln Gly Leu Leu
            500                 505                 510

Pro Glu Ala Leu Ala Ala
        515

<210> SEQ ID NO 12
<211> LENGTH: 424
<212> TYPE: PRT
<213> ORGANISM: Yarrowia lipolytica

<400> SEQUENCE: 12

Met Ser Ala Glu Ser Thr Cys Arg Arg Cys Asp Gly Pro Thr Ala Ile
1               5                   10                  15

Lys Thr Arg Gln Ala Asn Phe Cys Gln Pro Cys Phe Ile Thr Phe Ile
            20                  25                  30

Gln Gln Lys Gln Arg Lys Ala Met Glu Gly Cys Lys Val Leu Phe Ala
        35                  40                  45

Arg Pro Gly Cys Val Leu Pro Pro Ala Ile Asn Ile Leu Val Pro Ile
    50                  55                  60

Ser Phe Gly Gln Ser Ser Leu Ala Leu Leu Asp Met Ala His Ala Gln
65              70                  75                  80

Leu Glu Glu Gln Ala Lys Thr Tyr Glu Asn Ala Ala Gly Phe Thr Leu
            85                  90                  95

Asn Ala Val Phe Ile Asp Cys Ser Glu Ala Asp Pro Leu Glu Lys Glu
            100                 105                 110

Pro Asn Gln Ile Ile Ser Glu Leu Glu Lys Arg Phe Ala His Ala Lys
            115                 120                 125

Phe Thr Cys Ile Pro Leu Ser Lys Ala Phe Glu Gly Ala Ser Ser Val
            130                 135                 140

Thr Leu Lys His Asn Arg Asp Tyr Thr Ser Phe Val Ser Gly Ile Ser
145                 150                 155                 160

Glu Glu Pro Thr Ser Val Gln Gln Leu Leu Ser Cys Ile Gly Thr Lys
                165                 170                 175

Ser Ala Arg Glu Asp Ile Ile Ser Val Leu Gln Arg His Leu Ile Ile
            180                 185                 190

Glu Glu Ala Lys Lys Gln Asn Glu Ser Leu Pro Thr Thr Val Ala Trp
            195                 200                 205

Gly His Asn Ala Thr Arg Leu Ala Glu Leu Thr Leu Ser Leu Thr Ile
210                 215                 220

Lys Gly Arg Gly Asn Arg Ile His Ala Gln Val Leu Glu His Lys Asn
225                 230                 235                 240

Pro Lys Asp Ser Ile Ser Gly Leu Pro Glu Ile His Pro Leu Asn Asp
                245                 250                 255

Val Leu Ser Tyr Glu Ile Pro Phe Tyr Asn Ser Phe Arg Asn Val Ser
            260                 265                 270

Asp Leu Ala Val Asp Thr Val Ser Lys Pro Ser Gln Val Thr Lys Asn
            275                 280                 285

Leu Ser Ile Asp Gln Leu Met His Gln Tyr Phe Glu Asn Ile Gln Thr
290                 295                 300

Asn Phe Pro Ser Ile Ala Ser Thr Val Val Arg Thr Ala Ala Lys Leu
305                 310                 315                 320

Asp Asp Pro Asn Ala Ala Lys Gln Gly Leu Thr Pro Cys Leu Ile Cys
                325                 330                 335

Ala Ser Pro Val Asp Pro Asn Gln Ser Leu Ala Trp Leu Thr Asn Ile
            340                 345                 350

Thr Val Asn Glu Pro Ala Ala Pro Glu Thr Glu Glu Glu Glu Glu Leu
            355                 360                 365

Ser Lys Lys Ala His Met Glu Lys Ser Gln Glu Lys Thr Gly Asp Ala
            370                 375                 380

Asp Arg His Leu Pro Val Pro Asn Leu Cys Tyr Gly Cys Ile Ile Thr
385                 390                 395                 400

Ile Arg Asp Thr Asp Ser Phe Thr Phe Pro Lys Arg Ala Ser Lys Gln
                405                 410                 415

Asp Ile Leu Asp Glu Phe Thr Leu
            420

<210> SEQ ID NO 13
<211> LENGTH: 458
<212> TYPE: PRT
<213> ORGANISM: Arabidopsis thaliana

<400> SEQUENCE: 13

Met Ala Cys Asn Ser Ser Gly Cys Glu Ser Gly Cys Tyr Asp Arg Glu

```
  1               5                  10                 15
Lys Asp Asn Gly Ser Lys Ile Val Asp Asp Ala Val Ser Gly Gly
                20                 25                 30

Asn His Glu Ser Val Cys Val Lys Cys Lys Cys Asn Ala Pro Met Thr
                35                 40                 45

Phe Gly Asp Gly Gly Phe Asp Gly Arg Phe Cys Ala Asp Cys Phe
     50                 55                 60

Arg Asn Asn Val Phe Gly Lys Phe Arg Leu Ala Val Thr Ser His Ala
 65                 70                 75                 80

Met Ile Thr Pro Ser Asp Asn Val Leu Val Ala Phe Ser Gly Gly Ser
                 85                 90                 95

Ser Ser Arg Val Ser Leu Gln Phe Val His Glu Leu Gln Ile Lys Ala
                100                105                110

Leu Lys Asn Tyr Glu Ala Ser Arg Asp Arg Ser Leu Pro Val Phe Gly
                115                120                125

Val Gly Val Ala Phe Val Asp Glu Thr Ala Ala Phe Pro Ala Leu Ser
                130                135                140

Thr Glu Met Ile Asp Ala Ile Glu Trp Val Arg Tyr Thr Val Ser Cys
145                150                155                160

Leu Ser Pro Pro Ala Lys Asp Leu His Val Val Pro Val Glu Ser Ile
                165                170                175

Phe Gly Ser Asp Ser Leu Asp Ala Arg Asp Arg Leu Leu Lys Leu Leu
                180                185                190

Asp Ser Val Pro Asp Asp Thr Gly Lys Glu Asp Leu Leu Leu His Leu
                195                200                205

Lys Met Leu Ser Leu Gln Lys Val Ala Ala Glu Asn Gly Tyr Asn Arg
210                215                220

Leu Val Leu Gly Ser Cys Thr Ser Arg Ile Ala Ser His Val Leu Thr
225                230                235                240

Ala Thr Val Lys Gly Arg Gly Tyr Ser Leu Ser Ala Asp Ile Gln His
                245                250                255

Val Asp Ala Arg Trp Lys Val Pro Ile Val Leu Pro Leu Arg Asp Cys
                260                265                270

Val Arg Leu Glu Ile Thr Arg Leu Cys Leu Leu Asp Gly Leu Lys Thr
                275                280                285

Val Glu Leu Ala Cys Arg Ser Gln Cys Gly Ile Asn Asp Leu Val Ser
                290                295                300

Ser Phe Val Ala Leu Leu Gln Glu Gly Asn Pro Ser Arg Glu Cys Thr
305                310                315                320

Ile Val Arg Thr Ala Ala Lys Leu Thr Pro Phe Tyr Phe Asn Lys Ile
                325                330                335

Pro Glu Thr Asp Asp Ser Asn Val Pro Met Ala Thr Gln Arg Arg Leu
                340                345                350

Lys Arg Phe Asn Leu Lys Tyr Asp Gly Ser Met Thr Thr Glu Ala Phe
                355                360                365

Cys Pro Ile Cys Asn Gly Pro Leu Asn Arg Ser Asp Ser Ser Glu Leu
                370                375                380

Asp Thr Phe Glu Glu Gly Gln Glu Ser Asp Val Leu Tyr Ala Ala Cys
385                390                395                400

Cys Ser Ser Cys Arg Phe Gln Ile Leu Pro Gln Asp Gly Ser Ser Leu
                405                410                415

Glu Gln Phe Ser Ser Phe Leu Pro Asp His Met Ile Ser Gln Val Lys
                420                425                430
```

His Gln Lys Val Asp Ser Gln Ala Tyr Leu Arg Glu Lys Ile Lys Asp
    435                 440                 445

Cys Leu Leu Asp Asp Glu Glu Val Val
    450                 455

<210> SEQ ID NO 14
<211> LENGTH: 497
<212> TYPE: PRT
<213> ORGANISM: Neurospora crassa

<400> SEQUENCE: 14

Met Ala Ser Thr Ser Pro Pro Ser Thr Ser Pro Ala Ala Met Ser
1               5                   10                  15

Ser Thr Thr Thr Thr Ala Thr Thr Ala Thr Ala Lys Pro Cys Ile Lys
                20                  25                  30

Cys Arg Ser Asn Pro Gly Thr Leu Asp Ser Arg Gly Gln Leu Val Cys
            35                  40                  45

His Ile Cys Phe Gln Lys Phe Ile Ser Gln Lys Cys Ile Lys Gln Ile
    50                  55                  60

Gly Leu Leu Asn Lys Asp Val Arg Ser Ser Ser Gln Ser Leu Ser
65                  70                  75                  80

Ala Tyr His Leu Ser Gln Lys Asn Ser Gly Pro Pro Gln Ala Ser Ser
                85                  90                  95

Arg Arg Tyr Leu Leu Gly Leu Ser Leu Gly Ala Ser Ser Ala Ala Leu
            100                 105                 110

Leu Glu Leu Leu Asn Glu Asn Val Glu Phe Gln Leu Ser Lys Gly Arg
        115                 120                 125

Asn Ala Pro Phe Glu Leu Glu Val Val His Val Ser Cys Ala Ala Gly
    130                 135                 140

Ala Gly Ala Asp Gly Gly Gly Gly Gly Gly Leu Glu Asp Asp Gly
145                 150                 155                 160

Lys Gly Arg Thr Thr Thr Glu Arg Glu Lys Val Glu Glu Val Val Leu
                165                 170                 175

Lys Arg Leu Gly Gly Arg Tyr Pro Arg Phe Glu Phe Arg Val Val Tyr
            180                 185                 190

Leu Glu Glu Val Val Gly Leu Glu Thr Val Asp Trp Glu Gly Leu Gly
        195                 200                 205

Leu Glu Asp Phe Ala Gly Ser Ser Thr Ser Thr Thr Thr Lys Ala
    210                 215                 220

Glu Lys Leu Gln Gln Leu Phe Asp Asn Leu Pro Ser Thr Thr Ser Arg
225                 230                 235                 240

Thr Asp Leu Leu Arg Leu Phe Thr Arg His Leu Leu Ile Ala Glu Ala
                245                 250                 255

Arg Lys Ser His Cys His Ala Leu Leu Leu Gly Ser Ser Thr Thr Ala
            260                 265                 270

Leu Ala Glu Leu Thr Leu Ser Glu Thr Ala Lys Gly Arg Gly Phe Ser
        275                 280                 285

Leu Pro Trp Gln Ile Asn Asp Gly Val Leu Gly Val Pro Ser Phe Ser
    290                 295                 300

Pro Ser Ser Ser Pro Ser Pro Ser Ser Pro Ala Asp Ala Gly Lys
305                 310                 315                 320

Lys Thr Lys Met Glu Glu Thr Gly Met Leu Val Tyr His Pro Leu Arg
                325                 330                 335

Asp Ala Leu Arg Lys Glu Leu Val Thr Phe Thr Lys Leu Ala Gly Gln

```
                340                 345                 350
Pro Thr Pro Ile Ala Glu Leu Leu Pro Glu Thr Asp Ser Phe Thr Thr
        355                 360                 365

Thr Ala Ala Val Val Ser His Lys Asp Leu Ser Ile Asp Glu Val Met
        370                 375                 380

Val Arg Tyr Phe Ala Glu Val Glu Glu Asn Tyr Pro Ser Ile Val Ala
385                 390                 395                 400

Asn Val Ala Arg Thr Thr Gly Lys Leu Met Arg Leu Phe Gly Gly Ala
                405                 410                 415

Gly Val Ala Asp Gly Asp Gly Asp Glu Glu Gly Gly Lys Ala Val
                420                 425                 430

Gly Glu Asp Gly Ser Glu Asp Asn Asp Glu Glu Arg Leu Cys Gly Leu
        435                 440                 445

Cys Ser Met Pro Leu Asp Val Leu Gly Asp Glu Arg Trp Lys Gly Glu
        450                 455                 460

Leu Gly Glu Asp Ser Tyr Arg Asp Ala Leu Val Val Asp Lys Gly Ala
465                 470                 475                 480

Lys Arg Met Lys Gln Arg Ile Cys Tyr Gly Cys Glu Arg Ser Ile Arg
                485                 490                 495

Gly

<210> SEQ ID NO 15
<211> LENGTH: 461
<212> TYPE: PRT
<213> ORGANISM: Ashbya gossypii

<400> SEQUENCE: 15

Met Lys Cys Lys Arg Cys Thr Thr Ser Glu Gly Cys Leu Val Ser Arg
1               5                   10                  15

Asn Glu Thr Phe Cys Gly Glu Cys Phe Ser Arg Phe Val Leu Leu Lys
                20                  25                  30

Phe Arg Lys Gln Met Met Met Asp Glu Tyr Cys Gln Gln Val Phe Lys
            35                  40                  45

Val Leu Tyr Ala Asp Lys His Arg Thr Ala Val Glu Ala Asp Glu Gln
50                  55                  60

Asn Lys Arg Ser Val Val Leu Val Pro Leu Ser Leu Gly Ser Ser Ser
65                  70                  75                  80

Leu Ala Met Leu Asp Leu Leu Asn Gln Thr Leu Ser Glu Gln Arg Ala
                85                  90                  95

Ala His Asn Arg Thr Gly Phe Gln Val Lys Val Leu Cys Gly Phe
            100                 105                 110

Ser Ala Asp Met Asp Glu Leu Lys Arg Leu Ala Glu Ser Leu Gln Thr
        115                 120                 125

Glu Arg Leu Ala Met Asn Ser Asp Cys Ile Lys Leu Tyr Leu Leu Asp
        130                 135                 140

Leu Asp Arg Ser Phe Ser Thr Cys Glu Ile His Lys Leu Leu Leu Ala
145                 150                 155                 160

Asn Asp Asn His Gly Ser Arg Lys Ile Ala Thr Arg Glu Asn Ala Thr
                165                 170                 175

Leu Ser Ser Ile Leu Asp Gln Phe Ser Arg Arg Ser Arg Asp Asp
            180                 185                 190

Met Leu Trp Phe Ala Arg Gln His Leu Ile Lys Lys Phe Ala Ser Gln
        195                 200                 205

His Gln Val Lys Val Ile Met Trp Gly His Ser Val Thr Arg Leu Ala
```

```
                   210                 215                 220
Asp Glu Val Met Ser Leu Val Ile Lys Gly Arg Gly Ala Gln Ile Ala
225                 230                 235                 240

Ala Thr Leu Asp Ser Thr Gly Met Asp Val Glu Tyr Gly Ala Leu Phe
                245                 250                 255

Lys Asn Leu Tyr Pro Leu Arg Asp Val Leu Leu Ser Glu Ile Asp Ala
                    260                 265                 270

Tyr Cys Ser Leu Ser Lys Leu Gln Arg Tyr Ile Tyr Asn Tyr Ser Leu
                275                 280                 285

Gln Gly Ser Leu Phe Ile Lys Ser Gln Asp Glu Ala Ala Gln Ala Asn
                290                 295                 300

Arg Ala Val Pro Met Ala Lys Asn Met Thr Ile Asn Glu Leu Thr Arg
305                 310                 315                 320

Gln Tyr Phe Asp Ala Val Glu Lys Asp Tyr Ser Asn Val Ile Ser Thr
                    325                 330                 335

Ile Val Arg Thr Ala Ser Lys Leu Asp Tyr Pro Ile Ser Asn Gly Thr
                340                 345                 350

Glu Val Ile Tyr Cys Ser Ile Cys Asn Asn Arg Val Tyr Val Asp Pro
                355                 360                 365

Ser Lys Trp Leu Lys Ser Ile Thr Val Asn Asn Cys His Pro Pro Ala
370                 375                 380

Ser Asp Glu Asp Met Ser Met Leu Gln Met Trp Glu Ser Ser Ser Lys
385                 390                 395                 400

Gly Lys Glu Thr Leu Ala Arg Asn Gln Ala Arg Ser Asn Ile Trp Ser
                    405                 410                 415

Thr Ala Ala Glu Ala Pro Leu Cys Tyr Gly Cys Val Val Thr Leu Asn
                420                 425                 430

Glu Thr Lys Asp Arg Glu Leu Asn Trp Pro Ser Arg Glu His Asp Val
                435                 440                 445

Ser Gln Val Leu Ala Glu Phe Thr Leu Thr Asp Glu Glu
                450                 455                 460

<210> SEQ ID NO 16
<211> LENGTH: 493
<212> TYPE: PRT
<213> ORGANISM: Saccharomyces cerevisiae (strain YJM789)

<400> SEQUENCE: 16

Met Glu Cys Gln Arg Cys Ser Ala Ser Ala Arg Asn Pro Ala Thr Val
1               5                   10                  15

Glu Ser Arg Lys Glu Lys Phe Cys Asp Glu Cys Phe Ile Lys Phe Val
                20                  25                  30

Ser Thr Lys Gln Arg Lys Gln Met Met Lys Asp Glu Tyr Phe Arg Asn
                35                  40                  45

Leu Phe Lys Val Ile Tyr Pro Phe Glu Lys Glu Gly Ser Val Ser Lys
                50                  55                  60

Ile Leu Leu Pro Leu Ser Leu Ser Asp Ser Gly Ser Leu Val Met Leu
65                  70                  75                  80

Asp Ile Val His Asp Leu Leu Glu Gln Thr Lys Gln His Asn Asn
                    85                  90                  95

Arg Thr Gly Phe Thr Val Asp Val Leu Thr Val Phe Thr Glu Glu Asn
                    100                 105                 110

Val Ser Val Ile Lys Glu Arg Met Glu Ser Leu Ile Asn Glu Lys Met
                115                 120                 125
```

```
Ser Gln Leu Asn Lys Ile Ser Asn Ile Phe Asn Val His Phe Ile Asp
    130                 135                 140

Val Asn Glu Phe Phe Asn Asn Ala Ser Glu Val Ser Thr Phe Ile Ile
145                 150                 155                 160

Asp Asn Glu Asn Phe Glu Ile Phe Ser Lys Ser Lys Ser Val Asp Asp
                165                 170                 175

Ser Asn Ile Leu Thr Leu Lys Glu Ile Leu Gly Lys Tyr Cys Leu Asn
                180                 185                 190

Ser Ser Ser Arg Ser Asp Leu Ile Ser Ile Ile Lys Thr Gln Leu Ile
            195                 200                 205

Lys His Phe Ala Tyr Glu Asn Gly Tyr Asn Ala Ile Met Trp Gly His
        210                 215                 220

Ser Met Thr Lys Leu Ser Glu Val Ile Ile Ser Leu Val Lys Gly
225                 230                 235                 240

Lys Gly Ser Gln Ile Ala Thr Phe Leu Asp Ser Glu Ser Phe Asp Thr
                245                 250                 255

Leu Asn Asn Lys Pro Cys Lys Tyr Lys Asn Leu Tyr Pro Met Lys Asp
                260                 265                 270

Leu Leu Ser Val Glu Ile Glu Ser Phe Leu Gln Ile Arg Asn Leu Ala
            275                 280                 285

Gln Phe Leu Ile Asn Val Glu Glu Thr Asn Val Lys Pro Asn Cys Leu
        290                 295                 300

Ile Ala Arg Lys Ser Leu Pro Ser Leu Gly Gln Gln Lys Leu Val Lys
305                 310                 315                 320

Asn Met Thr Ile Asn Glu Ile Thr Asn Lys Tyr Phe Gln Asp Ile Gln
                325                 330                 335

Asn Asp Tyr Ser Asn Ile Ile Ser Thr Val Leu Arg Thr Ala Asp Lys
            340                 345                 350

Leu Thr Gln Pro Lys Ser Ser Met Ala Lys Pro Ser Gln Cys Gln Ile
        355                 360                 365

Cys Gln Ser Lys Ile Tyr Thr Asn Pro Ser Asn Trp Leu Asn Arg Ile
    370                 375                 380

Thr Val Thr Ser Pro Tyr Pro Val Glu Thr Thr Glu Glu Lys Tyr Leu
385                 390                 395                 400

Phe Lys Gln Trp Gln Asp Ser Lys Leu Gly Gln Ser His Thr His Tyr
                405                 410                 415

Val Glu Leu Leu Asn Glu Ile Lys Gln Gly Ala Ser Asn Ser Leu Asp
            420                 425                 430

Val Glu Asp Ser Asp Val Lys Leu Cys Tyr Gly Cys Leu Ile Leu Leu
        435                 440                 445

Asn Thr Ser Ile Lys Asp Lys Asn Leu Val Trp Pro Lys Val Asp Thr
    450                 455                 460

Met Asp Ile Thr Ala Asn Ala Thr Asn Lys Asn Lys Glu Leu Ser Gln
465                 470                 475                 480

Ile Leu Asp Gln Phe Glu Ile Asn Ser Asp Gly Glu Glu
                485                 490

<210> SEQ ID NO 17
<211> LENGTH: 349
<212> TYPE: PRT
<213> ORGANISM: Caenorhabditis elegans

<400> SEQUENCE: 17

Met Glu Leu Gly Asn Phe Val Thr Asp Leu Asn Gly Lys Lys Cys Val
1               5                   10                  15
```

```
Lys Cys Asp Lys Asp Ala Lys Phe Thr Gly Val Asp Pro Lys Ala
             20                  25                  30

Trp Tyr Cys Gln Glu Cys Phe Val Gln Met Val Arg Asn Lys Phe Arg
         35                  40                  45

Ser Ser Leu Ser Lys Lys Ile Tyr Lys Asp Ala Asp Ala Arg Asp
 50                  55                  60

Thr Leu Ile Val Phe Asp Gly Thr Leu Ser Gly Thr Phe Leu Leu His
 65                  70                  75                  80

Gln Ile Asn Asp Ala Leu Lys Gln Ile Thr Tyr Lys Arg Leu Met Val
                 85                  90                  95

Lys Pro Thr Val Leu Val Leu Val Ser Leu Thr Glu Asp Thr Glu Ile
                100                 105                 110

Gln Met Val Ile Lys Arg Ile Gln Glu Ile Lys Lys Ser Val Leu Glu
            115                 120                 125

Asn Val Arg Trp Val Val Ala His Leu Ala Cys Ser Met Tyr Asp Glu
130                 135                 140

Asp Phe Lys Leu Lys Glu Asn Glu Cys Asn Gly Val Glu Lys Ile Ser
145                 150                 155                 160

Asp Tyr Asn Gln Leu Ile Ala Ser Cys Ser Val Pro Thr Tyr Arg Lys
                165                 170                 175

Glu Leu Glu Arg Val Leu Lys Glu Lys Cys Leu Gln Lys Ile Ala Cys
            180                 185                 190

Ser Met Gly Ile Leu Lys Cys Met Val Pro Asp His Ala Asp Asp Leu
        195                 200                 205

Gly Arg Leu Ala Ile Asp Gln Leu Cys Leu Gly Arg Gly Gly Ser Ile
210                 215                 220

Ser Thr Leu Val Thr Val Thr Asp Lys Arg Pro Asp Phe Met Leu Ile
225                 230                 235                 240

Arg Pro Leu Cys Asp Ile Ser Lys Lys Glu Leu Ala Val Tyr Asn Tyr
                245                 250                 255

Leu Cys Asp Ile Asp Lys His Cys Ile His Ile Ala Gln Gln Asn Asn
                260                 265                 270

Gln Gln Lys Ser Val Gln Thr Leu Thr Asp Ala Phe Ile Cys Thr Leu
            275                 280                 285

Glu Asn Glu Lys Phe Tyr Ser Thr Ile Asn Thr Val Leu Ser Thr Ala
290                 295                 300

Ala Lys Ile His Asn Thr Ser Ile Gly Lys Asp Asp Ser Lys Cys Ser
305                 310                 315                 320

Phe Cys Asn Val Glu Val Ala Asp Ser Val Cys Ser Thr Cys Ser Ala
                325                 330                 335

Ile Arg Glu Cys Thr Gly Asp Leu Leu Thr Leu Leu Phe
            340                 345

<210> SEQ ID NO 18
<211> LENGTH: 493
<212> TYPE: PRT
<213> ORGANISM: Saccharomyces cerevisiae (strain AWRI1631) (Baker's
      yeast)

<400> SEQUENCE: 18

Met Glu Cys Gln Arg Cys Pro Ala Ser Ala Arg Asn Pro Ala Thr Val
1               5                   10                  15

Glu Ser Arg Lys Glu Lys Phe Cys Asp Glu Cys Phe Ile Lys Phe Val
            20                  25                  30
```

```
Ser Thr Lys Gln Arg Lys Gln Met Met Lys Asp Glu Tyr Phe Arg Asn
         35                  40                  45
Leu Phe Lys Val Ile Tyr Pro Phe Glu Lys Glu Gly Ser Val Ser Lys
 50                  55                  60
Ile Leu Leu Pro Leu Ser Leu Ser Asp Ser Gly Ser Leu Val Met Leu
 65                  70                  75                  80
Asp Ile Val His Asp Leu Leu Leu Glu Gln Thr Lys Gln His Asn Asn
                 85                  90                  95
Arg Thr Gly Phe Thr Val Asp Val Leu Thr Val Phe Thr Glu Glu Asn
                100                 105                 110
Val Ser Val Ile Lys Glu Arg Met Glu Ser Leu Ile Asn Glu Lys Met
                115                 120                 125
Ser Gln Leu Asn Lys Ile Ser Asn Ile Phe Asn Val His Phe Ile Asp
 130                 135                 140
Val Asn Glu Phe Phe Asn Asn Ala Ser Glu Val Ser Thr Phe Ile Ile
 145                 150                 155                 160
Asp Asn Glu Asn Phe Glu Ile Phe Ser Lys Ser Lys Ser Val Asp Asp
                165                 170                 175
Ser Asn Ile Leu Thr Leu Lys Glu Ile Leu Gly Lys Tyr Cys Leu Asn
                180                 185                 190
Asn Ser Ser Arg Ser Asp Leu Ile Ser Ile Ile Lys Thr Gln Leu Ile
     195                 200                 205
Lys His Phe Ala Tyr Glu Asn Gly Tyr Asn Ala Ile Met Trp Gly His
     210                 215                 220
Ser Met Thr Lys Leu Ser Glu Val Ile Ile Ser Leu Val Val Lys Gly
225                 230                 235                 240
Lys Gly Ser Gln Ile Ala Thr Phe Leu Asp Ser Glu Ser Phe Asp Thr
                245                 250                 255
Leu Asn Asn Lys Pro Cys Lys Tyr Lys Asn Leu Tyr Pro Met Lys Asp
                260                 265                 270
Leu Leu Ser Val Glu Ile Glu Ser Phe Leu Gln Ile Arg Asn Leu Ala
                275                 280                 285
Gln Phe Leu Ile Asn Val Glu Glu Thr Asn Val Lys Pro Asn Cys Leu
 290                 295                 300
Ile Ala Arg Lys Ser Leu Pro Ser Leu Gly Gln Gln Lys Leu Val Lys
305                 310                 315                 320
Asn Met Thr Ile Asn Glu Ile Thr Asn Lys Tyr Phe Gln Asp Ile Gln
                325                 330                 335
Asn Asp Tyr Ser Asn Ile Ile Ser Thr Val Ser Arg Thr Ala Asp Lys
                340                 345                 350
Leu Thr Gln Pro Lys Ser Ser Met Ala Lys Pro Ser Gln Cys Gln Ile
                355                 360                 365
Cys Gln Ser Lys Ile Tyr Thr Asn Pro Ser Asn Trp Leu Asn Arg Ile
     370                 375                 380
Thr Val Thr Ser Pro Tyr Pro Val Glu Thr Thr Glu Glu Lys Tyr Leu
385                 390                 395                 400
Phe Lys Gln Trp Gln Asp Ser Lys Leu Gly Gln Ser His Thr His Tyr
                405                 410                 415
Val Glu Leu Leu Asn Glu Ile Lys Gln Gly Ala Ser Asn Ser Leu Asp
                420                 425                 430
Val Glu Asp Gly Asp Val Lys Leu Cys Tyr Gly Cys Leu Ile Leu Leu
                435                 440                 445
Asn Thr Ser Ile Lys Asp Lys Asn Leu Val Trp Pro Lys Val Asp Thr
```

```
            450                 455                 460
Met Asp Ile Thr Ala Asn Ala Thr Asn Asn Lys Glu Leu Ser Gln
465                 470                 475                 480

Ile Leu Asp Gln Phe Glu Ile Asn Ser Asp Gly Glu Glu
                485                 490

<210> SEQ ID NO 19
<211> LENGTH: 493
<212> TYPE: PRT
<213> ORGANISM: Saccharomyces cerevisiae (strain ATCC 204508 / S288c)
      (Baker's yeast)

<400> SEQUENCE: 19

Met Glu Cys Gln Arg Cys Pro Ala Ser Ala Arg Asn Pro Ala Thr Val
1               5                   10                  15

Glu Ser Arg Lys Glu Lys Phe Cys Asp Glu Cys Phe Ile Lys Phe Val
            20                  25                  30

Ser Thr Lys Gln Arg Lys Gln Met Met Lys Asp Glu Tyr Phe Arg Asn
        35                  40                  45

Leu Phe Lys Val Ile Tyr Pro Phe Glu Lys Glu Gly Ser Val Ser Lys
    50                  55                  60

Ile Leu Leu Pro Leu Ser His Ser Asp Ser Gly Ser Leu Val Met Leu
65                  70                  75                  80

Asp Ile Val His Asp Leu Leu Leu Glu Gln Thr Lys Gln His Asn Asn
                85                  90                  95

Arg Thr Gly Phe Thr Val Asp Val Leu Thr Val Phe Thr Glu Glu Asn
            100                 105                 110

Val Ser Val Ile Lys Glu Arg Met Glu Ser Leu Ile Asn Glu Lys Met
        115                 120                 125

Ser Gln Leu Asn Lys Ile Ser Asn Ile Phe Asn Val His Phe Ile Asp
    130                 135                 140

Val Asn Glu Phe Phe Asn Asn Ala Ser Glu Val Ser Thr Phe Ile Ile
145                 150                 155                 160

Asp Asn Glu Asn Phe Glu Ile Phe Ser Lys Ser Lys Ser Val Asp Asp
                165                 170                 175

Ser Asn Ile Leu Thr Leu Lys Glu Ile Leu Gly Lys Tyr Cys Leu Asn
            180                 185                 190

Asn Ser Ser Arg Ser Asp Leu Ile Ser Ile Lys Thr Gln Leu Ile
        195                 200                 205

Lys His Phe Ala Tyr Glu Asn Gly Tyr Asn Ala Ile Met Trp Gly His
    210                 215                 220

Ser Met Thr Lys Leu Ser Glu Val Ile Ile Ser Leu Val Val Lys Gly
225                 230                 235                 240

Lys Gly Ser Gln Ile Ala Thr Phe Leu Asp Ser Glu Ser Phe Asp Thr
                245                 250                 255

Leu Asn Asn Lys Pro Cys Lys Tyr Lys Asn Leu Tyr Pro Met Lys Asp
            260                 265                 270

Leu Leu Ser Val Glu Ile Glu Ser Phe Leu Gln Ile Arg Asn Leu Ala
        275                 280                 285

Gln Phe Leu Ile Asn Val Glu Glu Thr Asn Val Lys Pro Asn Cys Leu
    290                 295                 300

Ile Ala Arg Lys Ser Leu Pro Ser Leu Gly Gln Gln Lys Leu Val Lys
305                 310                 315                 320

Asn Met Thr Ile Asn Glu Ile Thr Asn Lys Tyr Phe Gln Asp Ile Gln
                325                 330                 335
```

Asn Asp Tyr Ser Asn Ile Ile Ser Thr Val Leu Arg Thr Ala Asp Lys
                340                 345                 350

Leu Thr Gln Pro Lys Ser Ser Met Ala Lys Pro Ser Gln Cys Gln Ile
            355                 360                 365

Cys Gln Ser Lys Ile Tyr Thr Asn Pro Ser Asn Trp Leu Asn Arg Ile
370                 375                 380

Thr Val Thr Ser Pro Tyr Pro Val Glu Thr Thr Glu Glu Lys Tyr Leu
385                 390                 395                 400

Phe Lys Gln Trp Gln Asp Ser Lys Leu Gly Gln Ser His Thr His Tyr
                405                 410                 415

Val Glu Leu Leu Asn Glu Ile Lys Gln Gly Ala Ser Asn Ser Leu Asp
            420                 425                 430

Val Glu Asp Gly Asp Val Lys Leu Cys Tyr Gly Cys Leu Ile Leu Leu
        435                 440                 445

Asn Thr Ser Ile Lys Asp Lys Asn Leu Val Trp Pro Lys Val Asp Thr
450                 455                 460

Met Asp Ile Thr Ala Asn Ala Thr Asn Lys Asn Lys Glu Leu Ser Gln
465                 470                 475                 480

Ile Leu Asp Gln Phe Glu Ile Asn Ser Asp Gly Glu Glu
                485                 490

<210> SEQ ID NO 20
<211> LENGTH: 493
<212> TYPE: PRT
<213> ORGANISM: Saccharomyces cerevisiae (strain RM11-1a) (Baker's
      yeast)

<400> SEQUENCE: 20

Met Glu Cys Gln Arg Cys Pro Ala Ser Ala Arg Asn Pro Ala Thr Val
1               5                   10                  15

Glu Ser Arg Lys Glu Lys Phe Cys Asp Glu Cys Phe Ile Lys Phe Val
                20                  25                  30

Ser Thr Lys Gln Arg Lys Gln Met Met Lys Asp Glu Tyr Phe Arg Asn
            35                  40                  45

Leu Phe Lys Val Ile Tyr Pro Phe Glu Lys Glu Gly Ser Val Ser Lys
        50                  55                  60

Ile Leu Leu Pro Leu Ser Leu Ser Asp Ser Gly Ser Leu Val Met Leu
65                  70                  75                  80

Asp Ile Val His Asp Leu Leu Leu Glu Gln Thr Lys Gln His Asn Asn
                85                  90                  95

Arg Thr Gly Phe Thr Val Asp Val Leu Thr Val Phe Thr Glu Glu Asn
                100                 105                 110

Val Ser Val Ile Lys Glu Arg Met Glu Ser Leu Ile Asn Glu Lys Met
            115                 120                 125

Ser Gln Leu Asn Lys Ile Ser Asn Ile Phe Asn Val His Phe Ile Asp
        130                 135                 140

Val Asn Glu Phe Phe Asn Asn Ala Ser Glu Val Ser Thr Phe Ile Ile
145                 150                 155                 160

Asp Asn Glu Asn Phe Glu Ile Phe Ser Lys Ser Lys Ser Val Asp Asp
                165                 170                 175

Ser Asn Ile Leu Thr Leu Lys Glu Ile Leu Gly Lys Tyr Cys Leu Asn
            180                 185                 190

Asn Ser Ser Arg Ser Asp Leu Ile Ser Ile Ile Lys Thr Gln Leu Ile
        195                 200                 205

-continued

```
Lys His Phe Ala Tyr Glu Asn Gly Tyr Asn Ala Ile Met Trp Gly His
    210                 215                 220
Ser Met Thr Lys Leu Ser Glu Val Ile Ile Ser Leu Val Val Lys Gly
225                 230                 235                 240
Lys Gly Ser Gln Ile Ala Thr Phe Leu Asp Ser Glu Ser Phe Asp Thr
                245                 250                 255
Leu Asn Asn Lys Pro Cys Lys Tyr Lys Asn Leu Tyr Pro Met Lys Asp
                260                 265                 270
Leu Leu Ser Val Glu Ile Glu Ser Phe Leu Gln Ile Arg Asn Leu Ala
            275                 280                 285
Gln Phe Leu Ile Asn Val Glu Glu Thr Asn Val Lys Pro Asn Cys Leu
        290                 295                 300
Ile Ala Arg Lys Ser Leu Pro Ser Leu Gly Gln Gln Lys Leu Val Lys
305                 310                 315                 320
Asn Met Thr Ile Asn Glu Ile Thr Asn Lys Tyr Phe Gln Asp Ile Gln
                325                 330                 335
Asn Asp Tyr Ser Asn Ile Ile Ser Thr Val Leu Arg Thr Ala Asp Lys
            340                 345                 350
Leu Thr Gln Pro Lys Ser Ser Met Ala Lys Pro Ser Gln Cys Gln Ile
        355                 360                 365
Cys Gln Ser Lys Ile Tyr Thr Asn Pro Ser Asn Trp Leu Asn Arg Ile
370                 375                 380
Thr Val Thr Ser Pro Tyr Pro Val Glu Thr Thr Glu Glu Lys Tyr Leu
385                 390                 395                 400
Phe Lys Gln Trp Gln Asp Ser Lys Leu Gly Gln Ser His Thr His Tyr
                405                 410                 415
Val Glu Leu Leu Asn Glu Ile Lys Gln Gly Ala Ser Asn Ser Leu Asp
            420                 425                 430
Val Glu Asp Gly Asp Val Lys Leu Cys Tyr Gly Cys Leu Ile Leu Leu
        435                 440                 445
Asn Thr Ser Ile Lys Asp Lys Asn Leu Val Trp Pro Lys Val Asp Thr
450                 455                 460
Met Asp Ile Thr Ala Asn Ala Thr Asn Asn Lys Glu Leu Ser Gln
465                 470                 475                 480
Ile Leu Asp Gln Phe Glu Ile Asn Ser Asp Gly Glu Glu
                485                 490
```

<210> SEQ ID NO 21
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (8)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 21

```
Xaa Xaa Xaa Xaa Xaa Xaa Ser Xaa Xaa Xaa Xaa Ser Xaa Xaa Xaa
1               5                   10                  15

Leu Xaa Xaa Xaa
            20

<210> SEQ ID NO 22
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(7)
<223> OTHER INFORMATION: Xaa can be any naturally occurring amino acid

<400> SEQUENCE: 22

Xaa Xaa Xaa Xaa Xaa Xaa Xaa
1               5

<210> SEQ ID NO 23
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(21)
<223> OTHER INFORMATION: Xaa can be any naturally occurring amino acid

<400> SEQUENCE: 23

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 24
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid

<400> SEQUENCE: 24

Xaa Xaa Xaa Gly Xaa Xaa Xaa Xaa Xaa Xaa Xaa Xaa Xaa Xaa Xaa
1               5                   10                  15

Xaa Xaa Xaa Xaa Gly Xaa Gly Xaa Xaa Xaa
            20                  25

<210> SEQ ID NO 25
<211> LENGTH: 13
```

```
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(13)
<223> OTHER INFORMATION: Xaa can be any naturally occurring amino acid

<400> SEQUENCE: 25

Pro Xaa Xaa Xaa Xaa Xaa Xaa Xaa Xaa Xaa Xaa Xaa Xaa
1               5                   10

<210> SEQ ID NO 26
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(30)
<223> OTHER INFORMATION: Xaa can be any naturally occurring amino acid

<400> SEQUENCE: 26

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Lys Leu
            20                  25                  30

<210> SEQ ID NO 27
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 27

Cys Xaa Xaa Cys Xaa Xaa Xaa Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 28

Xaa Cys Xaa Xaa Cys Xaa Xaa Xaa Xaa
1               5
```

<210> SEQ ID NO 29

<400> SEQUENCE: 29

000

<210> SEQ ID NO 30
<211> LENGTH: 2233
<212> TYPE: PRT
<213> ORGANISM: Rhodosporidium toruloides

<400> SEQUENCE: 30

```
Met Pro Phe Ser Gly Glu Ala Lys Ala Val Asn Gly Ser His Ser Val
1               5                   10                  15

Asp Glu Ala Pro Lys Asn Pro Lys Tyr Asp His Gly Arg Val Val Lys
            20                  25                  30

Tyr Leu Gly Gly Asn Ser Leu Glu Ser Ala Pro Pro Ser Lys Val Ala
        35                  40                  45

Asp Trp Val Arg Glu Arg Gly Gly His Thr Val Ile Thr Lys Ile Leu
    50                  55                  60

Ile Ala Asn Asn Gly Ile Ala Ala Val Lys Glu Ile Arg Ser Val Arg
65                  70                  75                  80

Lys Trp Ala Tyr Glu Thr Phe Gly Ser Glu Arg Ala Ile Glu Phe Thr
                85                  90                  95

Val Met Ala Thr Pro Glu Asp Leu Lys Val Asn Ala Asp Tyr Ile Arg
            100                 105                 110

Met Ala Asp Gln Tyr Val Glu Val Pro Gly Gly Thr Asn Asn Asn Asn
        115                 120                 125

Tyr Ala Asn Val Asp Val Ile Val Asp Val Ala Glu Arg Ala Gly Val
    130                 135                 140

His Ala Val Trp Ala Gly Trp Gly His Ala Ser Glu Asn Pro Arg Leu
145                 150                 155                 160

Pro Glu Ser Leu Ala Ala Ser Lys His Lys Ile Val Phe Ile Gly Pro
                165                 170                 175

Pro Gly Ser Ala Met Arg Ser Leu Gly Asp Lys Ile Ser Ser Thr Ile
            180                 185                 190

Val Ala Gln His Ala Gln Val Pro Cys Met Asp Trp Ser Gly Gln Gly
        195                 200                 205

Val Asp Gln Val Thr Gln Ser Pro Glu Gly Tyr Val Thr Val Ala Asp
    210                 215                 220

Asp Val Tyr Gln Gln Ala Cys Val His Asp Ala Asp Glu Gly Leu Ala
225                 230                 235                 240

Arg Ala Ser Arg Ile Gly Tyr Pro Val Met Ile Lys Ala Ser Glu Gly
                245                 250                 255

Gly Gly Gly Lys Gly Ile Arg Lys Val Glu Lys Glu Gln Asp Phe Lys
            260                 265                 270

Gln Ala Phe Gln Ala Val Leu Thr Glu Val Pro Gly Ser Pro Val Phe
        275                 280                 285

Ile Met Lys Leu Ala Gly Ala Ala Arg His Leu Glu Val Gln Val Leu
    290                 295                 300

Ala Asp Gln Tyr Gly Asn Ala Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335
```

```
Ala Lys Pro Asp Thr Phe Glu Gln Met Glu Lys Ser Ala Val Arg Leu
            340                 345                 350
Ala Lys Leu Val Gly Tyr Val Ser Ala Gly Thr Val Glu Phe Leu Tyr
        355                 360                 365
Ser Ala Ala Asp Asp Lys Phe Ala Phe Leu Glu Leu Asn Pro Arg Leu
    370                 375                 380
Gln Val Glu His Pro Thr Thr Glu Met Val Ser Gly Val Asn Leu Pro
385                 390                 395                 400
Ala Ala Gln Leu Gln Val Ala Met Gly Val Pro Leu His Arg Ile Arg
            405                 410                 415
Asp Ile Arg Thr Leu Tyr Gly Lys Ala Pro Asn Gly Ser Ser Glu Ile
            420                 425                 430
Asp Phe Asp Phe Glu Asn Pro Glu Ser Ala Lys Thr Gln Arg Lys Pro
        435                 440                 445
Ser Pro Lys Gly His Val Val Ala Val Arg Ile Thr Ala Glu Asn Pro
    450                 455                 460
Asp Ala Gly Phe Lys Pro Ser Met Gly Thr Leu Gln Glu Leu Asn Phe
465                 470                 475                 480
Arg Ser Ser Thr Asn Val Trp Gly Tyr Phe Ser Val Gly Ser Ala Gly
            485                 490                 495
Gly Leu His Glu Phe Ala Asp Ser Gln Phe Gly His Ile Phe Ala Tyr
        500                 505                 510
Gly Ser Asp Arg Ser Glu Ser Arg Lys Asn Met Val Val Ala Leu Lys
        515                 520                 525
Glu Leu Ser Ile Arg Gly Asp Phe Arg Thr Thr Val Glu Tyr Leu Ile
    530                 535                 540
Lys Leu Leu Glu Thr Asp Ala Phe Glu Gln Asn Thr Ile Thr Thr Ala
545                 550                 555                 560
Trp Leu Asp Ser Leu Ile Ser Ala Arg Leu Thr Ala Glu Arg Pro Asp
            565                 570                 575
Thr Thr Leu Ala Ile Ile Cys Gly Ala Val Thr Lys Ala His Leu Ala
        580                 585                 590
Ser Glu Ala Asn Ile Ala Glu Tyr Lys Arg Ile Leu Glu Lys Gly Gln
    595                 600                 605
Ser Pro Ala Lys Glu Leu Leu Ala Thr Val Val Pro Leu Glu Phe Val
610                 615                 620
Leu Glu Asp Val Lys Tyr Arg Ala Thr Ala Ser Arg Ser Ser Pro Ser
625                 630                 635                 640
Ser Trp Ser Ile Tyr Val Asn Gly Ser Asn Val Ser Val Gly Ile Arg
            645                 650                 655
Pro Leu Ala Asp Gly Gly Leu Leu Ile Leu Asp Gly Arg Ser Tyr
        660                 665                 670
Thr Cys Tyr Ala Lys Glu Glu Val Gly Ala Leu Arg Leu Ser Ile Asp
        675                 680                 685
Ser Arg Thr Val Leu Ile Ala Gln Glu Asn Asp Pro Thr Gln Leu Arg
    690                 695                 700
Ser Pro Ser Pro Gly Lys Leu Val Arg Tyr Phe Ile Glu Ser Gly Glu
705                 710                 715                 720
His Ile Ser Lys Gly Glu Ala Tyr Ala Glu Ile Glu Val Met Lys Met
            725                 730                 735
Ile Met Pro Leu Ile Ala Ala Glu Asp Gly Ile Ala Gln Phe Ile Lys
            740                 745                 750
Gln Pro Gly Ala Thr Leu Glu Ala Gly Asp Ile Leu Gly Ile Leu Ser
```

-continued

```
            755                 760                 765
Leu Asp Asp Pro Ser Arg Val His His Ala Lys Pro Phe Asp Gly Gln
    770                 775                 780
Leu Pro Ala Leu Gly Leu Pro Ser Ile Ile Gly Asn Lys Pro His Gln
785                 790                 795                 800
Arg Phe Ala Tyr Leu Lys Asp Val Leu Ser Asn Ile Leu Met Gly Tyr
                805                 810                 815
Asp Asn Gln Ala Val Met Gln Ser Ser Ile Lys Glu Leu Ile Ser Val
            820                 825                 830
Leu Arg Asn Pro Glu Leu Pro Tyr Gly Glu Ala Asn Ala Val Leu Ser
        835                 840                 845
Thr Leu Ser Gly Arg Ile Pro Ala Lys Leu Glu Gln Thr Leu Arg Gln
    850                 855                 860
Tyr Ile Asp Gln Ala His Glu Ser Gly Ala Glu Phe Pro Ser Ala Lys
865                 870                 875                 880
Cys Arg Lys Ala Ile Asp Thr Thr Leu Glu Gln Leu Arg Pro Ala Glu
                885                 890                 895
Ala Gln Thr Val Arg Asn Phe Leu Val Ala Phe Asp Asp Ile Val Tyr
            900                 905                 910
Arg Tyr Arg Ser Gly Leu Lys His His Glu Trp Ser Thr Leu Ala Gly
        915                 920                 925
Ile Phe Ala Ala Tyr Ala Glu Thr Glu Lys Pro Phe Ser Gly Lys Asp
    930                 935                 940
Gly Asp Val Val Leu Glu Leu Arg Asp Ala His Arg Asp Ser Leu Asp
945                 950                 955                 960
Ser Val Val Lys Ile Val Leu Ser His Tyr Lys Ala Ala Ser Lys Asn
                965                 970                 975
Ser Leu Val Leu Ala Leu Leu Asp Ile Val Lys Asp Ser Asp Ser Val
            980                 985                 990
Pro Leu Ile Glu Gln Val Val Ser Pro Ala Leu Lys Asp Leu Ala Asp
        995                 1000                1005
Leu Asp Ser Lys Ala Thr Thr Lys Val Ala Leu Lys Ala Arg Glu
    1010                1015                1020
Val Leu Ile His Ile Gln Leu Pro Ser Leu Asp Glu Arg Leu Gly
    1025                1030                1035
Gln Leu Glu Gln Ile Leu Lys Ala Ser Val Thr Pro Thr Val Tyr
    1040                1045                1050
Gly Glu Pro Gly His Asp Arg Thr Pro Arg Gly Glu Val Leu Lys
    1055                1060                1065
Asp Val Ile Asp Ser Arg Phe Thr Val Phe Asp Val Leu Pro Ser
    1070                1075                1080
Phe Phe Gln His Gln Asp His Trp Val Ser Leu Ala Ala Leu Asp
    1085                1090                1095
Thr Tyr Val Arg Arg Ala Tyr Arg Ser Tyr Asn Leu Leu Asn Ile
    1100                1105                1110
Glu His Ile Glu Ala Asp Ala Ala Glu Asp Glu Pro Ala Thr Val
    1115                1120                1125
Ala Trp Ser Phe Arg Met Arg Lys Ala Ala Ser Glu Ser Glu Pro
    1130                1135                1140
Pro Thr Pro Thr Thr Gly Leu Thr Ser Gln Arg Thr Ala Ser Tyr
    1145                1150                1155
Ser Asp Leu Thr Phe Leu Leu Asn Asn Ala Gln Ser Glu Pro Ile
    1160                1165                1170
```

```
Arg Tyr Gly Ala Met Phe Ser Val Arg Ser Leu Asp Arg Phe Arg
1175                1180                1185

Gln Glu Leu Gly Thr Val Leu Arg His Phe Pro Asp Ser Asn Lys
1190                1195                1200

Gly Lys Leu Gln Gln Gln Pro Ala Ala Ser Ser Ser Gln Glu Gln
1205                1210                1215

Trp Asn Val Ile Asn Val Ala Leu Thr Val Pro Ala Ser Ala Gln
1220                1225                1230

Val Asp Glu Asp Ala Leu Arg Ala Asp Phe Ala Ala His Val Asn
1235                1240                1245

Ala Met Ser Ala Glu Ile Asp Ala Arg Gly Met Arg Arg Leu Thr
1250                1255                1260

Leu Leu Ile Cys Arg Glu Gly Gln Tyr Pro Ser Tyr Tyr Thr Val
1265                1270                1275

Arg Lys Gln Asp Gly Thr Trp Lys Glu Leu Glu Thr Ile Arg Asp
1280                1285                1290

Ile Glu Pro Ala Leu Ala Phe Gln Leu Glu Leu Gly Arg Leu Ser
1295                1300                1305

Asn Phe His Leu Glu Pro Cys Pro Val Glu Asn Arg Gln Val His
1310                1315                1320

Val Tyr Tyr Ala Thr Ala Lys Gly Asn Ser Ser Asp Cys Arg Phe
1325                1330                1335

Phe Val Arg Ala Leu Val Arg Pro Gly Arg Leu Arg Gly Asn Met
1340                1345                1350

Lys Thr Ala Asp Tyr Leu Val Ser Glu Ala Asp Arg Leu Val Thr
1355                1360                1365

Asp Val Leu Asp Ser Leu Glu Val Ala Ser Ser Gln Arg Arg Ala
1370                1375                1380

Ala Asp Gly Asn His Ile Ser Leu Asn Phe Leu Tyr Ser Leu Arg
1385                1390                1395

Leu Asp Phe Asp Glu Val Gln Ala Ala Leu Ala Gly Phe Ile Asp
1400                1405                1410

Arg His Gly Lys Arg Phe Trp Arg Leu Arg Val Thr Gly Ala Glu
1415                1420                1425

Ile Arg Ile Val Leu Glu Asp Ala Gln Gly Asn Ile Gln Pro Ile
1430                1435                1440

Arg Ala Ile Ile Glu Asn Val Ser Gly Phe Val Val Lys Tyr Glu
1445                1450                1455

Ala Tyr Arg Glu Val Thr Thr Asp Lys Gly Gln Val Ile Leu Lys
1460                1465                1470

Ser Ile Gly Pro Gln Gly Ala Leu His Leu Gln Pro Val Asn Phe
1475                1480                1485

Pro Tyr Pro Thr Lys Glu Trp Leu Gln Pro Lys Arg Tyr Lys Ala
1490                1495                1500

His Val Val Gly Thr Thr Tyr Val Tyr Asp Phe Pro Asp Leu Phe
1505                1510                1515

Arg Gln Ala Ile Arg Lys Gln Trp Lys Ala Ala Gly Lys Thr Ala
1520                1525                1530

Pro Ala Glu Leu Leu Val Ala Lys Glu Leu Val Leu Asp Glu Phe
1535                1540                1545

Gly Lys Pro Gln Glu Val Ala Arg Pro Pro Gly Thr Asn Asn Ile
1550                1555                1560
```

```
Gly Met Val Gly Trp Ile Tyr Thr Ile Phe Thr Pro Glu Tyr Pro
    1565                1570                1575

Thr Gly Arg Arg Val Val Ile Ala Asn Asp Ile Thr Phe Lys
    1580                1585                1590

Ile Gly Ser Phe Gly Pro Glu Glu Asp Arg Tyr Phe Phe Ala Val
    1595                1600                1605

Thr Gln Leu Ala Arg Gln Leu Gly Leu Pro Arg Val Tyr Leu Ser
    1610                1615                1620

Ala Asn Ser Gly Ala Arg Leu Gly Ile Ala Glu Glu Leu Val Asp
    1625                1630                1635

Leu Phe Ser Val Ala Trp Val Asp Ser Ser Arg Pro Glu Lys Gly
    1640                1645                1650

Phe Lys Tyr Leu Tyr Leu Thr Ala Glu Lys Leu Gly Glu Leu Lys
    1655                1660                1665

Asn Lys Gly Glu Lys Ser Val Ile Thr Lys Arg Ile Glu Asp Glu
    1670                1675                1680

Gly Glu Thr Arg Tyr Gln Ile Thr Asp Ile Ile Gly Leu Gln Glu
    1685                1690                1695

Gly Leu Gly Val Glu Ser Leu Lys Gly Ser Gly Leu Ile Ala Gly
    1700                1705                1710

Glu Thr Ser Arg Ala Tyr Asp Asp Ile Phe Thr Ile Thr Leu Val
    1715                1720                1725

Thr Ala Arg Ser Val Gly Ile Gly Ala Tyr Leu Val Arg Leu Gly
    1730                1735                1740

Gln Arg Ala Val Gln Val Glu Gly Gln Pro Ile Ile Leu Thr Gly
    1745                1750                1755

Ala Gly Ala Leu Asn Lys Val Leu Gly Arg Glu Val Tyr Ser Ser
    1760                1765                1770

Asn Leu Gln Leu Gly Gly Thr Gln Ile Met Tyr Lys Asn Gly Val
    1775                1780                1785

Ser His Leu Thr Ala Ala Asn Asp Leu Glu Gly Val Leu Ser Ile
    1790                1795                1800

Val Gln Trp Leu Ala Phe Val Pro Glu His Arg Gly Ala Pro Leu
    1805                1810                1815

Pro Ile Met Pro Ser Pro Val Asp Pro Trp Asp Arg Ser Ile Asp
    1820                1825                1830

Tyr Thr Pro Ile Lys Gly Ala Tyr Asp Pro Arg Trp Phe Leu Ala
    1835                1840                1845

Gly Lys Thr Asp Glu Ala Asp Gly Arg Trp Leu Ser Gly Phe Phe
    1850                1855                1860

Asp Lys Gly Ser Phe Gln Glu Thr Leu Ser Gly Trp Ala Gln Thr
    1865                1870                1875

Val Val Val Gly Arg Ala Arg Leu Gly Gly Ile Pro Met Gly Ala
    1880                1885                1890

Ile Ala Val Glu Thr Arg Thr Ile Glu Arg Ile Val Pro Ala Asp
    1895                1900                1905

Pro Ala Asn Pro Leu Ser Asn Glu Gln Lys Ile Met Glu Ala Gly
    1910                1915                1920

Gln Val Trp Tyr Pro Asn Ser Ser Phe Lys Thr Gly Gln Ala Ile
    1925                1930                1935

Phe Asp Phe Asn Arg Glu Gly Leu Pro Leu Ile Ile Phe Ala Asn
    1940                1945                1950

Trp Arg Gly Phe Ser Gly Gly Gln Gln Asp Met Phe Asp Glu Val
```

Leu Lys Arg Gly Ser Leu Ile Val Asp Gly Leu Ser Ala Tyr Lys
        1970                1975                1980

Gln Pro Val Phe Val Tyr Ile Val Pro Asn Gly Glu Leu Arg Gly
    1985                1990                1995

Gly Ala Trp Val Val Leu Asp Pro Ser Ile Asn Ala Glu Gly Met
    2000                2005                2010

Met Glu Met Tyr Val Asp Glu Thr Ala Arg Ala Gly Val Leu Glu
    2015                2020                2025

Pro Glu Gly Ile Val Glu Ile Lys Leu Arg Lys Asp Lys Leu Leu
    2030                2035                2040

Ala Leu Met Asp Arg Leu Asp Pro Thr Tyr His Ala Leu Arg Val
    2045                2050                2055

Lys Ser Thr Asp Val Ser Leu Ser Pro Ala Asp Ala Ala Gln Ala
    2060                2065                2070

Lys Thr Glu Leu Ala Ala Arg Glu Lys Gln Leu Met Pro Ile Tyr
    2075                2080                2085

Gln Gln Val Ala Leu Gln Phe Ala Asp Ser His Asp Lys Ala Gly
    2090                2095                2100

Arg Ile Leu Ser Lys Gly Cys Ala Arg Glu Ala Leu Glu Trp Ser
    2105                2110                2115

Asn Ala Arg Arg Tyr Phe Tyr Ala Arg Leu Arg Arg Val Ala
    2120                2125                2130

Glu Glu Ala Ala Val Lys Arg Leu Gly Asp Ala Asp Pro Thr Leu
    2135                2140                2145

Ser Arg Asp Glu Arg Leu Ala Ile Val His Asp Ala Val Gly Gln
    2150                2155                2160

Gly Val Asp Leu Asn Asn Asp Leu Ala Ala Ala Ala Phe Glu
    2165                2170                2175

Gln Gly Ala Ala Ala Ile Thr Glu Arg Val Lys Leu Ala Arg Ala
    2180                2185                2190

Thr Thr Val Ala Ser Thr Leu Ala Gln Leu Ala Gln Asp Asp Lys
    2195                2200                2205

Glu Ala Phe Ala Ala Ser Leu Gln Gln Val Leu Gly Asp Lys Leu
    2210                2215                2220

Thr Ala Ala Asp Leu Ala Arg Ile Leu Ala
    2225                2230

<210> SEQ ID NO 31
<211> LENGTH: 581
<212> TYPE: PRT
<213> ORGANISM: Rhodosporidium toruloides

<400> SEQUENCE: 31

Met Leu Leu Asp Gly Thr Ala Gly Tyr Leu Ala Glu Gln Leu Gly Ala
1               5                   10                  15

Glu Pro Ser Gln Ile Lys Val Ile Leu Leu Val Ala Ser Val Pro
                20                  25                  30

Leu Ser Leu Ala Tyr Pro Trp Phe Pro Ser Thr Thr Arg Ser Gln Leu
            35                  40                  45

Ala His Leu Tyr Ser Leu Val Pro Ser Ile Ile Phe Leu Cys Phe Val
        50                  55                  60

Leu Asp Leu Gly Leu Gly Phe Val Gln Leu Leu Ala Ser Ser Leu Ala
65                  70                  75                  80

```
Thr Trp Ser Ile Val Arg Ile Gly Ser Arg Asn Asn Trp Gly Ala Leu
                85                  90                  95

Met Pro Trp Thr Val Phe Ala Ile Val Met Gly His Leu Ala Val Asn
            100                 105                 110

His Ile Glu Arg Ser Leu Asn Asn Val Pro Val Thr Thr Ile Glu Ile
        115                 120                 125

Thr Gly Ser Gln Met Val Leu Val Met Lys Leu Ile Ser Phe Ala Trp
    130                 135                 140

Ser Val Tyr Asp Gly Gln Arg Pro Leu Glu Glu Leu Asp Ala Thr Gln
145                 150                 155                 160

Lys Ala Ser Arg Ile Glu Glu Val Pro Gly Leu Leu Pro Phe Leu Gly
                165                 170                 175

Tyr Ala Phe Phe Phe Pro Ser Ile Leu Ala Gly Pro Ser Phe Thr Tyr
            180                 185                 190

Arg Ser Phe Asp Ser Phe Thr Thr His Arg Leu Phe Ala Lys Glu His
        195                 200                 205

Pro Ala Asp Gly Ser Lys Pro Val Asp Pro Thr Val Ile Pro Pro Gly
    210                 215                 220

Arg Arg Arg Lys Ala Ala Lys Arg Phe Ala Thr Gly Ile Ile Tyr Leu
225                 230                 235                 240

Ala Ile Phe Ser Thr Tyr Gly Trp Lys Tyr Gly Met Asn Arg Leu Ile
                245                 250                 255

Asp Arg Lys Ala Val Ala Gly Leu Thr Phe Val Gln Lys Phe Thr Leu
            260                 265                 270

Met Asn Val Ala Gly Phe Ile Ala Arg Thr Lys Tyr Tyr Ala Val Trp
        275                 280                 285

Cys Ile Ala Glu Ser Ala Phe Ile Ile Ser Gly Leu Gly Tyr Asn Pro
    290                 295                 300

Gln Thr Lys His Tyr Asp Ala Ser Arg Asn Val Arg Ile Arg Ser Ile
305                 310                 315                 320

Glu Leu Ala Pro Asn Phe Lys Val Leu Leu Asp Ser Trp Asn Met Asn
                325                 330                 335

Thr Asn Val Trp Leu Arg Glu Cys Ile Tyr Lys Arg Val Ala Lys Lys
            340                 345                 350

Gly Arg Lys Pro Gly Phe Lys Ser Thr Gln Ile Thr Phe Ile Thr Ser
        355                 360                 365

Ala Leu Trp His Gly Thr Asn Pro Cys Tyr Leu Met Thr Phe Val Leu
    370                 375                 380

Gly Gly Phe Cys Gln Ala Val Asn Arg Ser Leu Arg Ala Gly Leu Arg
385                 390                 395                 400

Pro Phe Phe Leu Pro Pro Gly Ala Leu Asn Val Pro Asn Pro Ala Ala
                405                 410                 415

Asn Glu Val Lys Val Gly Asp Lys Ala Ile Ser Leu Pro Ser Thr Pro
            420                 425                 430

Arg Val Lys Leu Gln Pro Pro Gln Thr Pro Leu Lys Thr Leu Tyr
        435                 440                 445

Asp Val Leu Gly Thr Ile Cys Thr Ile Val Val Leu Asn Phe Ala Val
    450                 455                 460

Val Pro Phe Leu Leu Leu Asp Val Gln Ser Ser Leu Gln Ala Trp Ala
465                 470                 475                 480

Glu Val Lys Phe Tyr Ala Leu Trp Met Val Phe Val Pro Phe Phe Val
                485                 490                 495

Leu Asn Val Cys Gly Gly Thr Ala Tyr Leu Lys Arg Leu Gln Arg Ala
```

```
                500             505             510
Arg Asp Lys Lys Ala Glu Gly Lys Arg Arg Ser Lys Glu Glu Gln Glu
        515                 520                 525

Leu Glu Arg Lys Arg Val Glu Trp Glu Lys Ala Glu Glu Asp Lys Arg
        530                 535                 540

Arg Arg Arg Gly Glu Gly Leu Pro Ser Phe Gly Leu Asp Val Glu Gly
545                 550                 555                 560

Met Val Glu Glu Glu Arg Glu Glu Met Arg Gly Glu Ser Val Glu
                565                 570                 575

Gly Arg Lys Glu Leu
            580

<210> SEQ ID NO 32
<211> LENGTH: 721
<212> TYPE: PRT
<213> ORGANISM: Rhodosporidium toruloides

<400> SEQUENCE: 32

Met Val Asn Leu Asp Met Thr Pro Gly Gln Arg Ala Val Leu Thr Ala
1               5                   10                  15

Val Ala Asp Ala Ala Phe Gln Ala His Gly Pro Glu Thr Val Ser Glu
            20                  25                  30

Ile Arg Ser Leu Leu Pro Pro Gly Ala Pro Gln Tyr Gln Leu Glu Asn
        35                  40                  45

Leu Glu Lys Phe Val Arg Ser Lys Phe Ser Asp Leu Pro Gly Ser Val
    50                  55                  60

Asp Ala Leu Ala Gln Gln Phe Cys Thr Ser Leu Ser Lys Glu Asn Val
65                  70                  75                  80

Asp Lys Ile Ala Leu Thr Leu Ser Leu Leu Ser Thr Arg Pro Gly Thr
                85                  90                  95

Leu Leu Leu Ala Gly His Ala Thr Pro Phe Pro Asp Leu Thr Val Gln
            100                 105                 110

Gln Arg Glu Leu Val Leu Gln Lys Trp Arg Val Ser Ser Leu Pro Leu
        115                 120                 125

Leu Arg Gln Ala Phe Arg Gly Leu Val Ser Leu Ala Leu Phe Val Ala
    130                 135                 140

Tyr Asn Leu Tyr Asp Glu Val Leu Phe Ala Ile Gly Tyr Pro Ala Ser
145                 150                 155                 160

Gly Asp Glu Lys Arg Phe Ala Asp Pro Glu Arg Leu Arg Lys His Phe
                165                 170                 175

Pro Tyr Thr Phe Glu Lys Ile Glu Val Ser Tyr Gln Val Phe Asp Thr
            180                 185                 190

Asp Met Leu Val Val Gly Ser Gly Ala Gly Gly Val Val Ala Ser
        195                 200                 205

Glu Leu Ser Lys Lys Gly Trp Asn Val Phe Val Val Glu Lys Gly Gln
    210                 215                 220

Tyr Val Lys Pro Glu Asp Met Ala Gly Thr Gln Arg Asp Gly Phe Lys
225                 230                 235                 240

Arg Leu Tyr Glu Ser Glu Gly Leu Met Ala Thr Glu Asp Gly Ser Met
                245                 250                 255

Asn Val Leu Ala Gly Ser Thr Phe Gly Gly Gly Thr Val Val Asn Trp
            260                 265                 270

Ser Ala Ser Leu Arg Pro Gln His Phe Leu Arg Glu Gln Trp Ala Lys
        275                 280                 285
```

```
Glu His Ser Leu Pro Tyr Phe Leu Ser Thr Glu Tyr Ala Lys Ser Ile
    290                 295                 300

Glu Tyr Val Cys Asp Arg Met Gly Val Ser Asp Glu His Leu Glu His
305                 310                 315                 320

Asn Arg Ala Asn Gln Leu Leu Val Glu Gly Ser Lys Lys Leu Gly Tyr
                325                 330                 335

Pro Ile Ser Lys Ile Pro Gln Asn Thr Gly His Ala His Ala Cys
                340                 345                 350

Gly Tyr Cys Gly Phe Gly Cys Thr Tyr Ser Glu Lys Gln Ser Gly Thr
            355                 360                 365

Val Thr Trp Leu Arg Asp Ala Ala Glu His Gly Ala Lys Phe Met Thr
    370                 375                 380

Glu Thr Ser Val Glu Arg Leu Leu Phe Ala Ala Ser Pro Ser Ser Pro
385                 390                 395                 400

Leu Pro Thr Pro Glu Thr Leu Asp Lys Tyr Thr Pro Ser Ser Ser Arg
                405                 410                 415

Arg His Cys Ile Gly Ala Leu Val Lys Asp Lys Asn Gly Asn Leu Ala
                420                 425                 430

Val Ile Arg Ala Lys Gln Ser Thr Ile Val Ser Ala Gly Thr Ile His
    435                 440                 445

Ser Pro Ala Val Leu Met Arg Ser Gly Leu Lys Asn Pro Arg Ile Gly
    450                 455                 460

Arg Asn Leu Arg Leu His Pro Val Val Phe Thr Thr Gly Leu Tyr Asp
465                 470                 475                 480

Glu His Ile Arg Pro Trp Glu Gly Ala Ile Met Thr Ala Val Thr Gly
                485                 490                 495

Val Gln Glu Asn Trp Asp Gly Ser His His Gly Val Lys Ile Glu Val
                500                 505                 510

Ile Gln Ser Phe Pro Gly Gly Gln Ala Ala Gly Phe Ile Gly Trp Thr
    515                 520                 525

Ser Ser Lys Glu His Lys Lys Thr Met Ala Gln Tyr Gly Asn Leu Leu
    530                 535                 540

Thr Leu Ile Ser Ile Ala Arg Asp Arg Gly Ser Gly Arg Val Phe Leu
545                 550                 555                 560

Asp Ser Glu Gly Lys Pro Arg Met Asp Tyr Thr Val Asn Ser Tyr Asp
                565                 570                 575

Gly Asn Ser Leu Val Arg Gly Thr Ile Ala Ala Ala Glu Ile His Leu
                580                 585                 590

Val Asn Gly Ala Lys Arg Ile Thr Thr Ala Gln Val Asp Val Glu Asp
                595                 600                 605

Tyr Ile Pro Ala Pro Gly His Gln Tyr Leu Ala Asp Pro Lys Trp Lys
    610                 615                 620

Glu Trp Val Ala Lys Ile Glu Lys Ala Gly Val Tyr Pro Gly Arg Cys
625                 630                 635                 640

Ala Ile Gly Ser Ala His Gln Met Gly Ser Cys Gln Met Gly Ala Lys
                645                 650                 655

Pro Ser Thr Ser Val Val Asp Pro Arg Gly Arg Val Trp Gly Thr Asp
                660                 665                 670

Gly Leu Tyr Val Ala Asp Ala Ser Val Phe Pro Thr Ala Ser Gly Val
            675                 680                 685

Asn Pro Met Ile Thr Asn Met Ser Leu Ser His Ser Ile Ala Arg Phe
    690                 695                 700

Ile Asp Glu Asp Ala Arg Glu Thr Ile Ser Gln Pro Val Gln Ala Gln
```

```
                    705                 710                 715                 720

Leu

<210> SEQ ID NO 33
<211> LENGTH: 504
<212> TYPE: PRT
<213> ORGANISM: Rhodosporidium toruloides

<400> SEQUENCE: 33

Met Ala Ala Met Gln Asp Thr Pro Ile Asp Ser Ile Pro Gln Ala Tyr
1               5                   10                  15

Asp Thr Val Thr Lys Ala Phe Leu Ser Gly Lys Thr Arg Pro Ile Ala
            20                  25                  30

Trp Arg Lys Ala Gln Ile Lys Lys Leu Gly Phe Leu Val Gln Asp Asn
        35                  40                  45

Glu Asp Ala Phe Val Arg Ala Leu Glu Gln Asp Phe Gly Arg Pro Ala
    50                  55                  60

Phe Glu Thr Ile Thr Ala Glu Ile Asn Pro Val Lys Ala Glu Ile Asn
65                  70                  75                  80

Glu Val Tyr Asp His Leu Glu Lys Trp Ala Lys Pro Arg Arg Val Lys
                85                  90                  95

Thr Ser Ala Thr Trp Tyr Ala Thr Lys Pro Thr Val Tyr Ser Glu Pro
            100                 105                 110

Lys Gly Val Thr Leu Val Ile Gly Thr Trp Asn Tyr Pro Ile Thr Leu
        115                 120                 125

Leu Leu Val Pro Leu Leu Gly Ala Ile Ser Ala Gly Cys Thr Ala Leu
130                 135                 140

Val Lys Pro Ala Glu Gln Ala Pro His Val Ala Ala Leu Val Ala Asp
145                 150                 155                 160

Leu Leu Pro Lys Tyr Leu Asp Pro Thr Ala Phe Ile Cys Ile Asn Gly
                165                 170                 175

Ala Ile Pro Gln Ala Thr Ala Leu Leu Lys Leu Lys Phe Asp His Ile
            180                 185                 190

Phe Tyr Thr Gly Ser Gly Thr Val Gly Lys Ile Val Ala Arg Ala Ala
        195                 200                 205

Ala Glu His Leu Cys Pro Val Thr Leu Glu Leu Gly Gly Lys Ser Pro
    210                 215                 220

Ala Val Val Leu Asp Asp Ala Asp Ile Glu Val Val Ala Arg Arg Ile
225                 230                 235                 240

Val Trp Ala Lys Phe Thr Asn Ala Gly Gln Ile Cys Ile Ser Thr Asp
                245                 250                 255

Tyr Val Leu Thr Thr Pro Gln Thr Glu Pro Lys Leu Leu Glu Ala Leu
            260                 265                 270

Lys Arg Ala Leu Ala Ala Phe Ser Ala Asn Pro Ala Ala Ser Ser Ser
        275                 280                 285

Ser Glu Lys Ser Ser Thr Ser Leu Val His Asn Pro Asn Tyr Ser Arg
    290                 295                 300

Ile Ile Asn Gln Asn His Tyr Asn Arg Val Ser Lys Leu Leu Asp Ala
305                 310                 315                 320

Thr Lys Gly Glu Val Val Gly Gly Arg Asp Glu Lys Glu Arg
                325                 330                 335

Lys Ile Glu Val Thr Ile Val Arg Gly Val Lys Pro Asp Asp Ser Leu
            340                 345                 350

Met Ser Glu Glu Ile Phe Gly Pro Val Leu Pro Ile Met Thr Leu Pro
```

```
                 355                 360                 365

Thr Leu Asp Asp Met Val Lys Phe Ile Gln Ser Arg Asp Thr Pro Leu
    370                 375                 380

Ala Leu Tyr Val Phe Thr Gln Ser Lys Lys Asn Arg Asp Phe Ile Phe
385                 390                 395                 400

Glu Arg Thr Arg Ser Gly Gly Phe Val Gln Asn Asp Val Leu Val Gln
                405                 410                 415

Phe Met Ile Pro Gly Leu Pro Phe Gly Gly Thr Gly Ala Ala Gly Tyr
            420                 425                 430

Gly Asn Tyr His Gly Arg Arg Thr Phe Asp Thr Phe Ser His Glu Arg
        435                 440                 445

Ala Ser Ala Asn Val Pro Thr Trp Met Asp Met Ile Met Ala Ser Arg
    450                 455                 460

Tyr Pro Pro Tyr Thr Gln Lys Lys Leu Lys Met Leu Leu Phe Ala Thr
465                 470                 475                 480

Lys Ala Val Ile Lys Lys Pro Ser Lys Phe Gly Ser Ile Ser Arg Leu
                485                 490                 495

Leu Lys Lys Leu Thr Gly Gln Ala
            500

<210> SEQ ID NO 34
<211> LENGTH: 421
<212> TYPE: PRT
<213> ORGANISM: Rhodosporidium toruloides

<400> SEQUENCE: 34

Met Ala Ile Ser Pro Glu Gln Arg Ile Lys Val Gln Asn Pro Ile Val
1               5                   10                  15

Glu Met Asp Gly Asp Glu Met Thr Arg Ile Ile Trp His Lys Ile Lys
            20                  25                  30

Lys Asp Leu Ile Leu Pro Phe Leu Asp Val Asp Ile Lys Tyr Tyr Asp
        35                  40                  45

Leu Gly Leu Glu Tyr Arg Asp Gln Thr Asp Asp Gln Val Thr Val Asp
    50                  55                  60

Ala Ala Glu Ala Ile Leu Lys Tyr Gly Val Gly Val Lys Cys Ala Thr
65                  70                  75                  80

Ile Thr Pro Asp Glu Ala Arg Val Glu Glu Phe Lys Leu Lys Lys Met
                85                  90                  95

Trp Lys Ser Pro Asn Gly Thr Ile Arg Asn Ile Leu Gly Gly Thr Val
            100                 105                 110

Phe Arg Glu Pro Ile Ile Val Gln Lys Val Pro Lys Ala Val Pro Gly
        115                 120                 125

Trp Thr Lys Pro Ile Ile Val Gly Arg His Ala Phe Gly Asp Gln Tyr
    130                 135                 140

Arg Ser Thr Asp Ile Val Val Pro Glu Ala Gly Lys Leu Glu Leu Val
145                 150                 155                 160

Tyr Thr Pro Asp Asp Lys Ser Lys Gln Pro Thr Asn Leu Glu Val Phe
                165                 170                 175

His Phe Lys Gly Pro Gly Val Gly Leu Ala Met Tyr Asn Thr Lys Gln
            180                 185                 190

Ser Ile Thr Asp Phe Ala Gln Ser Ser Phe Lys Leu Ala Ile Glu Lys
        195                 200                 205

Lys Leu Pro Leu Tyr Met Ser Thr Lys Asn Thr Ile Leu Lys Gly Tyr
    210                 215                 220
```

```
Asp Gly Gln Trp Lys Asp Ile Phe Gln Glu Ile Tyr Asp Thr Gln Tyr
225                 230                 235                 240

Lys Ala Lys Phe Glu Glu Leu Gly Ile Trp Tyr Glu His Arg Leu Ile
            245                 250                 255

Asp Asp Met Val Ala Gln Met Ile Lys Ser Ser Gly Gly Tyr Ile Met
            260                 265                 270

Ala Leu Lys Asn Tyr Asp Gly Asp Val Gln Ser Asp Val Val Ala Gln
            275                 280                 285

Gly Phe Gly Ser Leu Gly Leu Met Ser Ser Glu Leu Val Thr Pro Asp
            290                 295                 300

Gly Lys Ile Ile Glu Ser Glu Ala Ala His Gly Thr Val Thr Arg His
305                 310                 315                 320

Tyr Arg Glu His Gln Lys Gly Asn Glu Thr Ser Thr Asn Ser Ile Ala
            325                 330                 335

Ser Ile Tyr Ala Trp Thr Arg Gly Leu Lys Phe Ala Gly Lys Arg Asp
            340                 345                 350

Gly Asn Glu Arg Leu Val Gln Phe Ala Asn Asp Met Glu Gln Ala Cys
            355                 360                 365

Val Asp Ala Val Asp Ile Asp Gly Val Met Thr Lys Asp Leu Ala Leu
            370                 375                 380

Ser Ile His Gly Lys Asn Met Lys Arg Glu His Tyr Val Leu Thr Leu
385                 390                 395                 400

Glu Tyr Leu Asp His Ile Ala Ala Lys Val Thr Glu Lys Phe Leu Ala
            405                 410                 415

Asn Ala Pro Lys Leu
            420

<210> SEQ ID NO 35
<211> LENGTH: 684
<212> TYPE: PRT
<213> ORGANISM: Rhodosporidium toruloides

<400> SEQUENCE: 35

Met Pro Val Ser Val Thr Val Gly Leu Arg Cys Asp Asp Ala Ala Glu
1               5                   10                  15

Leu Ala Ser Ser Thr Arg Ser His Thr Leu Ile Pro Ala Ser Pro Ser
            20                  25                  30

Leu Leu Pro Leu Ser Gly Ser Ala Lys His Pro Leu Glu His Thr His
            35                  40                  45

Pro Thr Ser Glu Leu Ala Gln Pro Leu Asn Arg Thr Met Ser Ser Pro
            50                  55                  60

Gly Gln Leu Ala Asp Asp Gln Val Tyr Leu Gly Thr Tyr Leu Leu Asp
65                  70                  75                  80

Arg Leu Ala Gln Leu Asp Val Lys Cys Leu Phe Gly Val Pro Gly Asp
            85                  90                  95

Phe Asn Leu Thr Phe Leu Asp Leu Val Glu Glu His Pro Glu Val Gln
            100                 105                 110

Trp Ile Gly Asn Cys Asn Glu Leu Asn Ala Ala Tyr Ala Ala Asp Gly
            115                 120                 125

Tyr Ala Arg Val Lys Gln Ala Gln Ile Asn Ser Ile Arg Glu Gly Glu
            130                 135                 140

Gln Ala Glu Ser Lys Pro Gly Gln Ala Thr Thr His Gly Gly Lys Asp
145                 150                 155                 160

Lys Thr Gln Gly Gly Val Arg Gly Leu Gly Ala Leu Leu Thr Thr Phe
            165                 170                 175
```

```
Gly Val Gly Glu Leu Ser Ala Val Asn Gly Ile Ala Gly Ala Tyr Ser
            180                 185                 190

Glu Arg Val Pro Ile Leu His Ile Val Gly Val Pro Ser Thr Lys Leu
            195                 200                 205

Gln Lys Ser Lys Ala Leu Leu His His Thr Leu Gly Asn Gly Glu Phe
    210                 215                 220

Thr Val Phe Glu Gln Ala Ser Ala Gly Ile Thr Cys Ala Arg Ala Phe
225                 230                 235                 240

Leu Gln Arg Ala Glu Glu Ala Ala Glu Ile Asp Arg Val Leu Leu
                245                 250                 255

Ala Ala Leu Thr Thr Ala Arg Pro Ala Tyr Val Thr Leu Pro Thr Asp
            260                 265                 270

Leu Val Phe Val Pro Val Pro Lys Lys Arg Leu Glu Asp Pro Ile Ile
            275                 280                 285

Pro Met Arg Val Gly Phe Glu Asp Lys Asn Val Leu Pro Thr Gly Lys
    290                 295                 300

Lys Val Glu Glu Glu Lys Asn Arg Leu Gln Phe Val Val Gly Glu
305                 310                 315                 320

Ile Glu Arg Leu Trp Asn Glu Ala Lys Glu Pro Ile Ile Leu Ile Asp
                325                 330                 335

Ala Cys Ala Ile Arg Tyr Gly Val Gly His Leu Val Arg Asp Leu Val
            340                 345                 350

His Ala Thr Gly Val Lys Phe Tyr Thr Thr Pro Met Gly Arg Thr Ala
        355                 360                 365

Ile Asp Glu Asp Pro Ser Asn Gly Phe Gly Gly Tyr Val Gly Glu
    370                 375                 380

Val Thr Asp Pro Lys Val Lys Glu Val Glu Lys Thr Asp Leu Ala
385                 390                 395                 400

Val Met Val Gly Ser Leu Lys Ser Asp Phe Asn Thr Gly Glu Phe Ser
                405                 410                 415

Tyr Ser Phe Pro Thr Glu Gln Thr Val Glu Leu His Ser Asp His Thr
                420                 425                 430

Leu Val Gln Tyr Ala His Tyr Pro Ser Val Ser Phe His Gln Leu Leu
            435                 440                 445

Pro Ala Leu Thr Lys Val Leu Lys His Lys Pro Asn Val Thr His Pro
    450                 455                 460

Pro Ser Asp Arg Gly Leu Gln Thr Gln Ile Pro Asp Gly Asp Ala Asp
465                 470                 475                 480

Lys Val Val Thr Gln Ala Ala Phe Trp Pro Met Met Gly Lys Phe Phe
                485                 490                 495

Glu Glu Gly Asp Ile Val Val Ala Glu Thr Gly Thr Ser Ser Phe Gly
            500                 505                 510

Met Ile Ser Thr Pro Leu Pro Lys Gly Ser Thr Phe Val Ser Gln Val
    515                 520                 525

Leu Trp Gly Ser Ile Gly Trp Thr Gly Gly Ala Thr Leu Gly Ala Leu
530                 535                 540

Leu Ala Ala Lys Glu Ala Pro Lys Pro Arg Arg Val Ile Leu Phe Ile
545                 550                 555                 560

Gly Asp Gly Ser Leu Gln Leu Thr Val Gln Glu Val Ala Thr Met Val
            565                 570                 575

Arg Leu Asp Leu Lys Pro Ile Leu Val Val Leu Asn Asn Asp Gly Tyr
            580                 585                 590
```

```
Thr Ile Glu Lys Lys Ile His Gly Glu Thr Ala Gly Tyr Asn Asp Ile
            595                 600                 605

Ser Ser Trp Lys Trp Gln Ser Met Leu Asp Phe Phe Asn Ala Tyr Asp
    610                 615                 620

Gln Pro Lys Pro Thr Arg Ser Trp Leu Ala Pro Thr Arg Ala Asp Leu
625                 630                 635                 640

Glu Arg Ile Leu Ala Asp Asp Glu Phe Arg Lys Ala Asp Arg Ile Gln
                645                 650                 655

Val Leu Glu Val Lys Met Asp Lys Leu Asp Ala Pro Val Ala Leu Glu
                660                 665                 670

Lys Gln Gly Lys Leu Ser Ala Glu Leu Asn Ala Ala
                675                 680

<210> SEQ ID NO 36
<211> LENGTH: 503
<212> TYPE: PRT
<213> ORGANISM: Rhodosporidium toruloides

<400> SEQUENCE: 36

Met Ser Asn Asn Leu Thr Ala Ser Leu Thr Phe Pro Glu Gly His Ser
1               5                   10                  15

Leu Lys Ser Leu Asp Phe Pro Val Gly Leu Phe Ile Asn Asn Glu Tyr
                20                  25                  30

Ser Pro Ala Ser Gly Glu Thr Ile Glu Val Arg Ala Pro Ala Phe
            35                  40                  45

Asp Lys Val Ile Ala His Val Pro Arg Gly Thr Ala Glu Asp Val Asp
    50                  55                  60

Arg Ala Val Glu Ala Ala Gln Lys Ala Tyr Asp Thr Val Trp Gly Glu
65                  70                  75                  80

Arg Cys Pro Gly His Lys Arg Gly Lys Leu Leu Met Gln Leu Ala Asp
                85                  90                  95

Leu Phe Glu Gln His Val Glu Gln Leu Ala Ser Ile Glu Ala Leu Asp
                100                 105                 110

Asn Gly Lys Ala Tyr Asn Ile Ala Lys Ala Phe Asp Val Ser Glu Ala
            115                 120                 125

Ala Ala Cys Leu Arg Tyr Tyr Gly Gly Trp Ala Asp Lys Glu His Gly
    130                 135                 140

Lys Val Ile Glu Val Asp Asn Ser Lys Met Ala Ile Thr Lys His Glu
145                 150                 155                 160

Pro Ile Gly Val Ile Gly Gln Ile Ile Pro Trp Asn Phe Pro Leu Leu
                165                 170                 175

Met Phe Ala Trp Lys Leu Gly Pro Ala Leu Ala Cys Gly Asn Cys Ile
                180                 185                 190

Val Ile Lys Val Ala Glu Thr Thr Pro Leu Ser Ala Phe Tyr Ala Thr
            195                 200                 205

Gln Leu Ile Ala Lys Val Phe Pro Pro Gly Val Val Asn Val Val Thr
    210                 215                 220

Gly Tyr Gly Asn Glu Val Gly Ala Ala Ile Ser Gly His Met Lys Ile
225                 230                 235                 240

Leu Lys Val Ala Phe Thr Gly Ser Thr Leu Val Gly Arg Thr Ile Met
                245                 250                 255

Gln Ala Ala Ala Lys Ser Asn Leu Lys Pro Val Thr Leu Glu Leu Gly
                260                 265                 270

Gly Lys Ser Pro Asn Ile Ile Phe Asp Asp Ala Asp Met Glu Gln Ala
            275                 280                 285
```

```
Val Ser Trp Ser Ala Phe Gly Leu Phe Phe Asn Ala Gly Gln Cys Cys
    290                 295                 300

Cys Ala Gly Ser Arg Ile Phe Val Gln Glu Ser Ile Tyr Asp Glu Phe
305                 310                 315                 320

Leu Glu Lys Leu Thr Ala Lys Val Lys Ser Met Lys Val Gly Gln Pro
                325                 330                 335

Phe Ala Ala Asp Ser Phe Val Gly Pro Ala Thr Ser Lys Leu Gln Phe
            340                 345                 350

Asp Arg Ile Thr Ala His Ile Gln Ser Gly Lys Asp Glu Gly Ala Lys
        355                 360                 365

Val His Val Gly Gly Asn Arg His Gly Asp Glu Gly Tyr Phe Ile Glu
    370                 375                 380

Pro Thr Ile Phe Thr Asp Val Thr Pro Asn Met Arg Ile Ala Gln Glu
385                 390                 395                 400

Glu Ile Phe Gly Pro Val Leu Val Val Gln Lys Phe Lys Asp Glu Ser
            405                 410                 415

Asp Val Val Ala Lys Ala Asn Asp Thr Met Tyr Gly Leu Ala Ala Ala
            420                 425                 430

Ile Phe Ser Arg Asp Ile Ser Arg Ala Met Arg Ile Ala Asn Ser Val
        435                 440                 445

His Ala Gly Thr Val Trp Leu Asn Cys Tyr Asn Gln Leu Asn Ser Gln
    450                 455                 460

Val Pro Phe Gly Gly Phe Lys Gln Ser Gly Ile Gly Arg Glu Leu Gly
465                 470                 475                 480

Ser Tyr Ala Leu His Asn Tyr Thr Ala Val Lys Ala Ile His Ile Asn
            485                 490                 495

Leu Ser Gln Pro Asn Pro Leu
            500
```